US008349329B2

(12) United States Patent
Goddard et al.

(10) Patent No.: US 8,349,329 B2
(45) Date of Patent: Jan. 8, 2013

(54) ANTIBODIES THAT BIND TO PRO286

(75) Inventors: Audrey Goddard, San Francisco, CA (US); Paul J. Godowski, Burlingame, CA (US); Austin L. Gurney, Belmont, CA (US); Melanie R. Mark, Burlingame, CA (US); Ruey-Bing Yang, Foster City, CA (US)

(73) Assignee: Genetech, Inc., South San Francisco, CA (US)

( * ) Notice: Subject to any disclaimer, the term of this patent is extended or adjusted under 35 U.S.C. 154(b) by 0 days.

(21) Appl. No.: 12/717,061

(22) Filed: Mar. 3, 2010

(65) Prior Publication Data
US 2010/0234576 A1 Sep. 16, 2010

Related U.S. Application Data

(63) Continuation of application No. 09/202,054, filed as application No. PCT/US98/21141 on Oct. 7, 1998, now Pat. No. 7,696,327.

(60) Provisional application No. 60/062,250, filed on Oct. 17, 1997, provisional application No. 60/065,311, filed on Nov. 13, 1997, provisional application No. 60/083,322, filed on Apr. 28, 1998, provisional application No. 60/090,863, filed on Jun. 26, 1998.

(51) Int. Cl.
*A61K 39/395* (2006.01)

(52) U.S. Cl. ............... 424/139.1; 424/145.1; 424/142.1; 424/141.1

(58) Field of Classification Search .................. None
See application file for complete search history.

(56) References Cited

U.S. PATENT DOCUMENTS

| 6,005,089 | A  | * | 12/1999 | Lanza et al. ............ 536/23.5 |
| 6,083,688 | A  | * | 7/2000  | Lanza et al. ............ 435/6 |
| 6,521,448 | B1 | * | 2/2003  | Edge et al. ............ 435/320.1 |
| 7,670,603 | B2 | * | 3/2010  | Hardiman et al. ........ 424/143.1 |
| 7,705,134 | B2 | * | 4/2010  | Wu et al. ............. 530/387.9 |
| 2004/0162309 | A1 | * | 8/2004  | Gorden et al. .......... 514/292 |
| 2005/0245564 | A1 | * | 11/2005 | Gorden et al. .......... 514/292 |

FOREIGN PATENT DOCUMENTS

| EP | 0 307 247   | 3/1989  |
| EP | 0 980 429   | 2/2000  |
| EP | 1 386 931   | 2/2004  |
| WO | WO 98/50547 | 11/1998 |
| WO | WO 99/20756 | 4/1999  |

OTHER PUBLICATIONS

C. Macquin, Locus AAZ95439 (Genbank) 1059 aa linear PRI Nov. 25, 2009 (accessed Dec. 20, 2010) (reproduced in the Office Action).*
Altschul et al., "Local Alignment Statistics," Methods in Enzymology, 1996, 266: 460-480.
Bazil et al., "Biochemical Characterization of a Soluble Form of the 53-kDa Monocyte Surface Antigen," European Jnl. of Immunology, 1986, 16(12): 1583-1589.
Belvin et al., "A Conserved Signaling Pathway: the Drosophila Toll-Dorsal Pathway," Ann. Review of Cell & Developmental Biology, 1996, 12: 393-416.
Bolivar et al., "Construction and Characterization of New Cloning Vehicles. II. A Multipurpose Cloning System," Gene, 1977, 2: 95-113.
Croston et al., "NF-KB Activation by Interleukin-1 (IL-1) Requires an IL-1 Receptor-Associated Protein Kinase Activity," Jnl. of Bio. Chem., 1995, 270(28): 16514-16517.
Dangl et al., "La Dolce Vita: A Molecular Feast in Plant-Pathogen Interactions," Cell, 1997, 91(1): 17-24.
Delude et al., "CD14-Mediated Translocation of Nuclear Factor-Kappa B Induced by Lipopolysaccharide Does Not Require Tyrosine Kinase Activity," Jnl. of Bio. Chem., 1994, 269(35): 22253-22260.
GenBank Locus HSU79260 (Accession U792601). Andreson et al., 1996, web page printout.
GenBank Locus HSU88540 (Accession U88540) Rock et al., 1998, web page printout.
GenBank Locus HSU88878 (Accession U88878) Rock et al., 1998, web page printout.
GenBank Locus HSU88879 (Accession U88879), Rock et al., 1998, web page printout.
GenBank Locus HSU88880 (Accession U88880), Rock et al., 1998, web page printout.
GenBank Locus HSU88881 (Accession U88881), Rock et al., 1998, web page printout.
GenBank Locus HUMRSC786 (Accession D13637), Nomura et al., 1999, web page printout.
Hashimoto et al., "The Toll Gene of Drosophila, Required for Dorsal-Ventral Embryonic Polarity, Appears to Encode a Transmembrane Protein," Cell, 1988, 52(2): 269-279.
Holmes et al., "Structure and Functional Expression of a Human Interleukin-8 Receptor," Science, 1991, 253(5025): 1278-1280.
Lee et al., "Glycosyl-Phosphatidylinositol-Anchored or Integral Membrane Forms of CD14 Mediate Identical Cellular Responses to Endotoxin," PNAS USA, 1993, 90: 9930-9934.
Lemaitre et al., "Drosophila Host Defense: Differential Induction of Antimicrobial Peptide Genes After Infection by Various Classes of Microorganisms," PNAS USA, 1997, 94(26):14614-14619.
Lemaitre et al., "Functional Analysis and Regulation of Nuclear Import of Dorsal During the Immune Response in Drosophila," EMBO Jnl., 1995, 14(3): 536-545.
Lemaitre et al., "The Dorsoventral Regulatory Gene Cassette Spatzle/Toll/Cactus Controls the Potent Antifungal Response in Drosophila Adults," Cell, 1996, 86(6): 973-983.
Lu et al., "An Optimized Protocol for In Situ Hybridization Using PCR-Generated $^{33}$P-Labeled Riboprobes," Cell Vision, 1994, 1(2): 169-176.

(Continued)

Primary Examiner — Christine J Saoud
(74) Attorney, Agent, or Firm — Gates & Cooper LLP

(57) ABSTRACT

The invention relates to the identification and isolation of novel DNAs encoding the human Toll proteins PRO285, PRO286, and PRO358, and to methods and means for the recombinant production of these proteins. The invention also concerns antibodies specifically binding the PRO285, or PRO286, or PRO358 Toll protein.

10 Claims, 21 Drawing Sheets

OTHER PUBLICATIONS

Luoh, "Cloning and Characterization of a Human Leptin Receptor Using a Biologically Active Leptin Immunoadhesin," J. of Molecular Endocrinology, 1997, 18: 77-85.

Marchant et al., "Lipopolysaccharide Induces Up-Regulation of CD14 Molecule on Monocytes in Human Whole Blood," European J. of Immunology, 1992, 22(6): 1663-1665.

Mark et al., "rse, a Novel Receptor-Type Tyrosine Kinase with Homology to Axl/Ufo, is Expressed at High Levels in the Brain," Jnl. of Bio. Chem., 1994, 269(14): 10720-10728.

Medzhitov et al., "A Human Homologue of the Drosophila Toll Protein Signals Activation of Adaptive Immunity," Nature, 1997, 388(6640): 394-397.

Medzhitov et al., "Innate Immunity: the Virtues of a Nonclonal System of Recognition," Cell, 1997, 91(3): 295-298.

Medzhitov et al., "Self-Defense: The Fruit Fly Style," PNAS USA, 1998, 95(2): 429-430.

Morisato et al., "The Spatzle Gene Encodes a Component of the Extracellular Signaling Pathway Establishing the Dorsal-Ventral Pattern of the Drosophila Embryo," Cell, 1994, 76(4): 677-688.

NCBI/GenBank EST; Locus HSU88881.

Parrillo, "Pathogenetic Mechanisms of Septic Shock," New England J. of Med., 1993, 328(20): 1471-1477.

Rietschel et al., "Bacterial Endotoxins," Scientific American, 1992, 267(2): 54-61.

Rock et al., "A Family of Human Receptors Structurally Related to Drosophila Toll," PNAS USA, 1998, 95(2): 588-593.

Ruppert et al., "Cloning and Expression of Human $TAF_{II}250$: A TBP-Associated Factor Implicated in Cell-Cycle Regulation," Nature, 1993, 362: 175-179.

Sompayrac et al., "Efficient Infection of Monkey Cells with DNA of Simian Virus 40," PNAS USA, 1981, 78(12): 7575-7578.

Thimmappaya et al., "Adenovirus VAI RNA is Required for Efficient Translation of Viral mRNAs at Late Times After Infection," Cell, 1982, 31(3 pt. 2): 543-551.

Ulevitch et al., "Receptor-Dependent Mechanisms of Cell Stimulation by Bacterial Endotoxin," Ann. Rev. of Immunol., 1995, 13: 437-457.

Yang et al., "Toll-Like Receptor-2 Mediates Lipopolysaccharide-Induced Cellular Signalling," Nature, 1998, 395(6699): 284-288.

Taguchi et al., "Chromosomal Localization of TIL, a Gene Encoding a Protein Related to the Drosophila Transmembrane Receptor Toll, to Human Chromosome 4p14," Genomics, 1996, 32: 486-488.

* cited by examiner

><MW: 120922
MVFPMWTLKRQILILFNIILISKLLGARWFPKTLPCDVTLDVPKNHVIVDCTDKHLTEIP
GGIPTNTTNLTLTINHIPDISPASFHRLDHLVEIDFRCNCVPIPLGSKNNMCIKRLQIKP
RSFSGLTYLKSLYLDGNQLLEIPQGLPPSLQLLSLEANNIFSIRKENLTELANIEILYLG
QNCYYRNPCYVSYSIEKDAFLNLTKLKVLSLKDNNVTAVPTVLPSTLTELYLYNNMIAKI
QEDDFNNLNQLQILDLSGNCPRCYNAPFPCAPCKNNSPLQIPVNAFDALTELKVLRLHSN
SLQHVPPRWFKNINKLQELDLSQNFLAKEIGDAKFLHFLPSLIQLDLSFNFELQVYRASM
NLSQAFSSLKSLKILRIRGYVFKELKSFNLSPLHNLQNLEVLDLGTNFIKIANLSMFKQF
KRLKVIDLSVNKISPSGDSSEVGFCSNARTSVESYEPQVLEQLHYFRYDKYARSCRFKNK
EASFMSVNESCYKYGQTLDLSKNSIFFVKSSDFQHLSFLKCLNLSGNLISQTLNGSEFQP
LAELRYLDFSNNRLDLLHSTAFEELHKLEVLDISSNSHYFQSEGITHMLNFTKNLKVLQK
LMMNDNDISSSTSRTMESESLRTLEFRGNHLDVLWREGDNRYLQLFKNLLKLEELDISKN
SLSFLPSGVFDGMPPNLKNLSLAKNGLKSFSWKKLQCLKNLETLDLSHNQLTTVPERLSN
CSRSLKNLILKNNQIRSLTKYFLQDAFQLRYLDLSSNKIQMIQKTSFPENVLNNLKMLLL
HHNRFLCTCDAVWFVWWVNHTEVTIPYLATDVTCVGPGAHKGQSVISLDLYTCELDLTNL
ILFSLSISVSLFLMVMMTASHLYFWDVWYIYHFCKAKIKGYQRLISPDCCYDAFIVYDTK
DPAVTEWVLAELVAKLEDPREKHFNLCLEERDWLPGQPVLENLSQSIQLSKKTVFVMTDK
YAKTENFKIAFYLSHQRLMDEKVDVIILIFLEKPFQKSKFLQLRKRLCGSSVLEWPTNPQ
AHPYFWQCLKNALATDNHVAYSQVFKETV

FIG. 1

><insert starts here>CCCATCTCAAGCTGATCTCTGGCACCTCTCATGCTCTGCTCTCTTCAACCAGACCCTCTACA
TTCCATTTTGAAGAAGACTAAAA
><MET {trans=1-s, dir=f, res=1}>
ATGGGTGTTTCCAATGTGGACACTGAAGAGACACAAATTCTTATCCTTTTTAACATAATCCTA
ATTTCCAAACTCCTTGGGGCTAGATGGTTTCCTAAAACTCTGCCCTGTGATGTCACTCTG
GATGTTCAAAGAACCATGTGATCGTGACAGACAAGCATTTGACAGAAATTCCT
GGAGGGTATTCCCACGAACAACACGAACCTCACCCTCACCATTAACCACATACCAGACATC
TCCCCAGCGTCCTTTCACAGACTGGACCATCTGGTAGAGATCGATTTCAGATGCAACTGT
GTACCTATTCCACTGGGTCAAAAACAACATGTGCATCAAGAGGCTGCAGATTAAACCC
AGAAGCTTTAGTGGACTCACTTATTTAAATCCCTTTACCTGGATGAAACCAGCTACTA
GAGATACCGCAGGGCCTCCCGCCTAGCTTACAGCTTCTCAGCCTTGAGGCCAACAACATC
TTTTCCATCAGAAAAGAGAATCTAACAGAACTGGCCAACATAGAAATACTCTACCTGGGC
CAAAACTGTTATTATCGAAATCCTTGTTTATGTTTCATATTCAATAGAGAAAGATGCCTTC
CTAAACTTGACAAAGTTAAAAGTGCTCTCCCCTGAAAGATAACAATGTCACAGCCGTCCT
ACTGTTTTTGCCATCTACTTTAACAGAACTATATCTCTACAACAACATGATTGCAAAAATC
CAAGAAGATGATTTTAATAACCTCAACCAATTACAAATTCTTGACCTAAGTGAAATTGC
CCTCGTGTTATAATGCCCCATTTCCTTGTGCGCGCAGAATTAAAAGTTTTACGTCTACACAGTAAC
ATCCCTGTAAATGCTCTTTGATGCGCTAGAATGGTTTAAGAACATCAACAACTCCAGAACTGGAT
TCTCTTCAGCATGTGCCCCCAAGATGGTTTAAGAACATCAACAACTCCAGAACTGGAT
CTGTCCCAAAACTTCTTGGCCAAAGAAATTGGGGATGCTAAATTTCTGCATTTTCTCCC
AGCCTCATCCAATTGGATCTCTGTCTTTCACTGAAAGCCTGAAAATTCTGCGATCAGAGATAT
AATCTATCACAGCATTTCTTCTTCACTGAAAGCCTGAAAATTCTGCGATCAGAGATAT
GTCTTTAAAGAGTTGAAAGCTTTAACCTCTCGCCATTACATAATCTTCAAAATCTTGAA
GTTCTTGATCTTGGCACTAACTTTATAAATTGCTAACCTCAGCATGTTTAAACAATTT
AAAAGACTGAAAGTCATAGATCTTTCAGTGAATAAAATATCACCTTCAGGAGATTCAAGT
GAAGTTGGCTTCTCTGCTCAAATGCCAGAACTTCTGTAGAAAGTTATGAACCCCAGGTCCTG
GAACAATTACATTATTTCAGATATGATAAGTGCAAGGAGTTGCAGATTCAAAAACAAA
GAGGCTTCTTTCATGTCTGTTAATGAAAGCTGCTACAAGTATGGGCAGACCTTGGATCTA
AGTAAAAAATAGTATATTTTTGTCAAGTCCCTCTGATTTTCAAGTCTTTTCTTCCCTCAAA

FIG. 2A

```
TGCCTGAATCTGTCAGGAAATCTCATTAGCCAAACTCTTAATGGCAGTGAATTCCAACCT
TTAGCAGAGCTGAGATATTGGACTTCTCCAACAACCGGCTTGATTTACTCCATTCAACA
GCATTTGAAGAGCTTCACAAACTGGAAGTTCTGGATATAAGCAGTAATAGCCATTATTT
CAATCAGAAGGAATTACTCATATGCTAAACTTTACCAAGAACCTAAAGGTTCTGCAGAAA
CTGATGATGAACGACAATGACATCTCTTCCTCCACCAGCAGGACCATGGAGAGTGAGTCT
CTTAGAACTCTGGAATTCAGAGGAAATCACTTAGATGTTTTATGGAGAGAAGGTGATAAC
AGATACTTACAATTATTCAAGAATCTGCTAAAATTAGAGGAATTAGACATCTCTAAAAAT
TCCCTAAGTTTCTTGCCTTCTGGAGTTTTGATGGTATGCCTCCAAATCTAAAGAATCTC
TCTTTGGCCAAAAATGGGCTCAAATCTTTCAGTTGGAAGAAACTCCAGTGTCTAAAGAAC
CTGGAAACTTTGGACCTCAGCCACCACAACCTGACCACTGTCCCTGAGAGATTATCCAAC
TGTTCCAGAAGCCTCAAGAATCTGATTCTTAAGAATAATCAAATCAGGAGTCTGACGAAG
TATTTCTACAAGATGCCTTCCAGTTGCGATATCTGGATCTCAGCTCAAATAAAATCCAG
ATGATCCAAAAGACCAGCTTCGTGACCTTCCCAGAAAATGTCCTCAACAATCTGAAGATGTTGCTTTTG
CATCATAATCGGTTTCTGTGCACCTGATGCTGTGGTTTGTCTGGTGGGCCAGGAGCACAC
ACGGAGGTGACTATTCCTTACCTGTCTGGCCACAGATGTGACTTGTGTGAGTTAGATCTGACTAACCTG
AAGGGCCAAAGTGTGATCTCCCTGGATCGTACACCTGAGTTAGATCTGACTAACCTG
ATTCTGTTCTCACTTCTCCATATCTGTATCTCTCTTCCATGGTGATGATGACAGCAAGT
CACCTCTATTTCTGGGATGTGTGGTATATTTACCATTTCTGTAAGCCAAGATAAAGGGG
TATCAGCGTCTAATATCACCAGACTGTTGCTATGATGCTTTTATTGTGTATGACACTAAA
GACCCAGCTGTGACCGAGTGGGTTTTGGCTGGAGCTGGTGGCCAAACTGGAAGACCCAAGA
GAGAAACATTTAATTTATGTCTCGAGGAAAGAACAGTGTTGTTGTGATGACAGACAAG
GAAACCTTTCCCAGAGCATACAGCTTAGCAAAAGATAGCATTTTACTTGTCCCATCAGAGGCTCATGGAT
TATGCAAAGACTGAAAATTTAAGATAGCATTTTCTTGAGAAGCCCTTTCAGAAGTCCAAGTTC
GAAAAGTTGATGTGATTATCTTGATATTTCTGTGGAGTTCTGTCTTGAGTGCCAACAAACCCGCAA
CTCCAGCTCCGGAAAAGGCTTCTGGCAGTGTCTAAAGAACGCCCTGGCCACAGACAATCATGTGGCC
GCTCACCCATACTTCTGGCAGTGTCTAGCCCTTCTTTGCAAAACACAACTGCCTAGTT
TATAGTCAGGTGTTCAAGGAAACGGTCTAGCCCTTCTTTGCAAAACACAACTGCCTAGTT
TACCAAGGAGAGGCCTGGC
```

FIG. 2B

MENMFLQSSMLTCIFLLISGSCELCAEENFSRSYPCDEKKQNDSVIAECSNRRLQEVPQT
VGKYVTELDLSDNFITHITNESFQGLQNLTKINLNHNPNVQHQNGNPGIQSNGLNITDGA
FLNLKNLRELLLEDNQLPQIPSGLPESLTELSLIQNNIYNITKEGISRLINLKNLYLAWN
CYFNKVCEKTNIEDGVFETLTNLELLSLSFNSLSHVPPKLPSSLRKLFLSNTQIKYISEE
DFKGLINLTLLDLSGNCPRCFNAPFPCVPCDGGASINIDRFAFQNLTQLRYLNLSSTSLR
KINAAWFKNMPHLKVLDLEFNYLVGEIVSGAFLTMLPRLEILDLSFNYIKGSYPQHINIS
RNFSKLLSLRALHLRGYVFQELREDDFQPLMQLPNLSTINLGINFIKQIDFKLFQNFSNL
EIIYLSENRISPLVKDTRQSYANSSSFQRHIRKRRSTDFEFDPHSNFYHFTRPLIKPQCA
AYGKALDLSLNSIFFIGPNQFENLPDIACLNLSANSNAQVLSGTEFSAIPHVKYLDLTNN
RLDFDNASALTELSDLEVLDLSYNSHYFRIAGVTHHLEFIQNFTNLKVLNLSHNNIYTLT
DKYNLESKSLVELVFSGNRLDILWNDDDNRYISIFKGLKNLTRLDLSLNRLKHIPNEAFL
NLPASLTELHINDNMLKFFNWTLLQQFPRLELLDLRGNKLLFLTDSLSDFTSSLRTLLLS
HNRISHLPSGFLSEVSSLKHLDLSSNLLKTINKSALETKTTTKLSMLELHGNPFECTCDI
GDFRRWMDEHLNVKIPRLVDVICASPGDQRGKSIVSLELTTCVSDVTAVILFFFTFFITT
MVMLAALAHHLFYWDVWFIYNVCLAKVKGYRSLSTSQTFYDAYISYDTKDASVTDWVINE
LRYHLEESRDKNVLLCLEERDWDPGLAIIDNLMQSINQSKKTVFVLTKKYAKSWNFKTAF
YLALQRLMDENMDVIIFILLEPVLQHSQYLRLRQRICKSSILQWPDNPKAEGLFWQTLRN
VVLTENDSRYNNMYVDSIKQY

<1041 residues, 0 stop; molecular weight: 119856.26

FIG. 3

><cDNA starts here>GGGTACCATTCTGCGCTGCTGCAAGTTACGGAATGAAAAATTAGAACAACAGA
AAC
><MET {trans=1-s, dir=f, res=1}>
ATGGAAAACATGTTCCTTCAGTCGTCAATGCTGACCTGCATTTTCCTGCTAATATCTGGT
TCCTGTGAGTTATGCGCCGAAGAAAATTTTCTAGAAGCTATCCTTGTGATGAGAAAAAG
CAAAATGACTCAGTTATTGCAGAGTGCAGCAATCGTCGACTACGACGGAAGTTCCCCAAACG
GTGGGCAAATATGTGACAGAAACTAGACCTGTCTGATAATTTCATCACACACATAACGAAT
GAATCATTTCAAGGCTGCAAAATCTCACTAAAATAAATCAAATGGCTTGAATATCACAGACGGGGCA
CAGCACCAGAACGAAATCCCGGTATACAAGGGAGTTACTGCTTGAAGACAACCAGTTACCCCAAATA
TTCCTCAACCTAAAAAAACCTAAGGGAGTTCTTTGACAGAACTTAGTCTAATTCAAAACAATATATACAAC
CCCTCGGTTTGCCAGAGTCTTTGCCAGAGTCTTTTGAAAAATCTCTATTTGGCCTGGAAC
ATAACTAAAGAGGGCATTTCAAGTTTGCGAGAAACTAACATAGAAGATGGAGTATTTGAAACGCTG
TGCTATTTTAACAAAGTTGCTATCACTACTTTTTCAATTCTCTTTTCACACGTGCCACCCAAACTG
ACAAATTTGGAGTTGCTATCACTACTTTTTCAATTCTCTTTTCACACGTGCCACCCAAACTG
CCAAGCTCCCTACGCAAACTTTTCTGAGCAACACCAGATCAAATACATTAGTGAAGAA
GATTTCAAGGATTGATAAATTAACATTACTAGAGATTTAAGCGGGAACTGCTCCGAGGTGC
TTCAATGCCCCATTTCAACTTGACCCAACTTGCTGTGATGGTGCTTCAATTAATATAGATCGT
TTGCTTTTCAAATTGACCCAACTTGCTGTGATGGTGCTTCAATTAATATAGATCGT
AAGATTAAATGCTGCCTGGTTAAAAAAATGCCTCATCTGAAGGTGCTGGATCTTGAATTC
AACTATTAGTGGGAGAAATAGTCTCTGGGCATTTTAACGATGCTGCCCCGCTTAGAA
ATACTTGACTTGTCTTTTAACTATATAAAGGGGAGTTATCCACAGCATATTAATATTTCC
AGAAACTTCTCTAAACTTTTGTCTCTACGGGCATTGCAGCTTAAGAGGTTATGTGTTCCAG
GAACTCAGAGAAGATGATTTTATTAAGCAAATCGATTTCAAACTTTTCAAAATTTCTCCAATCTG
TTGGGTATTAATTTATTAAGCAAATCGATTTCAAACTTTTCAAAATTTCTCCAATCTG

FIG. 4A

GAAATTATTACTTGTCAGAAAACAGAATATCACCGTTGGTAAAAGATACCCGGCAGAGT
TATGCAAATAGTTCCTCTTTTCAACGTCATATCCGGAAACGACGCTCAACAGATTTGAG
TTTGACCCACATTCGAACTTTATCATTTCACCCGTCCTTAATAAAGCCACAATGTGCT
GCTTATGGAAAAGCCTTAGATTTAAGCCTCAACAGTATTTCTTCATTGGGCCAAACCAA
TTTGAAAATCTTCCTGACATTGCCTGTGTTTAAATCTGTCTGCAAATAGCAATGCTCAAGTG
TTAAGTGGAACTGAATTTTCAGCCATTCCTCATGTCAAATATTTGGATTTGACAAACAAT
AGACTAGACTTTGATAATGCTAGTGCTCTTACTGAATTGTCCGACTTGGAAGTTCTAGAT
CTCAGCTATAATTCACACTATTTCAGAATAGCAGGCGTAACACATCATCTAGAATTTATT
CAAAATTTCACAAATCTAAAAGTTTAAACTTGAGCCACAACAACATTTATACTTTAACA
GATAAGTATAACCTGGAAAGCAAGTCCCTGGTAGAATTAGTTTTCAGTGGCAATCGCCTT
GACATTTGTGGAATGATGACAAGCAAGTATATCTCCATTTCAAAGGTCTCAAGAAT
CTGACACGTCTGGATTTATCCCTTAATAGGCTGAAGCACATCCCAAATGAAGCATTCCTT
AATTTGCCAGCGAGTCTCACTGAACTACATAAAAGATAATATGTTAAAGTTTTTTAAC
TGGACATTACTCCAGCAGTTTCCCTGAGTTACATCTTCCCTTCGACTTGCTTACGTGGAAACAAACTA
CTCTTTTTAACTGATAGCCTATCTGACTTCTGGCTTTCTTTCTGAAGTCAGTAGTCTGAAGCAC
CATAACAGGATTTCCCACCTACCCTCTGCTAAAAACATCAACAAATCCGCACTAAGACC
CTCGATTTAAGTTCCAATCTATGTTGGAACTACACGGAAACCCCTTTGAATGCACCTGTGACATT
ACCACCAAATTATCTATGTTGGAACATCTGAATGTCAAAATTCCAGACTGGTAGAT
GGAGATTTCCGAAGATGGATGATGAACATCTGAATGTCAAAATTCCAGACTGGTAGAT
GTCATTGTGCCAGTCCTGGGGATCAAAGAGGAAGAGTATTGTGAGTCTGGAGCTAACA
ACTTGTGTTTCAGATGTCACTGCAGTCCACCATTGTTTTACTGGGATGTTTGGTTTATATAT
ATGGTTATGTGTTGGCTGCCCTGCCACCATTGTTTTACTGGGATGTTTGGTTTATATAT
AATGTGTGTTTAGCTAAGGTAAAAGGCTACAGGTCTCTTTCCACATCCCAAACTTTCTAT
GATGCTTACATTTCTTATGACACCAAAGATGCCTCGTTACTGACTGGGTGATAAATGAG

FIG. 4B

Sequence ss.DNA42663

CTGCGCTACCACCCTTGAAGAGAGCCGAGACAAAAACGTTCTCCTTTGTCTAGAGGAGAGG
GATTGGGACCCGGGATTGGCCATCATCGACAACTTCATGCAGAGCATCAACCAAAGCAAG
AAAACAGTATTTGTTTTAACCAAAAAATATGCAAAAAGCTGGAACTTTAAAACAGCTTTT
TACTTGGCTTTGCAGAGGCTAAATGGATGAGAACATGGATGTGATTATATTATCCTGCTG
GAGCCAGTGTTACAGCATTCTCAGTATTTGAGGCTACGGCCAGCGGATCTGTAAGAGCTC
ATCCTCCAGTGCCTGACAACCCGAAGGCAGAAGGCTTGTTTTGGCAAACTCTGAGAAAT
GTGGTCTTTGACTGAAAATGATTCACGGTATAACAATATGTGTCGATTCCATTAAGCAA
TACTAACTGACGTTAAGTCATGATTTCGCGCCATAATATCCCAAAACTTAGTGTTTAAACAA
CTGTATTAGTTATCTATTGCTATGTAACAAATTATCCCAAAACTTAGTGTTTAAAACAA
CACATTGCTGGCCCACAGTTTTGAGGGTCAGGAGTCCAGGCCCAGCATAACTGGGTCC
TCTGCTCAGGGTGTCTCAGAGGCTGCAATGTAGGTGTTCAATTCCTCCTGGGCTATTGGCCAAAGG
GGGGTCACACTCATGTGGTTTGTTTTCTGGATTCAATTCCTCCTGGGCTATTGGCCAAAGG
CTATACTCATGTAAGCCATGCGAGCCTCTCCCACAAGGCAGCTTGCTTCATCAGAGCTAG
CAAAAGAGAGGTTGCTAGCAAGATGAAGTCACAATCTTTTGTAATCGAATCAAAAAG
TGATATCTCATCACTTTGGCCATATCCAGTCCCATATTCTATTGTTAGAAGTAAACCACAGTCCCACCAG
CTCCATGGAGTGACCACCTCAGTCCAGGAAAACAGCTGAAGACCAAGATGGTGAGCTC
TGATTGCTTCAGTTGGTCATCAACTATTTCCCTGACTGCTGTCCTGGGATGGCCTGCT
ATCTTGATGATAGATTGTGAATATCAGGAGGCAGGGATCACTTTTGCCACTGTGACTAATGGTCCT
TGACCTAACACATCTCTTCTTTCAATATCTAAGAACTTTTGCCACTGTGACTAATGGTCCT
AATATTAAGCTGTGTGTTTTATATTTATCATAATATCTATGGCTACATGGTTATATTATGCTG
TGGTTGCGTTCGGTTTATTTACAGTTGCTTTTACAAATATTGCTGTAACATTGACTT
CTAAGGTTTAGATGCCATTAAGAACTGAAGATGGATAGCTTTTAAAGCATCTTTACTTC
TTACCATTTTTAAAAGTATGCAGCTAAATTCGAAGCTTTTGGTCTATATTGTTAATTGC
CATTGCTGTAAATCTTAAAATGAATGAATAAAAATGTTTCATTTTACAAAAAAAAAAA
AAA

FIG. 4C

```
GTTATGCCTAGAAAACATTTCTCAAGAATTAGAATTACGATATGCTGTCAAACACAATGA
CTTATTTGAACCTCTTTTATTTGTAGGTTGAAGCACTGGACAATGCCACATACTTTGTGG
ATGGTGTGGGTCTTGGGGGTCATCATCAGCCTCTCCAAGGAAGAATCCTCCAATCAGGCT
TCTCTGTCTTGTGACCGCAATGGTATCTGCAAGGGCAGCTCAGGATCTTTAAACTCCATT
CCCTCAGGGCTCACAGAAGCTGTAAAAAGCCTTGACCTGTCCAACAACAGGATCACCTAC
ATTAGCAACAGTGACCTACAGAGGTGTGTGAACCTCCAGGCTCTGGTGCTGACATCCAAT
GGAATTAACACAATAGAGGAAGATTCTTTTCTTCCTGGGCAGTCTTGAACATTTAGAC
TTATCCTATAATTACTTATCTAATTTATCGTCTTCCTGGTTCAAGCCCCTTTCTTCTTTA
ACATTCTTAAACTTACTGGGAAATCCTTACAAAACCCTAGGGGAAACATCTCTTTTTTCT
CATCTCACAAAATTGCAAATCCTGAGAGTGGGAAATATGGACACCTTCACTAAGATTCAA
AGAAAAGATTTTGCTGGACTTACCTTCCTTGAGGAACTTGAGATTGATGCTTCAGATCTA
CAGAGCTATGAGCCAAAAAGTTTGAAGTCAATTCAGAATGTAAGTCATCTGATCCTTCAT
ATGAAGCAGCATATTTTACTGCTGGAGATTTTGTAGATGTTACAAGTTCCGTGGAATGT
TTGGAACTGCGAGATACTGATTTGGACACTTTCCATTTTTCAGAACTATCCACTGGTGAA
ACAAATTCATTGATTAAAAAGTTTACATTTAGAAATGTGAAAATCACCGATGAAAGTTTG
TTTCAGGTTATGAAACTTTTGAATCAGATTTCTGGATTGTTAGAATTAGAGTTTGATGAC
TGTACCCTTAATGGAGTTGGTAATTTTAGAGCATCTGATAATGACAGAGTTATAGATCCA
GGTAAAGTGGAAACGTTAACAATCCGGAGGCTGCATATTCCAAGGTTTTACTTATTTAT
GATCTGAGCACTTTATATTCACTTACAGAAAGAGTTAAAAGAATCACAGTAGAAAACAGT
AAAGTTTTTCTGGTTCCTTGTTTACTTTCACAACATTTAAAATCATTAGAATACTTGGAT
CTCAGTGAAAATTTGATGGTTGAAGAATACTTGAAAAATTCAGCCTGTGAGGATGCCTGG
CCCTCTCTACAAACTTTAATTTTAAGGCAAAATCATTTGGCATCATTGGAAAAAACCGGA
GAGACTTTGCTCACTCTGAAAAACTTGACTAACATTGATATCAGTAAGAATAGTTTTCAT
TCTATGCCTGAAACTTGTCAGTGGCCAGAAAAGATGAAATATTTGAACTTATCCAGCACA
CGAATACACAGTGTAACAGGCTGCATTCCCAAGACACTGGAAATTTTAGATGTTAGCAAC
AACAATCTCAATTTATTTTCTTTGAATTTGCCGCAACTCAAAGAACTTTATATTTCCAGA
AATAAGTTGATGACTCTACCAGATGCCTCCCTCTTACCCATGTTACTAGTATTGAAAATC
AGTAGGAATGCAATAACTACGTTTTCTAAGGAGCAACTTGACTCATTTCACACACTGAAG
ACTTTGGAAGCTGGTGGCAATAACTTCATTTGCTCCTGTGAATTCCTCTCCTTCACTCAG
GAGCAGCAAGCACTGGCCAAAGTCTTGATTGATTGGCCAGCAAATTACCTGTGTGACTCT
CCATCCCATGTGCGTGGCCAGCAGGTTCAGGATGTCCGCCTCTCGGTGTCGGAATGTCAC
AGGACAGCACTGGTGTCTGGCATGTGCTGTGCTCTGTTCCTGCTGATCCTGCTCACGGGG
GTCCTGTGCCACCGTTTCCATGGCCTGTGGTATATGAAATGATGTGGGCCTGGCTCCAG
GCCAAAAGGAAGCCCAGGAAAGCTCCCAGCAGGAACATCTGCTATGATGCATTTGTTTCT
TACAGTGAGCGGGATGCCTACTGGGTGGAGAACCTTATGGTCCAGGAGCTGGAGAACTTC
AATCCCCCCTTCAAGTTGTGTCTTCATAAGCGGGACTTCATTCCTGGCAAGTGGATCATT
GACAATATCATTGACTCCATTGAAAAGAGCCACAAAACTGTCTTTGTGCTTTCTGAAAAC
TTTGTGAAGAGTGAGTGGTGCAAGTATGAACTGGACTTCTCCCATTTCCGTCTTTTTGAT
GAGAACAATGATGCTGCCATTCTCATTCTTCTGGAGCCCATTGAGAAAAAGCCATTCCC
CAGCGCTTCTGCAAGCTGCGGAAGATAATGAACACCAAGACCTACCTGGAGTGGCCCATG
GACGAGGCTCAGCGGGAAGGATTTTGGGTAAATCTGAGAGCTGCGATAAAGTCCTAGGTT
CCCATATTTAAGACCAGTCTTTGTCTAGTTGGGATCTTTATGTCACTAGTTATAGTTAAG
TTCATTCAGACATAATTATATAAAAACTACGTGGATGTACCGTCATTTGAGGACTTGCTT
ACTAAAACTACAAAACTTCAAA
```

FIG. 10

```
MPHTLWMVWVLGVIISLSKEESSNQASLSCDRNGICKGSSGSLNSIPSGLTEAVKSLDL
SNNRITYISNSDLQRCVNLQALVLTSNGINTIEEDSFSSLGSLEHLDLSYNYLSNLSSS
WFKPLSSLTFLNLLGNPYKTLGETSLFSHLTKLQILRVGNMDTFTKIQRKDFAGLTFLE
ELEIDASDLQSYEPKSLKSIQNVSHLILHMKQHILLLEIFVDVTSSVECLELRDTDLDT
FHFSELSTGETNSLIKKFTFRNVKITDESLFQVMKLLNQISGLLELEFDDCTLNGVGNF
RASDNDRVIDPGKVETLTIRRLHIPRFYLFYDLSTLYSLTERVKRITVENSKVFLVPCL
LSQHLKSLEYLDLSENLMVEEYLKNSACEDAWPSLQTLILRQNHLASLEKTGETLLTLK
NLTNIDISKNSFHSMPETCQWPEKMKYLNLSSTRIHSVTGCIPKTLEILDVSNNNLNLF
SLNLPQLKELYISRNKLMTLPDASLLPMLLVLKISRNAITTFSKEQLDSFHTLKTLEAG
GNNFICSCEFLSFTQEQQALAKVLIDWPANYLCDSPSHVRGQQVQDVRLSVSECHRTAL
VSGMCCALFLLILLTGVLCHRFHGLWYMKMMWAWLQAKRKPRKAPSRNICYDAFVSYSE
RDAYWVENLMVQELENFNPPFKLCLHKRDFIPGKWIIDNIIDSIEKSHKTVFVLSENFV
KSEWCKYELDFSHFRLFDENNDAAILILLEPIEKKAIPQRFCKLRKIMNTKTYLEWPMD
EAQREGFWVNLRAAIKS
```

FIG. 11

(SEQ ID NO: 1)

| | | | | | | | | | | | | | | |
|---|---|---|---|---|---|---|---|---|---|---|---|---|---|---|
|Met|Arg|Leu|Ile|Arg|Asn|Ile|Tyr|Ile|Phe|Cys|Ser|Ile|Val|Met|Thr|Ala|Glu|Gly|Asp|Ala|Pro|Glu|Leu|Pro|Glu|Glu|Arg|Glu|Leu|
|1| | | |5| | | | |10| | | | |15| | | | |20| | | | |25| | | | |30|
|Met|Thr|Asn|Cys|Ser|Asn|Met|Ser|Leu|Arg|Lys|Val|Pro|Ala|Asp|Leu|Thr|Pro|Ala|Thr|Thr|Leu|Asp|Leu|Ser|Tyr|Asn|Leu|Leu|
| | | | |35| | | | |40| | | | |45| | | | |50| | | | |55| | | | |60|
|Phe|Gln|Leu|Gln|Ser|Ser|Asp|Phe|His|Ser|Val|Ser|Lys|Leu|Arg|Val|Leu|Ile|Leu|Cys|His|Asn|Arg|Ile|Gln|Gln|Leu|Asp|Leu|Lys|
| | | | |65| | | | |70| | | | |75| | | | |80| | | | |85| | | | |90|
|Thr|Phe|Glu|Phe|Asn|Lys|Glu|Leu|Arg|Tyr|Leu|Asp|Leu|Ser|Asn|Asn|Arg|Leu|Lys|Ser|Val|Thr|Trp|Tyr|Leu|Leu|Ala|Gly|Leu|Arg|
| | | | |95| | | | |100| | | | |105| | | | |110| | | | |115| | | | |120|
|Tyr|Leu|Asp|Leu|Ser|Phe|Asn|Asp|Phe|Asp|Thr|Met|Pro|Ile|Cys|Glu|Glu|Ala|Gly|Asn|Met|Ser|His|Leu|Glu|Ile|Leu|Gly|Leu|Ser|
| | | | |125| | | | |130| | | | |135| | | | |140| | | | |145| | | | |150|
|Gly|Ala|Lys|Ile|Gln|Lys|Ser|Asp|Phe|Gln|Lys|Ile|Ala|His|Leu|His|Leu|Asn|Thr|Val|Phe|Leu|Gly|Phe|Arg|Thr|Leu|Pro|His|Tyr|
| | | | |155| | | | |160| | | | |165| | | | |170| | | | |175| | | | |180|
|Glu|Gly|Ser|Leu|Pro|Ile|Leu|Asn|Thr|Lys|Leu|His|Ile|Val|Leu|Pro|Met|Asp|Thr|Asn|Phe|Trp|Val|Leu|Leu|Arg|Asp|Gly|
| | | | |185| | | | |190| | | | |195| | | | |200| | | | |205| | | | |210|
|Ile|Lys|Thr|Ser|Lys|Ile|Leu|Glu|Met|Thr|Asn|Ile|Asp|Gly|Lys|Ser|Gln|Phe|Val|Ser|Tyr|Glu|Met|Gln|Arg|Asn|Leu|Ser|Leu|Glu|
| | | | |215| | | | |220| | | | |225| | | | |230| | | | |235| | | | |240|
|Asn|Ala|Lys|Thr|Ser|Val|Leu|Leu|Leu|Asn|Lys|Val|Asp|Leu|Leu|Trp|Asp|Asp|Leu|Phe|Leu|Ile|Leu|Gln|Phe|Val|Trp|His|Thr|Ser|
| | | | |245| | | | |250| | | | |255| | | | |260| | | | |265| | | | |270|

FIG. 12A

```
Val Glu His Phe Gln Ile Arg Asn Val Thr Phe Gly Gly Lys Ala Tyr Leu Asp His Asn Ser Phe Asp Tyr Ser Asn Thr Val Met Arg
                275             280             285             290             295             300

Thr Ile Lys Leu Glu His Val His Phe Arg Val Phe Tyr Ile Gln Asp Lys Ile Tyr Leu Leu Thr Lys Met Asp Ile Glu Asn
                305             310             315             320             325             330

Leu Thr Ile Ser Asn Ala Gln Met Pro His Met Leu Phe Pro Asn Tyr Pro Thr Lys Phe Gln Tyr Leu Asn Phe Ala Asn Asn Ile Leu
                335             340             345             350             355             360

Thr Asp Glu Leu Phe Lys Arg Thr Ile Gln Leu Pro His Leu Lys Thr Leu Ile Leu Asn Gly Asn Lys Leu Glu Thr Leu Ser Leu Val
                365             370             375             380             385             390

Ser Cys Phe Ala Asn Asn Thr Pro Leu Glu His Leu Asp Leu Ser Gln Asn Leu Leu Gln His Lys Asn Asp Ser Cys Ser Trp Pro
                395             400             405             410             415             420

Glu Thr Val Val Asn Met Asn Leu Ser Tyr Asn Lys Leu Thr Lys Glu Thr Ile His Leu Met Ala Leu Arg Glu Leu Asn Ile Ala Phe
                425             430             435             440             445             450

Asn Asn Gln Ile Gln Thr Val Pro Lys Glu Thr Ile His Leu Met Ala Leu Arg Glu Leu Asn Ile Ala Phe Asn Phe Leu Thr Asp
                455             460             465             470             475             480

Leu Pro Gly Cys Ser His Phe Ser Arg Leu Ser Val Leu Asn Ile Glu Met Asn Phe Ile Leu Ser Pro Ser Leu Asp Phe Val Gln Ser
                485             490             495             500             505             510

Cys Gln Glu Val Lys Thr Leu Asn Ala Gly Arg Asn Pro Phe Arg Cys Thr Cys Glu Leu Lys Asn Phe Ile Gln Leu Glu Thr Tyr Ser
                515             520             525             530             535             540
```

FIG. 12B

Glu Val Met Met Val Gly Trp Ser Asp Ser Tyr Thr Cys Glu Tyr Pro Leu Asn Leu Arg Gly Thr Arg Leu Lys Asp Val His Leu His
                545                 550                 555                 560                 565                 570

Glu Leu Ser Cys Asn Thr Ala Leu Leu Ile Val Thr Ile Val Val Ile Met Leu Val Val Leu Gly Leu Ala Val Ala Phe Cys Cys Leu His
                575                 580                 585                 590                 595                 600

Phe Asp Leu Pro Trp Tyr Leu Arg Met Leu Gly Gln Cys Thr Gln Thr Trp His Arg Val Arg Lys Thr Thr Gln Glu Gln Leu Lys Arg
                605                 610                 615                 620                 625                 630

Asn Val Arg Phe His Ala Phe Ile Ser Tyr Ser Glu His Asp Ser Leu Trp Val Lys Asn Glu Leu Ile Pro Asn Leu Glu Lys Glu Asp
                635                 640                 645                 650                 655                 660

Gly Ser Ile Leu Ile Cys Leu Tyr Glu Ser Tyr Phe Asp Pro Gly Lys Ser Ile Ser Glu Asn Ile Val Ser Phe Ile Glu Lys Ser Tyr
                665                 670                 675                 680                 685                 690

Lys Ser Ile Phe Val Leu Ser Pro Asn Phe Val Gln Asn Glu Trp Cys His Tyr Glu Phe Tyr Phe Ala His His Asn Leu Phe His Glu
                695                 700                 705                 710                 715                 720

Asn Ser Asp His Ile Ile Ile Leu Leu Glu Pro Ile Pro Phe Tyr Cys Ile Pro Thr Arg Tyr His Lys Leu Lys Ala Leu Leu Glu
                725                 730                 735                 740                 745                 750

Lys Lys Ala Tyr Leu Glu Trp Pro Lys Asp Arg Arg Lys Cys Gly Leu Phe Trp Ala Asn Leu Arg Ala Ala Ile Asn Val Asn Val Leu
                755                 760                 765                 770                 775                 780

Ala Thr Arg Glu Met Tyr Glu Leu Gln Thr Phe Thr Glu Leu Asn Glu Glu Ser Arg Gly Ser Thr Ile Ser Leu Met Arg Thr Asp Cys
                785                 790                 795                 800                 805                 810

Leu
811

FIG. 12C (SEQ ID NO: 2)

```
GAATCATCCA CGCACCTGCA GCTCTGCTGA GAGAGTGCAA GCCCGTGGGG TTTTGAGCTC ATCTTCATCA TTCATATGAG GAAATAAGTG GTAAAATCCT    100
          <MET (trans=1-s, dir=f, res+1)>
TGGAAATACA ATGAGACTCA TCAGAAACAT TTACATATTT TGTAGTATTG TTATGACAGC AGAGGGTGAT GCTCCAGAGC TGCCAGAAGA AAGGGAACTG    200
ATGACCAACT GCTCCAACAT GTCTCTAAGA AAGGTTCCCG CAGACTTGAC CCCAGCCACA ACGACACTGG ATTTATCCTA TAACCTCCTT TTTCAACTCC    300
AGAGTTCAGA TTTTCATTCT GTCTCCAAAC TGAGAGTTTT GATTCTATGC CATAACAGAA TTCAACAGCT GGATCTCAAA ACCTTTGAAT TCAACAAGAA    400
GTTAAGATAT TTAGATTTGT CTAATAACAG ACTGAAGAGT GTAACTTGGT ATTTACTGGC AGTCTCAGG TATTTAGATC TTTCTTTTAA TGACTTTGAC    500
ACCATGCCTA TCTGTGAGGA AGCTGGCAAC ATGTCACACC TGGAAATCCT TACAAAAATC CTTAAACACA AGATTCCAG AAAATTGCTC    600
ATCTGCATCT AAATACTGTC TTCTTAGGAT TCCTCATTAT GAAGAAGGTA GCCTGCCCAT CAAAAATATT TACTCTGGGA CGACCTTTTC CTTATCTTAC    700
ACCAATGGAC ACAAATTTCT GGGTTCTTTT GCGTGATGAA ATCAAGACTT CAAAAATATT AAGTTGATT TTTGCTTAAT ACTCAAATAC ACATTGTTTT    800
TATGAAATGC AACGAAATCT TAGTTTAGAA AATGCTAAGA CATCGGTTCT ATTGCTTAAT AAAGTTGATT TACTCTGGGA CGACCTTTTC CTTATCTTAC    900
AATTTGTTTG GCATACATCA GTGGAACACT TTCAGATCCG AAATGTGACT TTTGGTGGTA AGGCTTATCT TGACCACAAT TCATTTGACT ACTCAAATAC    1000
TGTAATGAGA ACTATAAAAT TGGAGCATGT ACATTTCAGA GTGTTTTACA TTCAACAGAA TAAAATCTAT TTGCTTTTGA CCAAAATGGA CATAGAAAAC    1100
CTGACAATAT CAAATGCACA AATGCCACAC ATGCTTTTCC CGAATTATCC TACGAAATTC CAATATTTAA ATTTTGCCAA TAATATCTTA ACAGACGAGT    1200
TGTTTAAAAG AACTATCCAA CTGCCTCACT TGAAAACTCT CATTTTGAAT GGCAATAAAC TGGAGACACT TTCTTTAGTA AGTTGCTTTG CTAACAACAC    1300
ACCCTTGGAA CACTTGGATC TGAGTCAAAA TCTATTACAA CATAAAAATG ATGAAAATTG CTCATGGCCA GAAACTGTGG TCAATATGAA TCTGTCATAC    1400
AATAAATTGT CTGATTCTGT CTTCAGGTGC TTGCCCAAAA GTATTCAAAT ACTTGACCTA AATAATAACC AAATCCAAAC TGTACCTAAA GAGACTATTC    1500
ATCTGATGGC CTTACGAGAA CTAAATATTG CATTTAATTT TCTAACTGAT CTCCCTGGAT GCAGTCATTT CAGTAGACTT TCAGTTCTGA ACATTGAAAT    1600
GAACTTCATT CTCAGCCCAT CTCTGGATTT TGTTCAGAGC TGCCAGGAAG TTAAAACTCT AAATGCGGGA AGAAATCCAT TCCGGTGTAC CTGTGAATTA    1700
AAAATTTCA TTCAGCTTGA AACATATTCA GAGGTCATGA GTCAGATTCA TACACCTGTG AATACCCTTT AAACCTAAGG GGAACTAGGT    1800
```

FIG. 13A

```
TAAAAGAGACGT TCATCTCCAC GAATTATCTT GCAACACAGC TCTGTTTGATT GTCACCATTG TGGTTATTAT GCTAGTTCTG GGGTTGGCTG TGGCCTTCTG   1900
CTGTCTCCAC TTTGATCTGC CCTGGTATCT CAGGATGCTA GGTCAATGCA CACAAACATG GCACAGGGTT AGGAAAACAA CCCAAGAACA ACTCAAGAGA   2000
AATGTCCGAT TCCACGCATT TATTTCATAC AGTGAACATG ATTCTCTGTG GGTGAAGAAT CCAATCTAGA GAAGGAAGAT GGTTCTATCT   2100
TGATTTGCCT TTATGAAAGC TACTTTTGACC CTGGCAAAAG CATTAGTGAA GCTTCATTGA GAAAAGCTAT AAGTCCATCT TTGTTTTGTC   2200
TCCCAACTTT GTCCAGAATG AGTGGTGCCA TTATGAATTC TACTTTGCCC ACCACAATCT CTTCCATGAA AATTCTGATC ATATAATTCT TATCTTACTG   2300
GAACCCATTC CATTCTATTG CATTCCCACC AGTATCATA AACTGAAAGC TCTCCTGGAA AAAAAAGCAT ACTTGGAATG GCCCAAGGAT AGGCGTAAAT   2400
GTGGGCTTTT CTGGGCAAAC CTTCGAGCTG CTATTAATGT TAATGTATTA GCCACCAGAG AAATGTATGA ACTGCAGACA TTCACAGAGT TAAATGAAGA   2500
GTCTCGAGGT TCTACAATCT CTCTGATGAG AACAGATTGT CTA [TAA] AATC CCACAGTCCT TGGGAAGTTG GGGACCACAT ACACTGTTGG GATGTACATT   2600
GATACAACCT TTATGATGGC AATTTGACAA TATTTATTAA AATAAAAAAT GGTTATTCCC TTTCATATCAG GATTTCTAAG AATGTATCCT   2700
ATAGAAACAC CTTCACAAGT TTATAAGGGC TTATATGAAA AGTGTTCAT CCCAGGATTG TTTATAAATCA TGAAAAATGT GGCCAGGTGC AGTGGCTCAC   2800
TCTTGTAATC CCAGCACTAT GGGAGGCCAA GGTGGGTGAC CCACGAGGTC AAGAGATGGA GACCATCCTG GCCAACATGG TGAAACCCTG TCTCTACTAA   2900
AAATACAAAA ATTAGCTGGG CGTGATGGTG CACGCCTGTA GTCCCAGCTA CTTGGGAGGC TGAGGCAGGA GAATCGCTTG AACCCGGGAG GTGGCAGTTG   3000
CAGTGAGCTG AGATCGAGCC ACTGCACTCC AGCCTGGTGA CAGAGCGAGA CTCCATCTCA AAAAAAAAGAA AAAAAAAAAA GAAAAAAATG GAAAACATCC   3100
TCATGGCCAC AAAATAAGGT CTAATTCAAT AAATTATAGT ACATTAATGT AATATAATAT TAAAAAGAAT AAGTAGCTG TATATTTCCT   3200
GGTATGGAAA AAACATATTA AACTATTAGG TTGGTGCAAA ACTAATTGTG TTTTTGCCA TTGAAATGGC ATGAAATAA AAGTGTAAAG   3300
AAATCTATAC CAGATGTAGT AACAGTGGTT TGGGTCTGGG AGGTTGGATT ACAGGGGAGCA TTTGATTCT ATGTTGTGTA TTCTCTATAAT GTTTGAATTG   3400
TTTAGAATGA ATCTGTATTT CTTTTATAAG TAGAAAAAAA ATAAAGATAG TTTTTACAGC CT   3462
```

FIG. 13B

ANTIBODIES THAT BIND TO PRO286

RELATED APPLICATIONS

This application is a continuation of U.S. patent application Ser. No. 09/202,054 filed Dec. 7, 1998, now U.S. Pat. No. 7,696,327 which is a Section 371 application of PCT/US98/21141 filed Oct. 7, 1998, claiming priority to provisional applications 60/062,250 filed Oct. 17, 1997; 60/065,311 filed Nov. 13, 1997; 60/083,322 filed Apr. 28, 1998; 60/090,863 filed Jun. 26, 1998; and 09/105,413 filed Jun. 26, 1998, the contents of which are incorporated herein by reference.

FIELD OF THE INVENTION

The present invention relates generally to the identification and isolation of novel DNAs designated herein as DNA40021, DNA42663 and DNA47361, and to the recombinant production of novel human Toll homologues (designated as PRO285, PRO286 and PRO358, respectively) encoded by said DNAs.

BACKGROUND OF THE INVENTION

Membrane-bound proteins and receptors can play an important role in the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interaction. The membrane-bound proteins can also be employed for screening of potential peptide or small molecule inhibitors of the relevant receptor/ligand interaction.

Efforts are being undertaken by both industry and academia to identify new, native receptor proteins. Many efforts are focused on the screening of mammalian recombinant DNA libraries to identify the coding sequences for novel receptor proteins.

The cloning of the Toll gene of *Drosophila*, a maternal effect gene that plays a central role in the establishment of the embryonic dorsal-ventral pattern, has been reported by Hashimoto et al., *Cell* 52, 269-279 (1988). The *Drosophila* Toll gene encodes an integral membrane protein with an extracytoplasmic domain of 803 amino acids and a cytoplasmic domain of 269 amino acids. The extracytoplasmic domain has a potential membrane-spanning segment, and contains multiple copies of a leucine-rich segment, a structural motif found in many transmembrane proteins. The Toll protein controls dorsal-ventral patterning in *Drosophila* embryos and activates the transcription factor Dorsal upon binding to its ligand Spätzle. (Morisato and Anderson, *Cell* 76, 677-688 (1994).) In adult *Drosophila*, the Toll/Dorsal signaling pathway participates in the anti-fungal immune response. (Lenaitre et al., *Cell* 86, 973-983 (1996).)

A human homologue of the *Drosophila* Toll protein has been described by Medzhitov et al., *Nature* 388, 394-397 (1997). This human Toll, just as *Drosophila* Toll, is a type I transmembrane protein, with an extracellular domain consisting of 21 tandemly repeated leucine-rich motifs (leucine-rich region—LRR), separated by a non-LRR region, and a cytoplasmic domain homologous to the cytoplasmic domain of the human interleukin-1 (IL-1) receptor. A constitutively active mutant of the human Toll transfected into human cell lines was shown to be able to induce the activation of NF-κB and the expression of NF-κB-controlled genes for the inflammatory cytokines IL-1, IL-6 and IL-8, as well as the expression of the constimulatory molecule B7.1, which is required for the activation of native T cells. It has been suggested that Toll functions in vertebrates as a non-clonal receptor of the immune system, which can induce signals for activating both an innate and an adaptive immune response in vertebrates. The human Toll gene reported by Medzhitov et al., supra was most strongly expressed in spleen and peripheral blood leukocytes (PBL), and the authors suggested that its expression in other tissues may be due to the presence of macrophages and dendritic cells, in which it could act as an early-warning system for infection. The public GenBank database contains the following Toll sequences: Toll1 (DNAX# HSU88540-1, which is identical with the random sequenced full-length cDNA #HUMRSC786-1); Toll2 (DNAX# HSU88878-1); Toll3 (DNAX# HSU88879-1); and Toll4 (DNAX# HSU88880-1, which is identical with the DNA sequence reported by Medzhitov et al., supra). A partial Toll sequence (Toll5) is available from GenBank under DNAX# HSU88881-1.

Further human homologues of the *Drosophila* Toll protein, designated as Toll-like receptors (huTLRs1-5) were recently cloned and shown to mirror the topographic structure of the *Drosophila* counterpart (Rock et al., *Proc. Natl. Acad. Sci. USA* 95, 588-593 [1998]). Overexpression of a constitutively active mutant of one human TLR (Toll-protein homologue-Medzhitov et al., supra; TLR4—Rock et al., supra) leads to the activation of NF-κB and induction of the inflammatory cytokines and constimulatory molecules. Medzhitov et al., supra.

SUMMARY OF THE INVENTION

Applicants have identified three novel cDNA clones that encode novel human Toll polypeptides, designated in the present application as PRO285 (encoded by DNA40021), PRO286 (encoded by DNA42663), and PRO358 (encoded by DNA47361).

In one embodiment, the invention provides an isolated nucleic acid molecule comprising a DNA encoding a polypeptide having at least about 80% sequence identity, preferably at least about 85% sequence identity, more preferably at least about 90% sequence identity, most preferably at least about 95% sequence identity to (a) a DNA molecule encoding a PRO285 polypeptide having amino acid residues 27 to 839 of FIG. 1 (SEQ ID NO:1); or (b) to a DNA molecule encoding a PRO286 polypeptide having amino acid residues 27 to 825 of FIG. 3 (SEQ ID NO:3), or (c) to a DNA molecule encoding a PRO358 polypeptide having amino acids 20 to 575 of FIGS. 12A-C (SEQ ID NO: 13), or (d) the complement of the DNA molecule of (a), (b), or (c). The complementary DNA molecule preferably remains stably bound to such encoding nucleic acid sequence under at least moderate, and optionally, under high stringency conditions.

In a further embodiment, the isolated nucleic acid molecule comprises a polynucleotide that has at least about 90%, preferably at least about 95% sequence identity with a polynucleotide encoding a polypeptide comprising the sequence of amino acids 1 to 839 of FIG. 1 (SEQ ID NO:1); or at least about 90%, preferably at least about 95% sequence identity with a polynucleotide encoding a polypeptide comprising the sequence of amino acids 1 to 1041 of FIG. 3 (SEQ ID NO: 3); or at least about 90%, preferably at least about 95% sequence identity with a polynucleotide encoding a polypeptide comprising the sequence of amino acids 1 to 811 of FIGS. 12A-C (SEQ ID NO: 13).

In a specific embodiment, the invention provides an isolated nucleic acid molecule comprising DNA encoding native or variant PRO285, PRO286, and PRO358 polypeptides, with or without the N-terminal signal sequence, and with or without the transmembrane regions of the respective full-length sequences. In one aspect, the isolated nucleic acid comprises DNA encoding a mature, full-length native PRO285, PRO286, or PRO358 polypeptide having amino acid residues 1 to 1049 of FIG. 1 (SEQ ID NO: 1), 1 to 1041 of FIG. 3 (SEQ ID NO: 3), and 1 to 811 of FIGS. 12A-C (SEQ ID NO: 13), or is complementary to such encoding nucleic acid sequence. In another aspect, the invention concerns an isolated nucleic acid molecule that comprises DNA encoding a native PRO285, PRO286, or PRO358 polypeptide without an N-terminal signal sequence, or is complementary to such encoding nucleic acid sequence. In yet another embodiment, the invention concerns nucleic acid encoding transmembrane-domain deleted or inactivated forms of the full-length native PRO285, PRO286 and PRO358 proteins.

In another aspect, the invention concerns an isolated nucleic acid molecule encoding a PRO285, PRO286 or PRO358 polypeptide comprising DNA hybridizing to the complement of the nucleic acid between about residues 85 and about 3283 inclusive, of FIG. 2 (SEQ ID NO: 2), or to the complement of the nucleic acid between about residues 57 and about 4199, inclusive, of FIG. 4 (SEQ ID NO: 4), or to the complement of the nucleic acid between about residues 111 and about 2544 of FIGS. 13A-B (SEQ ID NO: 14). Preferably, hybridization occurs under stringent hybridization and wash conditions.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 to 1049, inclusive of FIG. 1 (SEQ ID NO:1), or amino acid residues 1 to 1041, inclusive of FIG. 3 (SEQ ID NO: 3), or amino acid residues 1 to 811, inclusive of FIGS. 12A-C (SEQ ID NO: 13, or (b) the complement of a DNA of (a).

In another embodiment, the invention the isolated nucleic acid molecule comprises the clone (DNA 40021-1154) deposited on Oct. 17, 1997, under ATCC number 209389; or the clone (DNA 42663-1154) deposited on Oct. 17, 1997, under ATCC number 209386; or the clone (DNA 47361-1249) deposited on Nov. 7, 1997, under ATCC number 209431.

In yet another embodiment, the invention provides a vector comprising DNA encoding PRO285, PRO286 and PRO358 polypeptides, or their variants. Thus, the vector may comprise any of the isolated nucleic acid molecules hereinabove defined.

In a specific embodiment, the invention provides a vector comprising a polynucleotide having at least about 80% sequence identity, preferably at least about 85% sequence identity, more preferably at least about 90% sequence identity, most preferably at least about 95% sequence identity with a polynucleotide encoding a polypeptide comprising the sequence of amino acids 20 to 811 of FIGS. 12A-C (SEQ ID NO:13), or the complement of such polynucleotide. In a particular embodiment, the vector comprises DNA encoding the novel Toll homologue (PRO358), with or without the N-terminal signal sequence (about amino acids 1 to 19), or a transmembrane-domain (about amino acids 576-595) deleted or inactivated variant thereof, or the extracellular domain (about amino acids 20 to 595) of the mature protein, or a protein comprising any one of these sequences. A host cell comprising such a vector is also provided. A similar embodiment will be apparent for vectors comprising polynucleotides encoding the PRO285 and PRO286 Toll homologues, with our without the respective signal sequences and/or transmembrane-domain deleted or inactivated variants thereof, and specifically, vectors comprising the extracellular domains of the mature PRO85 and PRO286 Toll homologues, respectively.

A host cell comprising such a vector is also provided. By way of example, the host cells may be CHO cells, *E. coli*, or yeast.

A process for producing PRO285, PRO286 and PRO358 polypeptides is further provided and comprises culturing host cells under conditions suitable for expression of PRO285, PRO286, and PRO358, respectively, and recovering PRO285, PRO286, o PRO358 from the cell culture.

In another embodiment, the invention provides isolated PRO285, PRO286 and PRO358 polypeptides. In particular, the invention provides isolated native sequence PRO285 and PRO286 polypeptides, which in one embodiment, include the amino acid sequences comprising residues 1 to 1049 and 1 to 1041 of FIGS. 1 and 3 (SEQ ID NOs:1 and 3), respectively. The invention also provides for variants of the PRO285 and PRO286 polypeptides which are encoded by any of the isolated nucleic acid molecules hereinabove defined. Specific variants include, but are not limited to, deletion (truncated) variants of the full-length native sequence PRO285 and PRO286 polypeptides which lack the respective N-terminal signal sequences and/or have their respective transmembrane and/or cytoplasmic domains deleted or inactivated. The invention further provides an isolated native sequence PRO358 polypeptide, or variants thereof. In particular, the invention provides an isolated native sequence PRO358 polypeptide, which in certain embodiments, includes the amino acid sequence comprising residues 20 to 575, or 20 to 811, or 1 to 811 of FIGS. 12A-C (SEQ ID NO: 13).

In a further aspect, the invention concerns an isolated PRO285, PRO286 or PRO358 polypeptide, comprising an amino acid sequence scoring at least about 80% positives, preferably at least about 85% positives, more preferably at least about 90% positives, most preferably at least about 95% positives when compared with the amino acid sequence of amino acid residues 1 to 1049, inclusive of FIG. 1 (SEQ ID NO:1), or amino acid residues 1 to 1041, inclusive of FIG. 3 (SEQ ID NO: 3), or amino acid residues 1 to 811, inclusive of FIGS. 12A-C (SEQ ID NO: 13).

In a still further aspect, the invention provides a polypeptide produced by (I) hybridizing a test DNA molecule under stringent conditions with (a) a DNA molecule encoding a PRO285, PRO286 or PRO358 polypeptide having the sequence of amino acid residues from about 1 to about 1049, inclusive of FIG. 1 (SEQ ID NO:1), or amino acid residues from about 1 to about 1041, inclusive of FIG. 3 (SEQ ID NO: 3), or amino acid residues from about 1 to about 811, inclusive of FIGS. 12A-C (SEQ ID NO: 13), or (b) the complement of a DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In another embodiment, the invention provides chimeric molecules comprising PRO285, PRO286, or PRO358 polypeptides fused to a heterologous polypeptide or amino acid sequence. An example of such a chimeric molecule comprises a PRO285, PRO286, or PRO358 polypeptide fused to an epitope tag sequence or a Fc region of an immunoglobulin. An example of such a chimeric molecule comprises a PRO358 polypeptide (including its signal peptide and/or transmembrane-domain and, optionally, intracellular domain, deleted variants), fused to an epitope tag sequence or a Fc region of an immunoglobulin. In a preferred embodiment, the fusion contains the extracellular domain of PRO358 fused to an immunoglobulin constant region, comprising at least the CH2 and CH3 domains. Similar specific embodiments exist and are disclosed herein for chimeric molecules comprising a PRO285 or PRO286 polypeptide.

In another embodiment, the invention provides an antibody which specifically binds to PRO285, PRO286 or PRO358 polypeptides. Optionally, the antibody is a monoclonal antibody. The invention specifically includes antibodies with dual specificities, e.g., bispecific antibodies binding more than one Toll polypeptide.

In yet another embodiment, the invention concerns agonists and antagonists of the native PRO285, PRO286 and PRO358 polypeptides. In a particular embodiment, the agonist or antagonist is an anti-PRO285, anti-PRO286 or anti-PRO358 antibody.

In a further embodiment, the invention concerns screening assays to identify agonists or antagonists of the native PRO285, PRO286 and PRO358 polypeptides.

In a still further embodiment, the invention concerns a composition comprising a PRO285, PRO286 or PRO358 polypeptide, or an agonist or antagonist as hereinabove defined, in combination with a pharmaceutically acceptable carrier.

The invention further concerns a composition comprising an antibody specifically binding a PRO285, PRO286 or PRO358 polypeptide, in combination with a pharmaceutically acceptable carrier.

The invention also concerns a method of treating septic shock comprising administering to a patient an effective amount of an antagonist of a PRO285, PRO286 or PRO358 polypeptide. In a specific embodiment, the antagonist is a blocking antibody specifically binding a native PRO285, PRO286 or PRO358 polypeptide.

BRIEF DESCRIPTION OF THE DRAWINGS

FIG. 1 shows the derived amino acid sequence of a native sequence human Toll protein, designated PRO285 (SEQ ID NO: 1).

FIG. 2 shows the nucleotide sequence of a native sequence human Toll protein cDNA designated DNA40021 (SEQ ID NO: 2), which encodes PRO285.

FIG. 3 shows the derived amino acid sequence of a native sequence human Toll protein, designated PRO286 (SEQ ID NO: 3).

FIG. 4 shows the nucleotide sequence of a native sequence human Toll protein cDNA designated DNA42663 (SEQ ID NO: 4), which encodes PRO286.

FIG. 10 Nucleotide sequence encoding huTLR2 (SEQ ID NO:11).

FIG. 11 Amino acid sequence of huTLR2 (SEQ ID NO:12).

FIGS. 12A-C show the derived amino acid sequence of a native sequence human Toll protein, designated PRO358 (SEQ ID NO: 13). In the Figure, amino acids 1 through 19 form a putative signal sequence, amino acids 20 through 575 are the putative extracellular domain, with amino acids 20 through 54 having the characteristics of leucine rich repeats, amino acids 576 through 595 are a putative transmembrane domain, whereas amino acids 596 through 811 form an intracellular domain.

FIGS. 13A-B (SEQ ID NO: 14) show the nucleotide sequence of a native sequence human Toll protein cDNA designated DNA47361, which encodes the mature, full-length Toll protein, PRO358. As the sequence shown contains some extraneous sequences, the ATG start codon is underlined, and the TAA stop codon is boxed.

DETAILED DESCRIPTION OF THE PREFERRED EMBODIMENTS

I. Definitions

Figure 5A:
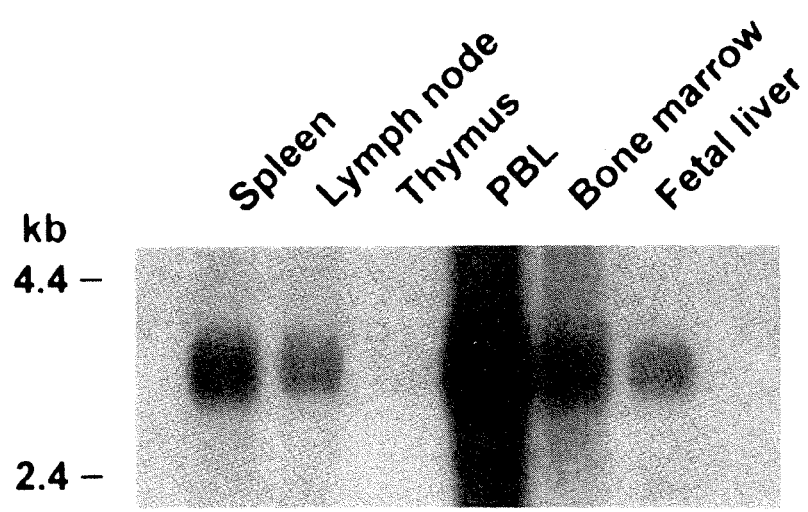
FIG. 5 shows the expression pattern of human Toll receptor 2 (huTLR2) (Rock et al., supra). a. Northern analysis of human multiple immune tissues probed with a TLR2 probe. PBL, peripheral blood leukocytes. b. Enriched expression of TLR2 in macrophages, and transcriptional up-regulation of TLR2 in response to LPS. Quantitative RT-PCR was used to determined the relative expression levels of TLR2 in PBL, T cells, macrophages (MΦ), and LPS-stimulated macrophages (MΦ+LPS).

The terms "PRO285 polypeptide", "PRO286 polypeptide", "PRO285" and "PRO286", when used herein, encompass the native sequence PRO285 and PRO286 Toll proteins and variants (which are further defined herein). The PRO285 and PRO286 polypeptide may be isolated from a variety of sources, such as from human tissue types or from another source, or prepared by recombinant or synthetic methods, or by any combination of these and similar techniques.

A "native sequence PRO285" or "native sequence PRO286" comprises a polypeptide having the same amino acid sequence as PRO285 or PRO286 derived from nature. Such native sequence Toll polypeptides can be isolated from nature or can be produced by recombinant or synthetic means. The terms "native sequence PRO285" and "native sequence PRO286" specifically encompass naturally-occurring truncated or secreted forms of the PRO285 and PRO286 polypeptides disclosed herein (e.g., an extracellular domain sequence), naturally-occurring variant forms (e.g., alternatively spliced forms) and naturally-occurring allelic variants of the PRO285 and PRO286 polypeptides. In one embodiment of the invention, the native sequence PRO285 is a mature or full-length native sequence PRO285 polypeptide comprising amino acids 1 to 1049 of FIG. 1 (SEQ ID NO: 1), while native sequence PRO286 is a mature or full-length native sequence PRO286 polypeptide comprising amino acids 1 to 1041 of FIG. 3 (SEQ ID NO:3). In a further embodiment, the native sequence PRO285 comprises amino acids 27-1049, or 27-836 of FIG. 1 (SEQ ID NO:1), or amino acids 27-1041, or 27-825 of FIG. 3 (SEQ ID NO:3).

The terms "PRO285 variant" and "PRO286 variant" mean an active PRO285 or PRO286 polypeptide as defined below having at least about 80% amino acid sequence identity with PRO285 having the deduced amino acid sequence shown in FIG. 1 (SEQ ID NO:1) for a full-length native sequence PRO285, or at least about 80% amino acid sequence identity with PRO286 having the deduced amino acid sequence shown in FIG. 3 (SEQ ID NO:3) for a full-length native sequence PRO286. Such variants include, for instance, PRO285 and PRO286 polypeptides wherein one or more amino acid residues are added, or deleted, at the N- or C-terminus of the sequences of FIGS. 1 and 3 (SEQ ID NO: 1 and 3), respectively. Ordinarily, a PRO285 or PRO286 variant will have at least about 80% amino acid sequence identity, more preferably at least about 90% amino acid sequence identity, and even more preferably at least about 95% amino acid sequence identity with the amino acid sequence of FIG. 1 or FIG. 3 (SEQ ID NOs:1 and 3). Preferred variants are those which show a high degree of sequence identity with the extracellular domain of a native sequence PRO285 or PRO286 polypeptide. In a special embodiment, the PRO285 and PRO286 variants of the present invention retain at least a C-terminal portion of the intracellular domain of the corresponding native proteins, and most preferably they retain most of the intracellular and the extracellular domains. However, depending on their intended use, such variants may have various amino acid alterations, e.g., substitutions, deletions and/or insertions within these regions.

The terms "PRO358 polypeptide", "PRO358", "PRO358 Toll homologue" and grammatical variants thereof, as used herein, encompass the native sequence PRO358 Toll protein and variants (which are further defined herein). The PRO358 polypeptide may be isolated from a variety of sources, such as from human tissue types or from another source, or prepared by recombinant or synthetic methods, or by any combination of these and similar techniques.

A "native sequence PRO358" comprises a polypeptide having the same amino acid sequence as PRO358 derived from nature. Such native sequence Toll polypeptides can be isolated from nature or can be produced by recombinant or synthetic means. The term "native sequence PRO358" specifically encompasses naturally-occurring truncated or secreted forms of the PRO358 polypeptide disclosed herein (e.g., an extracellular domain sequence), naturally-occurring variant forms (e.g., alternatively spliced forms) and naturally-occurring allelic variants. In one embodiment of the invention, the native sequence PRO358 is a mature or full-length native sequence PRO358 polypeptide comprising amino acids 20 to 811 of FIGS. 12A-C (SEQ ID NO: 13), with or without the N-terminal signal sequence (amino acids 1 to 19), and with or without the N-terminal methionine. In another embodiment, the native sequence PRO358 is the soluble form of the full-length PRO358, retaining the extracellular domain of the full-length protein (amino acids 29 to 575), with or without the N-terminal signal sequence, and with or without the N-terminal methionine.

The term "PRO358 variant" means an active PRO358 polypeptide as defined below having at least about 80%, preferably at least about 85%, more preferably at least about 90%, most preferably at least about 95% amino acid sequence identity with PRO358 having the deduced amino acid sequence shown in FIGS. 12A-C (SEQ ID NO:13). Such variants include, for instance, PRO358 polypeptides wherein one or more amino acid residues are added, or deleted, at the N- or C-terminus of the sequences of FIGS. 12A-C (SEQ ID NO:13). Variants specifically include transmembrane-domain deleted and inactivated variants of native sequence PRO358, which may also have part or whole of their intracellular domain deleted. Preferred variants are those which show a high degree of sequence identity with the extracellular domain of the native sequence PRO358 polypeptide. In a special embodiment, the PRO358 variants of the present invention retain at least a C-terminal portion of the intracellular domain of a corresponding native protein, and most preferably they retain most of the intracellular and the extracellular domains. However, depending on their intended use, such variants may have various amino acid alterations, e.g., substitutions, deletions and/or insertions within these regions.

"Percent (%) amino acid sequence identity" with respect to the PRO285, PRO286 and PRO358 sequences identified herein is defined as the percentage of amino acid residues in a candidate sequence that are identical with the amino acid residues in the PRO285, PRO286, or PRO358 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. The ALIGN software is preferred to determine amino acid sequence identity.

In a specific aspect, "percent (%) amino acid sequence identity" with respect to the PRO285, PRO286 and PRO358 sequences identified herein is defined as the percentage of amino acid residues in a candidate sequence that are identical with the amino acid residues in the PRO285, PRO286 and PRO358 sequence, after aligning the sequences and introducing gaps, if necessary, to achieve the maximum percent sequence identity, and not considering any conservative substitutions as part of the sequence identity. The % identity values used herein are generated by WU-BLAST-2 which was obtained from [Altschul et al., *Methods in Enzymology*, 266: 460-480 (1996); http://blast.wustl/edu/blast/README-.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

"Percent (%) nucleic acid sequence identity" with respect to the DNA40021, DNA42663 and DNA47361 sequences identified herein is defined as the percentage of nucleotides in a candidate sequence that are identical with the nucleotides in the DNA40021, DNA42663 and DNA47361 sequences, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. The ALIGN software is preferred to determine nucleic acid sequence identity.

Specifically, "percent (%) nucleic acid sequence identity" with respect to the coding sequence of the PRO285, PRO286 and PRO358 polypeptides identified herein is defined as the percentage of nucleotide residues in a candidate sequence that are identical with the nucleotide residues in the PRO285, PRO286 and PRO358 coding sequence. The identity values used herein were generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO285, PRO286, or PRO358 natural environment will not be present. Ordinarily, however, isolated polypeptide will be prepared by at least one purification step.

An "isolated" DNA40021, DNA42663 or DNA47361 nucleic acid molecule is a nucleic acid molecule that is identified and separated from at least one contaminant nucleic acid molecule with which it is ordinarily associated in the natural source of the DNA40021, DNA42663 or DNA47361 nucleic acid. An isolated DNA40021, DNA42663 or DNA47361 nucleic acid molecule is other than in the form or setting in which it is found in nature. Isolated DNA40021, DNA42663 and DNA47361 nucleic acid molecules therefore are distinguished from the DNA40021, DNA42663 or DNA47361 nucleic acid molecule as it exists in natural cells. However, an isolated DNA40021, DNA42663 or DNA47361 nucleic acid molecule includes DNA40021, DNA42663 and DNA47361 nucleic acid molecules contained in cells that ordinarily express DNA40021, DNA42663 or DNA47361 where, for example, the nucleic acid molecule is in a chromosomal location different from that of natural cells.

"Toll receptor2", "TLR2" and "huTLR2" are used interchangeably, and refer to a human Toll receptor designated as "HuTLR2" by Rock et al., *Proc. Natl. Acad. Sci. USA* 95, 588-593 (1998). The nucleotide and amino acid sequences of huTLR2 are shown in FIGS. 10 (SEQ ID NO: 11) and 11 (SEQ ID NO: 12), respectively.

The term "expression vector" is used to define a vector, in which a nucleic acid encoding a Toll homologue protein herein is operably linked to control sequences capable of affecting its expression is a suitable host cells. Vectors ordinarily carry a replication site (although this is not necessary where chromosomal integration will occur). Expression vectors also include marker sequences which are capable of providing phenotypic selection in transformed cells. For example, E. coli is typically transformed using pBR322, a plasmid derived from an E. coli species (Bolivar, et al., Gene 2: 95 [1977]). pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible; even powerful constitutive promoters such as the CMV promoter for mammalian hosts have been found to produce the LHR without host cell toxicity. While it is conceivable that expression vectors need not contain any expression control, replicative sequences or selection genes, their absence may hamper the identification of hybrid transformants and the achievement of high level hybrid immunoglobulin expression.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-PRO285, anti-PRO286 and anti-PRO358 monoclonal antibodies (including agonist, antagonist, and neutralizing antibodies) and anti-PRO285, anti-PRO286 and anti-PRO358 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "antagonist" is used in the broadest sense, and includes any molecule that partially or fully blocks, prevents, inhibits, or neutralizes a biological activity of a native Toll receptor disclosed herein. In a similar manner, the term "agonist" is used in the broadest sense and includes any molecule that mimics, or enhances a biological activity of a native Toll receptor disclosed herein. Suitable agonist or antagonist molecules specifically include agonist or antagonist antibodies or antibody fragments, fragments or amino acid sequence variants of native Toll receptor polypeptides, peptides, small organic molecules, etc.

"Active" or "activity" for the purposes herein refers to form(s) of PRO285, PRO286 and PRO358 which retain the biologic and/or immunologic activities of native or naturally-occurring PRO285, PRO286 and PRO358, respectively. A preferred "activity" is the ability to induce the activation of NF-κB and/or the expression of NF-κB-controlled genes for the inflammatory cytokines IL-1, IL-6 and IL-8. Another preferred "activity" is the ability to activate an innate and/or adaptive immune response in vertebrates. A further preferred "activity" is the ability to sense the presence of conserved molecular structures present on microbes, and specifically the ability to mediate lipopolysaccharide (LPS) signaling. The same "activity" definition applies to agonists (e.g. agonist antibodies) of PRO285, PRO286 and PRO358 polypeptides. As noted above, the "activity" an antagonist (including agonist antibodies) of a PRO285, PRO286 or PRO358 polypeptide is defined as the ability to counteract, e.g. partially or fully block, prevent, inhibit, or neutralize any of the above-identified activities of a PRO285, PRO286 or PRO358 polypeptide.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology* (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a FIZZ polypeptide fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cor-cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and the immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

The term "lipopolysaccharide" or "LPS" is used herein as a synonym of "endotoxin." Lipopolysaccharides (LPS) are characteristic components of the outer membrane of Gram-negative bacteria, e.g., *Escherichia coli*. They consist of a polysaccharide part and a fat called lipid A. The polysaccharide, which varies from one bacterial species to another, is made up of the O-specific chain (built from repeating units of three to eight sugars) and the two-part core. Lipid A virtually always includes two glucosamine sugars modified by phosphate and a variable number of fatty acids. For further information see, for example, Rietschel and Brade, *Scientific American* August 1992, 54-61.

The term "septic shock" is used herein in the broadest sense, including all definitions disclosed in Bone, *Ann. Intern Med.* 114, 332-333 (1991). Specifically, septic shock starts with a systemic response to infection, a syndrome called sepsis. When this syndrome results in hypotension and organ dysfunction, it is called septic shock. Septic shock may be initiated by gram-positive organisms and fungi, as well as endotoxin-containing Gram-negative organisms. Accordingly, the present definition is not limited to "endotoxin shock."

II. Compositions and Methods of the Invention

A. Full-Length PRO285, PRO286 and PRO358

The present invention provides newly identified and isolated nucleotide sequences encoding, polypeptides referred to in the present application as PRO285 and PRO286 In particular, Applicants have identified and isolated cDNAs encoding PRO285 and PRO286 polypeptides, as disclosed in further detail in the Examples below. Using BLAST and FastA sequence alignment computer programs, Applicants found that the coding sequences of PRO285 and PRO286 are highly homologous to DNA sequences HSU88540_1, HSU88878_1, HSU88879_1, HSU88880_1, and HSU88881_1 in the GenBank database.

The present invention further provides newly identified and isolated nucleotide sequences encoding a polypeptide referred to in the present application as PRO358. In particular, Applicants have identified and isolated cDNA encoding a novel human Toll polypeptide (PRO358), as disclosed in further detail in the Examples below. Using BLAST and FastA sequence alignment computer programs, Applicants found that the coding sequence of PRO358 shows significant homology to DNA sequences HSU88540_1, HSU88878_1, HSU88879_1, HSU88880_1, HS88881_1, and HSU79260_1 in the GenBank database. With the exception of HSU79260_1, the noted proteins have been identified as human toll-like receptors.

Accordingly, it is presently believed that the PRO285, PRO286 and PRO358 proteins disclosed in the present application are newly identified human homologues of the *Drosophila* protein Toll, and are likely to play an important role in adaptive immunity. More specifically, PRO285, PRO286 and PRO358 may be involved in inflammation, septic shock, and response to pathogens, and play possible roles in diverse medical conditions that are aggravated by immune response, such as, for example, diabetes, ALS, cancer, rheumatoid arthritis, and ulcers. The role of PRO285, PRO286 and PRO385 as pathogen pattern recognition receptors, sensing the presence of conserved molecular structures present on microbes, is further supported by the data disclosed in the present application, showing that a known human Toll-like receptor, TLR2 is a direct mediator of LPS signaling.

B. PRO285. PRO286 and PRO358 Variants

In addition to the full-length native sequence PRO285, PRO286 and PRO358 described herein, it is contemplated that variants of these sequences can be prepared. PRO285, PRO286 and PRO358 variants can be prepared by introducing appropriate nucleotide changes into the PRO285, PRO286 or PRO358 DNA, or by synthesis of the desired variant polypeptides. Those skilled in the art will appreciate that amino acid changes may alter post-translational processes of the PRO285, PRO286 or PRO358 polypeptides, such as changing the number or position of glycosylation sites or altering the membrane anchoring characteristics.

Variations in the native full-length sequence PRO285, PRO286 or PRO358, or in various domains of the PRO285, PRO286, or PRO358 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO285, PRO286, or PRO358 polypeptide that results in a change in the amino acid sequence as compared with the corresponding native sequence polypeptides. Optionally the variation is by substitution of at least one amino acid with any other amino acid in one or more of the domains of the PRO285, PRO286, or PRO358. Guidance in determining which amino acid residue may be inserted, substituted or deleted without adversely affecting the desired activity may be found by comparing the sequence of the PRO285, PRO286, or PRO358 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO285 or PRO286 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isoteric amino acid can be used.

Variants of the PRO285, PRO286 and PRO358 Toll proteins disclosed herein include proteins in which the transmembrane domains have been deleted or inactivated. Transmembrane regions are highly hydrophobic or lipophilic domains that are the proper size to span the lipid bilayer of the cellular membrane. They are believed to anchor the native, mature PRO285, PRO286 and PRO358 polypeptides in the cell membrane. In PRO285 the transmembrane domain stretches from about amino acid position 840 to about amino acid position 864. In PRO286 the transmembrane domain is between about amino acid position 826 and about amino acid position 848. In PRO358 the transmembrane domain is between about amino acid position 576 and amino acid position 595.

Deletion or substitution of the transmembrane domain will facilitate recovery and provide a soluble form of a PRO285, PRO286, and PRO358 polypeptide by reducing its cellular or membrane lipid affinity and improving its water solubility. If the transmembrane and cytoplasmic domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of a transmembrane domain deleted PRO285, PRO286 or PRO358 is that it is secreted into the culture medium of recombinant hosts. This variant is soluble in body fluids such as blood and does not have an appreciable affinity for cell membrane lipids, thus considerably simplifying its recovery from recombinant cell culture.

It will be amply apparent from the foregoing discussion that substitutions, deletions, insertions or any combination thereof are introduced to arrive at a final construct. As a general proposition, soluble variants will not have a functional transmembrane domain and preferably will not have a functional cytoplasmic sequence. This is generally accomplished by deletion of the relevant domain, although adequate insertional or substitutional variants also are effective for this purpose. For example, the transmembrane domain is substituted by any amino acid sequence, e.g. a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) PRO285, PRO286 and PRO358 variants, these variants are secreted into the culture medium of recombinant hosts.

Further deletional variants of the full-length mature PRO285, PRO286, and PRO358 polypeptides (or transmembrane domain deleted to inactivated forms thereof) include variants from which the N-terminal signal peptide (putatively identified as amino acids 1 to 19 for PRO285 and PRO286, and as amino acids 1 to 26 for PRO358) and/or the initiating methionine has been deleted. The native signal sequence may also be substituted by another (heterologous) signal peptide, which may be that of another Toll-like protein, or another human or non-human (e.g., bacterial, yeast or non-human mammalian) signal sequence.

It is believed that the intracellular domain, and especially its C-terminal portion, is important for the biological function of these polypeptides. Accordingly, if the objective is to make variants which retain the biological activity of a corresponding native Toll-like protein, at least a substantial portion of these regions is retain, or the alterations, if any, involve conservative amino acid substitutions and/or insertions or amino acids which are similar in character to those present in the region where the amino acid is inserted. If, however, a substantial modification of the biological function of a native Toll receptor is required (e.g., the objective is to prepare antagonists of the respective native Toll polypeptides), the alterations involve the substitution and/or insertion of amino acids, which differ in character from the amino acid at the targeted position in the corresponding native Toll polypeptide.

Naturally-occurring amino acids are divided into groups based on common side chain properties:
(1) hydrophobic: norleucine, met, ala, val, leu, ile;
(2) neutral hydrophobic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Variants obtained by non-conservative substitutions are expected to result in more significant changes in the biological properties/function of the obtained variant.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the PRO285, PRO286 or PRO358 protein amino acid sequence) may range generally from about 1 to 10 residues, more preferably 1 to 5 residues, more preferably 1 to 3 residues. Examples of terminal insertions include the PRO285, PRO286 and PRO358 polypeptides with an N-terminal methionyl residue, an artifact of its direct expression in bacterial recombinant cell culture, and fusion of a heterologous N-terminal signal sequence to the N-terminus of the PRO285, PRO286, or PRO358 molecule to facilitate the secretion of the mature I-TRAF proteins from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells.

Other insertional variants of the native Toll-like molecules disclosed herein include the fusion of the N- or C-terminus of the native sequence molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions to yield immunoadhesins), albumin, or ferritin, as described in WO 89/02922 published on 6 Apr. 1989. For the production of immunoglobulin fusions see also U.S. Pat. No. 5,428,130 issued Jun. 27, 1995.

Since it is often difficult to predict in advance the characteristics of a variant Toll-like protein, it will be appreciated that screening will be needed to select the optimum variant. For this purpose biochemical or other screening assays, such as those described hereinbelow, will be readily available.

C. Modifications of the PRO285, PRO286 and PRO358 Toll Proteins

Covalent modifications of the PRO285, PRO286 and PRO358 human Toll homologues are included within the scope of this invention. One type of covalent modification includes reacting targeted amino acid residues of the PRO285, PRO286 or PRO358 protein with an organic derivatizing agent that is capable of reacting with selected side chains or the N- or C-terminal residues. Derivatization with bifunctional agents is useful, for instance, for crosslinking PRO285, PRO286, or PRO358 to a water-insoluble support matrix or surface for use in the method for purifying anti-PRO285-PRO286, or -PRO358 antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Derivatization with bifunctional agents is useful for preparing intramolecular aggregates of the Toll-like receptors herein with polypeptides as well as for cross-linking these polypeptides to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Another type of covalent modification of the PRO285, PRO286 and PRO358 polypeptides included within the scope of this invention comprises altering the native glycosylation pattern of the polypeptide. "Altering the native glycosylation pattern" is intended for purposes herein to mean deleting one or more carbohydrate moieties found in native sequence (either by removing the underlying glycosylation site or by deleting the glycosylation by chemical and/or enzymatic means) and/or adding one or more glycosylation sites that are not present in the native sequence. In addition, the phrase includes qualitative changes in the glycosylation of the native proteins, involving a change in the nature and proportions of the carbohydrates present.

The native, full-length PRO285 (encoded by DNA 40021) has potential N-linked glycosylation sites at the following amino acid positions: 66, 69, 167, 202, 215, 361, 413, 488, 523, 534, 590, 679, 720, 799 and 942. The native, full-length PRO286 (encoded by DNA42663) has potential N-linked glycosylation sites at the following amino acid positions: 29, 42, 80, 88, 115, 160, 247, 285, 293, 358, 362, 395, 416, 443, 511, 546, 582, 590, 640, 680, 752, 937 and 1026.

Addition of glycosylation sites to the PRO285, PRO286 and PRO358 polypeptides may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the PRO285, PRO286, and PRO358 polypeptides at preselected bases such that codons are generated that will translate into the desired amino acids.

Another means of increasing the number of carbohydrate moieties on the PRO285, PRO286 and PRO358 polypeptides is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO285, PRO286 and PRO358 polypeptides may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification comprises linking the PRO285, PRO286 and PRO358 polypeptides to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The PRO285, PRO286 and PRO358 polypeptides of the present invention may also be modified in a way to form a chimeric molecule comprising PRO285, PRO286, PRO358, or a fragment thereof, fused to another, heterologous polypeptide or amino acid sequence. In one embodiment, such a chimeric molecule comprises a fusion of the PRO285, PRO286 or PRO358 polypeptide with a tag polypeptide which provides an epitope to which an anti-tag antibody can selectively bind. The epitope tag is generally placed at the amino- or carboxyl-terminus of a native or variant PRO285, PRO286, or PRO358 molecule. The presence of such epitope-tagged forms can be detected using an antibody against the tag polypeptide. Also, provision of the epitope tag enables the PRO285, PRO286, or PRO358 polypeptides to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 3:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In a further embodiment, the chimeric molecule may comprise a fusion of the PRO285, PRO286 or PRO358 polypeptides, or fragments thereof, with an immunoglobulin or a particular region of an immunoglobulin. For a bivalent form of the chimeric molecule, such a fusion could be to the Fc region of an Ig, such as, IgG molecule. The Ig fusions preferably include the substitution of a soluble (transmembrane domain deleted or inactivated) form of a PRO285, PRO286, or PRO358 polypeptide in place of at least one variable region within an Ig molecule. For the production of immunoglobulin fusions see also U.S. Pat. No. 5,428,130 issued Jun. 27, 1995.

D. Preparation of PRO285, PRO286 and PRO358 Polypeptides

The description below relates primarily to production of PRO285, PRO286, and PRO358 Toll homologues by culturing cells transformed or transfected with a vector containing nucleic acid encoding these proteins (e.g. DNA40021, DNA42663, and DNA47361, respectively). It is, of course, contemplated that alternative methods, which are well known in the art, may be employed to prepare PRO285, PRO286, PRO358, or their variants. For instance, the PRO285, PRO286 or PRO358 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO285, PRO286, or PRO358 may be chemically synthesized separately and combined using chemical or enzymatic methods to produce the full-length PRO285, PRO286, or PRO358.

1. Isolation of DNA Encoding PRO285 PRO286 or PRO358

DNA encoding PRO285, PRO286, or PRO358 may be obtained from a cDNA library prepared from tissue believed to possess the PRO285, PRO286, or PRO358 mRNA and to express it at a detectable level. Accordingly, human PRO285, PRO286, or PRO358 DNA can be conveniently obtained from a cDNA library prepared from human tissue, such as described in the Examples. The underlying gene may also be obtained from a genomic library or by oligonucleotide synthesis. In addition to the libraries described in the Examples, DNA encoding the human Toll proteins of the present invention can be isolated, for example, from spleen cells, or peripheral blood leukocytes (PBL).

Libraries can be screened with probes (such as antibodies to the PRO285, PRO286, or PRO358 protein or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO285, PRO286, or PRO358 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology/sequence identity.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for the production of the human Toll proteins and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 2:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as K coli K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for human Toll-encoding vectors. *Saccharomyces cerevisiae* is a commonly used lower eukaryotic host microorganism Suitable host cells for the expression of glycosylated human Toll proteins are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/−DHFR (CHO, Urlaub and Chasin, Proc. Natl. Acad. Sci. USA, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO285, PRO286, or PRO358 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO285, PRO286 and PRO358 proteins may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO285, PRO286 or PRO358 DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO285, PRO286, or PRO358 nucleic acid, such as DHFR or thymidine kinase. An appropriate host cell when wild-type DHFR is employed is the CHO cell line deficient in DHFR activity, prepared and propagated as described by Urlaub et al., *Proc. Natl*, Acad. Sci. USA, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the nucleic acid sequence encoding the PRO285, PRO286 or PRO358 protein to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO285, PRO286, or PRO358.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO285, PRO286 or PRO358 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO285, PRO286, or PRO358 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO285, PRO286, or PRO358 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO285, PRO286, or PRO358.

Still other methods, vectors, and host cells suitable for adaptation to the synthesis of PRO285, PRO286, or PRO358 in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO285, PRO286 or PRO358 polypeptides or against a synthetic peptide based on the DNA sequences provided herein or against exogenous sequence fused to PRO285, PRO286 or PRO358 DNA and encoding a specific antibody epitope.

5. Purification of Polypeptide

Forms of PRO285, PRO286 or PRO358 may be recovered from culture medium or from host cell lysates. If membrane-bound, it can be released from the membrane using a suitable detergent solution (e.g. Triton-X 100) or by enzymatic cleavage. Cells employed in expression of PRO285, PRO286 or PRO358 can be disrupted by various physical or chemical means, such as freeze-thaw cycling, sonication, mechanical disruption, or cell lysing agents.

It may be desired to purify PRO285, PRO286, or PRO358 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the Toll proteins. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular Toll protein produced.

E. Uses for the Toll Proteins and Encoding Nucleic Acids

Nucleotide sequences (or their complement) encoding the Toll proteins of the present invention have various applications in the art of molecular biology, including uses as hybridization probes, in chromosome and gene mapping and in the generation of anti-sense RNA and DNA. Toll nucleic acid will also be useful for the preparation of PRO285, PRO286 and PRO358 polypeptides by the recombinant techniques described herein.

The full-length native sequence DNA40021, DNA42663, and DNA47361 genes, encoding PRO285, PRO286, and PRO358, respectively, or portions thereof, may be used as hybridization probes for a cDNA library to isolate the full-length gene or to isolate still other genes (for instance, those encoding naturally-occurring variants of PRO285, PRO286, or PRO358 or their further human homologues, or homologues from other species) which have a desired sequence identity to the PRO285, PRO286, or PRO358 sequence disclosed in FIGS. 1, 3 and 12A-B, respectively. Optionally, the length of the probes will be about 20 to about 50 bases. The hybridization probes may be derived from the nucleotide sequence of FIG. 2 (SEQ ID NO: 2), or FIG. 4 (SEQ ID NO: 4), or FIG. 13A-B (SEQ ID NO: 14), or from genomic sequences including promoters, enhancer elements and introns of native sequence. By way of example, a screening method will comprise isolating the coding region of the PRO285, or PRO286, or PRO358 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO285, PRO286, or PRO358 gene (DNAs 40021, 42663 and 47361) of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related Toll sequences.

Nucleotide sequences encoding a Toll protein herein can also be used to construct hybridization probes for mapping the gene which encodes that Toll protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

The human Toll proteins of the present invention can also be used in assays to identify other proteins or molecules involved in Toll-mediated signal transduction. For example, PRO285, PRO286, and PRO358 are useful in identifying the as of yet unknown natural ligands of human Tolls, or other factors that participate (directly or indirectly) in the activation of and/or signaling through a human Toll receptor, such as potential Toll receptor associated kinases. In addition, inhibitors of the receptor/ligand binding interaction can be identified. Proteins involved in such binding interactions can also be used to screen for peptide or small molecule inhibitors or agonists of the binding interaction. Screening assays can be designed to find lead compounds that mimic the biological activity of a native Toll polypeptide or a ligand for a native Toll polypeptide. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

In vitro assays employ a mixture of components including a Toll receptor polypeptide, which may be part of fusion product with another peptide or polypeptide, e.g., a tag for detecting or anchoring, etc. The assay mixtures may further comprise (for binding assays) a natural intra- or extracellular Toll binding target (i.e. a Toll ligand, or another molecule known to activate and/or signal through the Toll receptor). While native binding targets may be used, it is frequently preferred to use portion of such native binding targets (e.g. peptides), so long as the portion provides binding affinity and avidity to the subject Toll protein conveniently measurable in the assay. The assay mixture also contains a candidate pharmacological agent. Candidate agents encompass numerous chemical classes, through typically they are organic compounds, preferably small organic compounds, and are obtained from a wide variety of sources, including libraries of synthetic or natural compounds. A variety of other reagents may also be included in the mixture, such as, salts, buffers, neutral proteins, e.g. albumin, detergents, protease inhibitors, nuclease inhibitors, antimicrobial agents, etc.

In in vitro binding assays, the resultant mixture is incubated under conditions whereby, but for the presence of the candidate molecule, the Toll protein specifically binds the cellular binding target, portion or analog, with a reference binding affinity. The mixture components can be added in any order that provides for the requisite bindings and incubations may be performed at any temperature which facilitates optimal binding. Incubation periods are likewise selected for optimal binding but also minimized to facilitate rapid high-throughput screening.

After incubation, the agent-biased binding between the Toll protein and one or more binding targets is detected by any convenient technique. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for example, membrane filtration (e.g. Whatman's P-18 ion exchange paper, Polyfiltronic's hydrophobic GFC membrane, etc.), gel chromatography (e.g. gel filtration, affinity, etc.). For Toll-dependent transcription assays, binding is detected by a change in the expression of a Toll-dependent reporter.

Detection may be effected in any convenient way. For cell-free binding assays, one of the components usually comprises or is coupled to a label. The label may provide for direct detection as radioactivity, luminescence, optical or electron density, etc., or indirect detection, such as, an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

Nucleic acids which encode PRO285, PRO286, or PRO358, or their modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO285 or PRO286 can be used to clone genomic DNA encoding PRO285, PRO286, or PRO358 in accordance with established techniques and the genomic sequences used to generate transgenic animals that contain cells which express DNA encoding PRO285, PRO286, or PRO358. Methods for generating transgenic animals, particularly animals such as mice or rats, have become conventional in the art and are described, for example, in U.S. Pat. Nos. 4,736,866 and 4,870,009. Typically, particular cells would be targeted for transgene incorporation with tissue-specific enhancers. Transgenic animals that include a copy of a transgene encoding PRO285, PRO286, or PRO358 introduced into the germ line of the animal at an embryonic stage can be used to examine the effect of increased expression of DNA encoding PRO285, PRO286, or PRO358. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human vertebrate (e.g. mammalian) homologues of PRO285 or PRO286 or PRO358 can be used to construct a "knock out" animal which has a defective or altered gene encoding PRO285 or PRO286 or PRO358, as a result of homologous recombination between the endogenous gene encoding PRO285, PRO286, or PRO358 protein and altered genomic DNA encoding PRO285, PRO286, or PRO358 introduced into an embryonic cell of the animal. For example, cDNA encoding PRO285, PRO286, or PRO358 can be used to clone genomic DNA encoding PRO285, PRO286, or PRO358 in accordance with established techniques. A portion of the genomic DNA encoding PRO285, PRO286, or PRO358 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO285, PRO286, or PRO358 polypeptides.

Nucleic acid encoding the Toll polypeptide disclosed herein may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of the currently known gene marking and gene therapy protocols see Anderson et al., Science 256, 808-813 (1992).

The various uses listed in connection with the Toll proteins herein, are also available for agonists of the native Toll receptors, which mimic at least one biological function of a native Toll receptor.

F. Anti-Toll Protein Antibodies

The present invention further provides anti-Toll protein antibodies. Exemplary antibodies include polyclonal, monoclonal, humanized, bispecific, and heteroconjugate antibodies.

1. Polyclonal Antibodies

The anti-Toll protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO285 and PRO286 polypeptides or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-Toll protein antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO285, PRO286, or PRO358 polypeptides or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO285, PRO286, or PRO358. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized and Human Antibodies

The anti-Toll antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

4. Bispecific Antibodies

Bispecific antibodies are monoclonal, preferably human or humanized, antibodies that have binding specificities for at least two different antigens. In the present case, one of the binding specificities may be for the PRO285, PRO286, or PRO358 protein, the other one for any other antigen, and preferably for a cell-surface protein or receptor or receptor subunit. It is also possible to prepare bispecific antibodies, having specificities to two different Toll-like proteins, such as, any two of the Toll homologues disclosed in the present application, or a Toll protein disclosed herein, and a Toll protein known in the art, e.g., TLR2. Such bispecific antibodies could block the recognition of different pathogen patterns by Toll receptors, and are, therefore, expected to have significant benefits in the treatment of sepsis and septic shock.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-Toll Protein Antibodies

The anti-Toll antibodies of the invention have various utilities. For example, anti-PRO285, anti-PRO286, anti-PRO358, and anti-TLR2 antibodies may be used in diagnostic assays for PRO285, PRO286, PRO358, or TLR2 e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO285, anti-PRO286, anti-PRO358, or anti-TLR2 antibodies also are useful for the affinity purification of these proteins from recombinant cell culture or natural sources. In this process, the antibodies against these Troll proteins are immobilized on a suitable support, such a Sephadex resin or filter paper, using methods well known in the art. The immobilized antibody then is contacted with a sample containing the to be purified, and thereafter the support is washed with a suitable solvent that will remove substantially all the material in the sample except the PRO285, PRO286, PRO358, or TLR2 protein which is bound to the immobilized antibody.

Finally, the support is washed with another suitable solvent that will release the protein from the antibody.

Anti-Toll receptor (i.e., anti-PRO285, anti-PRO286, anti-PRO358, or anti-TLR2 antibodies) may also be useful in blocking the biological activities of the respective Toll receptors. The primary function of the family of Toll receptors is believed to be to act as pathogen pattern recognition receptors sensing the presence of conserved molecular pattern present on microbes. Lipopolysaccharides (LPS, also known as endotoxins), potentially lethal molecules produced by various bacteria, bind to the lipopolysaccharide binding protein (LBP) in the blood. The complex formed then activates a receptor known as CD14. There is no consensus in the art about what happens next. According to a hypothesis, CD14 does not directly instruct macrophages to produce cytokines, cell adhesion proteins and enzymes involved in the production of lower molecular weight proinflammatory mediators, rather enables LPS to activate a second receptor. Alternatively, it has been suggested that LPS may activate certain receptors directly, without help from LBP or CD14. The data disclosed in the present application indicate that the human toll-like receptors are signaling receptors that are activated by LPS in an LBP and CD14 responsive manner. As this mechanism, under pathophysiologic conditions can lead to an often fatal syndrome called septic shock, anti-Toll receptor antibodies (just as other Toll receptor antagonists) might be useful in the treatment of septic shock. It is foreseen that the different Toll receptors might recognize different pathogens, e.g., various strains of Gram-negative or Gram-positive bacteria. Accordingly, in certain situations, combination therapy with a mixture of antibodies specifically binding different Toll receptors, or the use of bispecific anti-Toll antibodies may be desirable.

It is specifically demonstrated herein that anti-huTLR2 antibodies are believed to be specifically useful in blocking the induction of this receptor by LPS. As it has been shown that LPS exposure can lead to septic shock (Parrillo, *N. Engl. J. Med.* 328, 1471-1477 [1993]), anti-huTLR2 antibodies are potentially useful in the treatment of septic shock.

The foregoing therapeutic and diagnostic uses listed in connection with the anti-Toll receptor antibodies are also applicable to other Toll antagonists, i.e., other molecules (proteins, peptides, small organic molecules, etc.) that block Toll receptor activation and/or signal transduction mediated by Toll receptors.

In view of their therapeutic potentials, the Toll proteins (including variants of the native Toll homologues), and their agonists and antagonists (including but not limited to anti-Toll antibodies) are incorporated in compositions suitable for therapeutic use. Therapeutic compositions are prepared for storage by mixing the active ingredient having the desired degree of purity with optional physiologically acceptable carriers, excipients or stabilizers (Remington's Pharmaceutical Sciences 16th Edition, Osol, A. Ed. 1980) in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences, supra.*

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et. al., *Biopolymers* 22 (1): 547-556 [1983]), poly (2-hydroxyethyl-methacrylate) (R. Langer, et al., *J. Biomed. Mater. Res.* 15: 167-277 [1981] and R. Langer, *Chem. Tech.* 12: 98-105 [1982]), ethylene vinyl acetate (R. Langer et al., Id.) or poly-D-(−)-3-hydroxybutyric acid (EP 133,988). Sustained release compositions also include liposomes. Liposomes containing a molecule within the scope of the present invention are prepared by methods known per se: DE 3,218, 121; Epstein et al., *Proc. Natl. Acad. Sci. USA* 82: 3688-3692 (1985); Hwang et al., *Proc. Natl. Acad. Sci, USA* 77: 4030-4034 (1980); EP 52322; EP 36676A; EP 88046; EP 143949; EP 142641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mol. % cholesterol, the selected proportion being adjusted for the optimal NT-4 therapy.

An effective amount of the active ingredient will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer a molecule of the present invention until a dosage is reached that provides the required biological effect. The progress of this therapy is easily monitored by conventional assays.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA Clones Encoding Human PRO285

A proprietary expressed sequence tag (EST) DNA database (LIFESEQ™, Incyte Pharmaceuticals, Palo Alto, Calif.) was searched and an EST (#2243209) was identified which showed homology to the *Drosophila* Toll protein.

Based on the EST, a pair of PCR primers (forward and reverse):

```
TAAAGACCCAGCTGTGACCG        (SEQ ID NO: 5)

ATCCATGAGCCTCTGATGGG,       (SEQ ID NO: 6)
```
and
a probe:

```
                                               (SEQ ID NO: 7)
ATTTATGTCTCGAGGAAAGGGACTGGTTACCAGGGCAGCCAGTTC
```
were synthesized.

mRNA for construction of the cDNA libraries was isolated from human placenta tissue. The cDNA libraries used to isolate the cDNA clones were constructed by standard methods using commercially available reagents such as those from Invitrogen, San Diego, Calif. (Fast Track 2). The cDNA was primed with oligo dT containing a NotI site, linked with blunt to SalI hemikinased adaptors, cleaved with NotI, sized appropriately by gel electrophoresis, and cloned in a defined orientation into the cloning vector pCR2.1 (Invitrogen, Inc.) using reagents and protocols from Life Technologies, Gaithersburg, Md. (Super Script Plasmid System). The double stranded cDNA was sized to greater than 1000 bp and the cDNA was cloned into BamHI/NotI cleaved vector. pCR2.1 is a commercially available plasmid, designed for easy cloning of PCR fragments, that carries AmpR and KanR genes for selection, and LacZ gene for blue-white selection.

In order to screen several libraries for a source of a full-length clone, DNA from the libraries was screened by PCR amplification with the PCR primer pair identified above. A positive library was then used to isolate clones encoding the PRO285 gene using the probe oligonucleotide and one of the PCR primers.

A cDNA clone was sequenced in entirety. The entire nucleotide sequence of DNA40021 (encoding PRO285) is shown in FIG. 2 (SEQ ID NO:2). Clone DNA40021 contains a single open reading frame with an apparent translational initiation site at nucleotide positions 61-63 (FIG. 2). The predicted polypeptide precursor is 1049 amino acids long, including a putative signal peptide at amino acid positions 1-29, a putative transmembrane domain between amino acid positions 837-860, and a leucine zipper pattern at amino acid positions 132-153 and 704-725, respectively. It is noted that the indicated boundaries are approximate, and the actual limits of the indicated regions might differ by a few amino acids. Clone DNA40021 has been deposited with ATCC (designation: DNA40021-1154) and is assigned ATCC deposit no. 209389.

Based on a BLAST and FastA sequence alignment analysis (using the ALIGN computer program) of the full-length sequence is a human analogue of the *Drosophila* Toll protein, and is homologous to the following human Toll proteins: Toll1 (DNAX# HSU88540-1, which is identical with the random sequenced full-length cDNA #HUMRSC786-1); Toll2 (DNAX# HSU88878-1); Toll3 (DNAX# HSU88879-1); and Toll4 (DNAX# HSU88880-1).

Example 2

Isolation of cDNA Clones Encoding Human PRO286

A proprietary expressed sequence tag (EST) DNA database (LIFESEQ™, Incyte Pharmaceuticals, Palo Alto, Calif.) was searched and an EST (#694401) was identified which showed homology to the *Drosophila* Toll protein.

Based on the EST, a pair of PCR primers (forward and reverse):

```
GCCGAGACAAAAACGTTCTCC       (SEQ ID NO: 8)

CATCCATGTTCTCATCCATTAGCC,   (SEQ ID NO: 9)
```
and
a probe:

```
                                              (SEQ ID NO: 10)
TCGACAACCTCATGCAGAGCATCAACCAAAGCAAGAAAACAGTATT
```
were synthesized.

mRNA for construction of the cDNA libraries was isolated from human placenta tissue. This RNA was used to generate an oligo dT primed cDNA library in the vector pRK5D using reagents and protocols from Life Technologies, Gaithersburg, Md. (Super Script Plasmid System). pRK5D is a cloning vector that has an sp6 transcription initiation site followed by an SfiI restriction enzyme site preceding the XhoI/NotI cDNA cloning sites. The cDNA was primed with oligo dT containing a NotI site, linked with blunt to SalI hemikinased adaptors, cleaved with NotI, sized to greater than 1000 by appropriately by gel electrophoresis, and cloned in a defined orientation into XhoI/NotI-cleaved pRK5D.

In order to screen several libraries for a source of a full-length clone, DNA from the libraries was screened by PCR amplification with the PCR primer pair identified above. A positive library was then used to isolate clones encoding the PRO286 gene using the probe oligonucleotide identified above and one of the PCR primers.

A cDNA clone was sequenced in entirety. The entire nucleotide sequence of DNA42663 (encoding PRO286) is shown in FIG. 4 (SEQ ID NO:4). Clone DNA42663 contains a single open reading frame with an apparent translational initiation site at nucleotide positions 57-59 (FIG. 4). The predicted polypeptide precursor is 1041 amino acids long, including a putative signal peptide at amino acid positions 1-26, a potential transmembrane domain at amino acid positions 826-848, and leucine zipper patterns at amino acids 130-151, 206-227, 662-684, 669-690 and 693-614, respectively. It is noted that the indicated boundaries are approximate, and the actual limits of the indicated regions might differ by a few amino acids.

Clone DNA42663 has been deposited with ATCC (designation: DNA42663-1154) and is assigned ATCC deposit no. 209386.

Based on a BLAST and FastA sequence alignment analysis (using the ALIGN computer program) of the full-length sequence of PRO286, it is a human analogue of the *Drosophila* Toll protein, and is homologous to the following human Toll proteins: Toll1 (DNAX# HSU88540-1, which is identical with the random sequenced full-length cDNA #HUMRSC786-1); Toll2 (DNAX# HSU88878-1); Toll3 (DNAX# HSU88879-1); and Toll4 (DNAX# HSU88880-1).

Example 3

Isolation of cDNA Clones Encoding Human PRO358

The extracellular domain (ECD) sequences (including the secretion signal sequence, if any) from known members of the human Toll receptor family were used to search EST databases. The EST databases included public EST databases (e.g., GenBank) and a proprietary EST database (LIFESEQ™, Incyte Pharmaceuticals, Palo Alto, Calif.). The search was performed using the computer program BLAST or BLAST2 [Altschul et al., *Methods in Enzymology*, 266: 460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

An EST was identified in the Incyte database (INC3115949).

Based on the EST sequence, oligonucleotides were synthesized to identify by PCR a cDNA library that contained the sequence of interest and for use as probes to isolate a clone of the full-length coding sequence for PRO358.

A pair of PCR primers (forward and reverse) were synthesized:

```
TCCCACCAGGTATCATAAACTGAA         (SEQ ID NO: 15)

TTATAGACAATCTGTTCTCATCAGAGA      (SEQ ID NO: 16)
```

A probe was also synthesized:

```
                                       (SEQ ID NO: 17)
AAAAAGCATACTTGGAATGGCCCAAGGATAGGTGTAAATG
```

In order to screen several libraries for a source of a full-length clone, DNA from the libraries was screened by PCR amplification with the PCR primer pair identified above. A positive library was then used to isolate clones encoding the PRO358 gene using the probe oligonucleotide and one of the PCR primers.

RNA for construction of the cDNA libraries was isolated from human bone marrow (LIB256). The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO358 (FIGS. 13A and 13B, SEQ ID NO:14) and the derived protein sequence for PRO358 (FIGS. 12A-12C, SEQ ID NO:13).

The entire nucleotide sequence of the clone identified (DNA47361) is shown in FIG. 13A-B (SEQ ID NO:14). Clone DNA47361 contains a single open reading frame with an apparent translational initiation site (ATG start signal) at nucleotide positions underlined in FIGS. 13A and 13B. The predicted polypeptide precursor is 811 amino acids long, including a putative signal sequence (amino acids 1 to 19), an extracellular domain (amino acids 20 to 575, including leucine rich repeats in the region from position 55 to position 575), a putative transmembrane domain (amino acids 576 to 595). Clone DNA47361 (designated DNA47361-1249) has been deposited with ATCC and is assigned ATCC deposit, no. 209431.

Based on a BLAST and FastA sequence alignment analysis (using the ALIGN computer program) of the full-length sequence of PRO286, it is a human analogue of the *Drosophila* Toll protein, and is homologous to the following human Toll proteins: Toll1. (DNAX# HSU88540-1, which is identical with the random sequenced full-length cDNA #HUMRSC786-1); Toll2 (DNAX# HSU88878-1); Toll3 (DNAX# HSU88879-1); and Toll4 (DNAX# HSU88880-1).

Example 4

Use of PRO285, PRO286 and PRO358 DNA as a Hybridization Probe

The following method describes use of a nucleotide sequence encoding PRO285, PRO286 or PRO358 as a hybridization probe. In the following description, these proteins are collectively referred to as "Toll homologues."

DNA comprising the coding sequence of a Toll homologue is employed as a probe to screen for homologous DNAs (such as those encoding naturally-occurring variants of these particular Toll proteins in human tissue cDNA libraries or human tissue genomic libraries.

Hybridization and washing of filters containing either library DNAs is performed under the following high stringency conditions. Hybridization of radiolabeled Toll homologue-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence Toll homologue can then be identified using standard techniques known in the art.

Example 5

Expression of PRO285, PRO286, and PRO358 in *E. coli*

This example illustrates preparation of an unglycosylated form of PRO285, PRO285 or PRO358 ("Toll homologues") by recombinant expression in *E. coli*.

The DNA sequence encoding a Toll homologue is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO285 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized Toll homologue can then be purified using a metal chelating column under conditions that allow tight binding of the protein.

Example 6

Expression of PRO285, PRO286 and PRO358 in Mammalian Cells

This example illustrates preparation of a glycosylated form of PRO285, PRO286 and PRO358 ("Toll homologues") by recombinant expression in mammalian cells.

The vector, pRK5 (see EP 307,247, published Mar. 15, 1989), is employed as the expression vector. Optionally, the Toll homologue-encoding DNA is ligated into pRK5 with selected restriction enzymes to allow insertion of the Toll homologue-encoding DNA using ligation methods such as described in Sambrook et al., supra. The resulting vector is called pRK5-PRO285, -PRO286 or -PRO358, as the case may be.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO285, -PRO286, or -PRO358 DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO285 polypeptide. The cultures containing transfected cells may undergo further incubation (in serum free medium) and the medium is tested in selected bioassays.

In an alternative technique, Toll homologue DNA may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO(285)/(286)/(358) DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing the corresponding expressed Toll homologue can then be concentrated and purified by any selected method, such as dialysis and/or column chromatography.

In another embodiment, the Toll homologues can be expressed in CHO cells. The pRK5-vectors can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO285, PRO286 or PRO358 polypeptide, the culture medium may be replaced with serum free medium. Preferably, the cultures are incubated for about 6 days, and then the conditioned medium is harvested. The medium containing the expressed Toll homologue can then be concentrated and purified by any selected method.

Epitope-tagged Toll homologues may also be expressed in host CHO cells. The Toll homologue DNA may be subcloned out of the pRK5 vector. The subclone insert can undergo PCR to fuse in frame with a selected epitope tag such as a poly-his tag into a Baculovirus expression vector. The poly-his tagged insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged Toll homologue can then be concentrated and purified by any selected method, such as by $Ni^{2+}$-chelate affinity chromatography.

Example 7

Expression of PRO285. PRO286, and PRO358 in Yeast

The following method describes recombinant expression of PRO285, PRO286 or PRO358 ("Toll homologues") in yeast.

First, yeast expression vectors are constructed for intracellular production or secretion of a Toll homologue from the ADH2/GAPDH promoter. DNA encoding the desired Toll homologue, a selected signal peptide and the promoter is inserted into suitable restriction enzyme sites in the selected plasmid to direct intracellular expression. For secretion, DNA encoding the selected Toll homologue can be cloned into the selected plasmid, together with DNA encoding the ADH2/

GAPDH promoter, the yeast alpha-factor secretory signal/leader sequence, and linker sequences (if needed) for expression.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant Toll homologues can subsequently be isolated and purified by removing the yeast cells from the fermentation medium by centrifugation and then concentrating the medium using selected cartridge filters. The concentrate containing the Toll homologue may further be purified using selected column chromatography resins.

Example 8

Expression of PRO285, PRO286 and PRO358 in Baculovirus Infected Insects Cells

The following method describes recombinant expression of PRO285, PRO286 and PRO358 ("Toll homologues") in Baculovirus infected insect cells.

The Toll homologue coding sequence is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the Toll homologue coding sequence or the desired portion of the coding sequence (such as the sequence encoding the extracellular domain) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged Toll homologue can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO285 are pooled and dialyzed against loading buffer.

Alternatively, purification of the IgG tagged (or Fc tagged) Toll homologues can be performed using known chromatography techniques, including for instance, Protein A or protein G column chromatography.

Example 9

NF-κB Assay

As the Toll proteins signal through the NF-κB pathway, their biological activity can be tested in an NF-κB assay. In this assay Jurkat cells are transiently transfected using Lipofectamine reagent (Gibco BRL) according to the manufacturer's instructions. 1 μg pB2XLuc plasmid, containing NF-κB-driven luciferase gene, is contransfected with 1 μg pSRαN expression vector with or without the insert encoding PRO285 or PRO286. For a positive control, cells are treated with PMA (phorbol myristyl acetate; 20 ng/ml) and PHA (phytohaemaglutinin, 2 μg/ml) for three to four hours. Cells are lysed 2 or 3 days later for measurement of luciferase activity using reagents from Promega.

Example 10

Preparation of Antibodies that Bind PRO285. PRO286, or PRO358

This example illustrates preparation of monoclonal antibodies which can specifically bind PRO285, PRO286 or PRO358 ("Toll homologues").

Techniques for producing the monoclonal antibodies are known in the art and are described, for instance, in Goding, supra. Immunogens that may be employed include purified Toll homologues, fusion proteins containing the desired Toll homologue, and cells expressing recombinant Toll homologues on the cell surface. Selection of the immunogen can be made by the skilled artisan without undue experimentation.

Mice, such as Balb/c, are immunized with the Toll homologue immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect PRO285 antibodies.

After a suitable antibody titer has been detected, the animals "positive" for antibodies can be injected with a final intravenous injection of a Toll homologue. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the corresponding Toll homologue. Determination of "positive" hybridoma cells secreting the desired monoclonal antibodies against a Toll homologue is within the skill in the art.

The positive hybridoma cells can be injected intraperitoneally into syngeneic Balb/c mice to produce ascites containing the anti-Toll homologue monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

HuTLR2 Mediates Linopolysaccharide (LPS) Induced Cellular Signaling

Methods

Reagents [$^3$H]-labeled, unlabeled, LCD25 and *S. minnesota* R595LPS were from List Biochemicals (Campbell, Calif.) and all other LPS were from Sigma Chemical Co. (St. Louis, Mo.). LP was supplied as conditioned media from 293 cells transfected with a human LBP expression vector. The TLR2-Fc fusion protein was produced by baculovirus system, and purified as described. Mark et al., *J. Biol. Chem.* 269, 10720-10728 (1994).

Construction of Expression Plasmids A cDNA encoding human TLR2 was cloned from human fetal lung library. The predicted amino acid sequence matched that of the previously published sequence (Rock et al., supra), with the exception of a glu to asp substitution at amino acid 726. The amino acid terminal epitope tag version of TLR2 (dG.TLR2) was constructed by adding an XhoI restriction site immediately upstream of leucine at position 17 (the first amino acid of the predicted mature form of TLR2) and linking this to amino acids 1-53 of herpes simplex virus type I glycoprotein D as described. Mark et al., supra. PCR products were sequenced and subcloned into a mammalian expression vector that contains the puromycin resistance gene. C-terminal truncation variants of gD.TLR2 were constructed by digestion of the cDNA at either a BlpI (variant Δ1) or NsiI (variant Δ2) site present in the coding sequence of the intracellular domain and at a NotI site present in the 3' polylinker of the expression vector followed by ligation of oligonucleotide linkers.

```
Δ1:   5'-TCA GCG GTA AGC-3'       (SEQ ID NO: 18)
and
      5'-GGC CGC TTA CCG C-3'     (SEQ ID NO: 19)

Δ2:   5'-TAA GCT TAA CG-3'        (SEQ ID NO: 20)
and
      5'-GGC CGC TTA AGC TTA TGC  (SEQ ID NO: 21)
      A-3'.
```

The CD4/TLR2 chimera was constructed by PCR and contained amino acids 1-205 (the signal peptide and two immunoglobulin-like domains) of human CD4 fused to amino acids 588-784 (the transmembrane and intracellular domain) of human TLR2 with a linker-encoded valine at the junction of the CD4 and TLR2 sequences. The pGL3.ELAM.tk reporter plasmid contained the sequence

```
                                        (SEQ ID NO: 22)
5'-GGT ACC TTC TGA CAT CAT TGT AAT TTT AAG CAT CGT

GGA TAT TCC CGG GAA AGT TTT TGG ATG CCA TTG GGG

ATT TCC TCT TTA GAT CTG GCG CGG TCC CAG GTC CAC

TTC GCA TAT TAA GGT GAC GCG TGT GGC CTC GAA CAC

CGA GCG ACC CTG CAG CGA CCC GCA AGC TT-3',
``` inserted between the SacI and HindIII sites of the luciferase reported plasmid pGL3 (Promega). The C-terminal epitope tag version of LBP (LBP-FLAG) was constructed by PCR through the addition of an AscI site in place of the native stop codon and the subcloning of this fragment into pRK5-FLAG resulting in the C-terminal addition of amino acids GRA DYK DDD DK (SEQ ID NO: 23).

Stable cell lines/pools 293 human embryonic kidney cells were grown in LGDMEM/HAM's F12 (50:50) media supplemented with 10% FBS, 2 mM glutamine, and penicillin/streptomycin. For stable expression of gD.TLR2, cells were transfected with the gD.TLR2 expression vector and selected for puromycin resistance at a final concentration of 1 µg/ml. A stable pool of cells (293-TLR2 pop1) was isolated by FACS using an antibody to the gD tag. Both the pool and the single cell clone (293-TLR2 clone 1) were characterized by FACS and western blot analyses as described in Mark et al., supra.

Luciferase reporter assay and electrophoretic mobility shift assay (EMSA) 29332 parental or stable cells (2×105 cells per well) were seeded into six-well plates, and transfected on the following day with the expression plasmids together with 0.5 µg of the luciferase reporter plasmid pGL3-ELAM.tk and 0.05 µg of the *Renilla* luciferase reported vector as an internal control. After 24 hours, cells were treated with either LPS, LBP or both LPS and LBP and reporter gene activity was measured. Data are expressed as relative luciferase activity by dividing firefly luciferase activity with that of *Renilla* luciferase. For EMSA, nuclear extracts were prepared and used in a DNA-binding reaction with a 5'-[$^{32}$P]-radiolabelled oligonucleotides containing a consensus NF-κB binding site (Santa Cruz Biotechnology, sc-2511). The identity of NF-κB in the complex was confirmed by supershift with antibodies to NF-κB (data not shown).

RNA expression The tissue northern blot was purchased from Clontech and hybridized with a probe encompassing the extracellular domain of TLR2. Polyadenylated mRNA was isolated from 293 cells or 293-TLR2 cells and Norther blots were probed with human IL-8 cDNA fragment. TLR2 expression was determined using quantitative PCR using real time "Taqman™" technology and analyzed on a Model 770 Sequence Detector (Applied Biosystems, Foster City, Calif., USA) essentially as described (Luoh et al., *J. Mol. Endocrinol.* 18, 77-85 [1997]). Forward and reverse primers,

```
                                        SEQ ID NO: 24
    5'-GCG GGA AGG ATT TTG GGT AA-3',
    and
```

-continued

SEQ ID NO: 25
5'-GAT CCC AAC TAG ACA AAG ACT GGT C-3' were used with a hybridization probe,

SEQ ID NO: 25
5'-TGA GAG CTG CGA TAA AGT CCT AGG TTC CCA TAT-3' labeled on the 5' nucleotide with a reporter dye FAM and the 3' nucleotide with a quenching dye TAMRA. Macrophage/monocytes were treated 16 h with 1 µg/ml of LPS.

Receptor binding assay To determine the direct binding, 20 ng of [$^3$H]-LPS was mixed with 600 ng of TLR2-Fc in 100 µl of binding buffer (150 mM NaCl, 20 mM Hepes, 0.03% BSA) containing 15 µl protein A sepharose. After 3 h-incubation at room temperature, protein A sepharose samples were washed twice with cold PBS/0.1% NP-40 and resuspended in binding buffer including 1% SDS and 25 mM EDTA, and counted.

Results

In *Drosophila*, the Toll receptor is required for embryonic dorso-ventral pattern formation and also participated in an anti-fungal immune response in the adult fly. Belvin and Anderson, *Ann. Rev. Cell. Biol.* 12, 393-416 (1996); Lemaitre et al., *Cell* 86, 973-983 (1996). Toll is a type I transmembrane protein containing an extracellular domain with multiple leucine-rich repeats (LRRs) and a cytoplasmic domain with sequence homology to the interleukin-1 receptor (IL-1R), and several plant disease-resistance proteins. Activation of Toll leads to induction of genes through the activation of the NF-κB pathway. As noted before, there are several human homologues that have been cloned, some of which are disclosed as novel proteins in the present application. These human proteins mirror the topographic structure of their *Drosophila* counterpart. Overexpression of a constitutively active mutant of one human TLR (TLR4) has been shown to lead to the activation of NF-κB and induction of the inflammatory cytokines and constimulatory molecules (Medzhitov et al., and Rock et al., supra.).

Figure 5B:
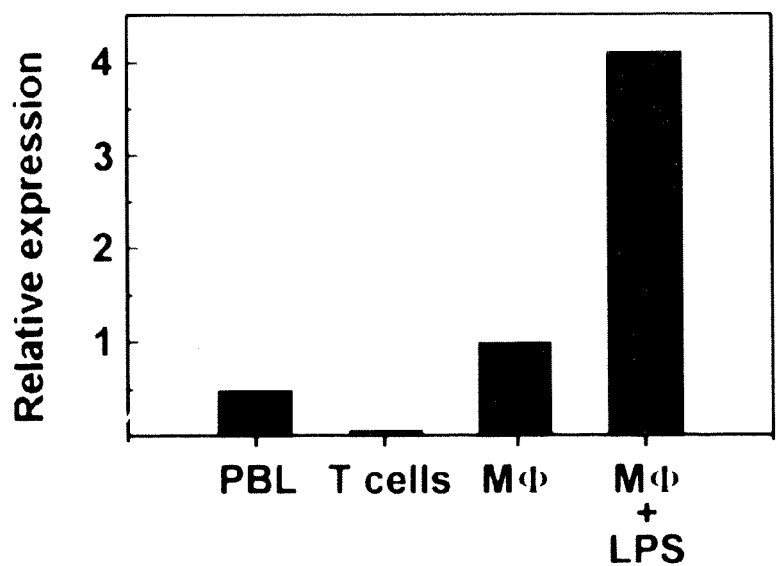

To examine if human TLRs might be involved in LPS-induced cell activation, we first investigated the expression of TLRs in a variety of immune tissues. One of the TLRs, TLR2, was found to be expressed in all lymphoid tissues examined with the highest expression in peripheral blood leukocytes (FIG. 5a). Expression of TLR2 is enriched in monocytes/macrophages, the primary CD14-expressing and LPS-responsive cells. Interestingly, tLR2 is up-regulated upon stimulation of isolated monocytes/macrophages with LPS (FIG. 5b), similar to what has been reported for CD14 (Matsuura et al., *Eur. J. Immunol.* 22, 1663-1665 [1992]; Croston et al., *J. Biol. Chem.* 270, 16514-16517 [1995]).

Figure 6A:
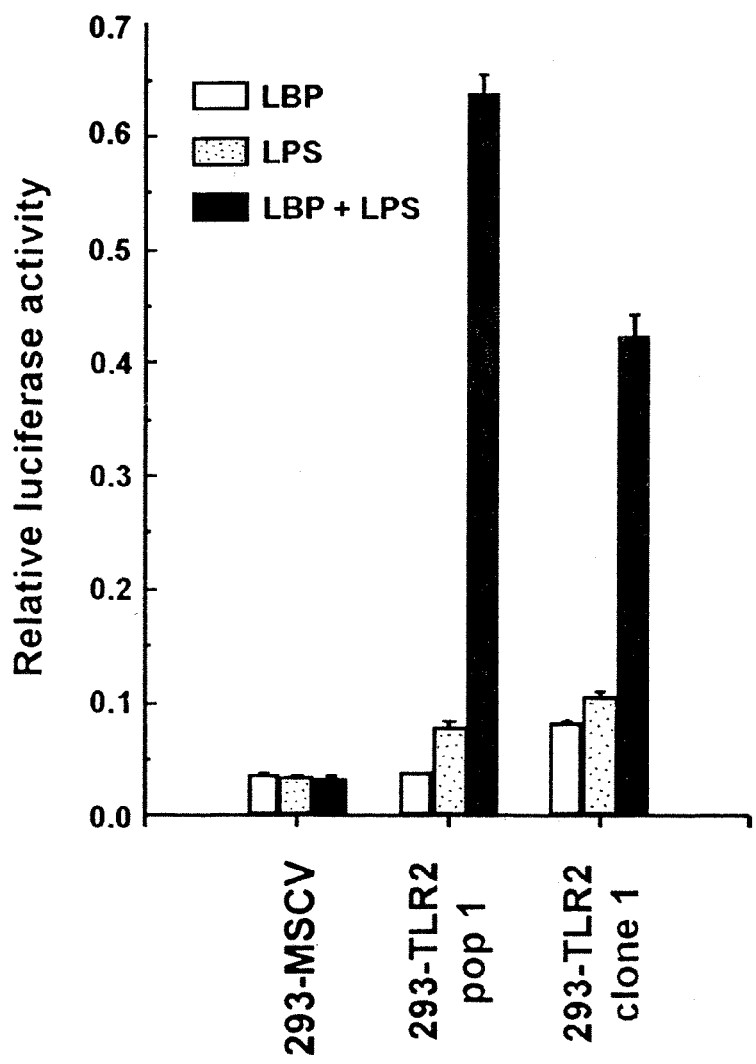
FIG. 6 TLR2 mediates LPS-induced signaling. a. 293 cells stably expressing TLR2 acquire LPS responsiveness. Either a population of stable clones expressing gD.TLR2 (293-TLR2 pop1) or a single clone of cells expressing gD.TLR2 (293-TLR2 clone 1) or control cells (293-MSCV) that were stably transfected with the expression vector alone were transiently transfected with pGL3.ELAM.tk and then stimulated with 1 μg/ml of 055:B5 enhancer for 6 h with or without LBP in serum-free medium. Activation of the ELAM enhancer was measured as described in the Examples. Results were obtained from two independent experiments. No stimulation was observed using the control reporter plasmid that lacked the ELAM enhancer (data not sown). Expression of the reporter plasmid was equivalent in untreated cells or cells treated with LBP alone (data not shown). b. Western blot showing expression of epitope-tagged TLR2 in 293 cells. c. Time course of TLR2-dependent LPS-induced activation and translocation of NF-κB. Nuclear extracts were prepared from cells treated with 055:B5 LPS (10 μg/ml) and LBP for the indicated times (top), or cells pretreated with 1 μM cycloheximide (CHX) for 1 h the stimulated with 1 μg/ml LPS for 1 h in the presence of LBP in serum-free medium (bottom). d. Effect of mCD14 on NF-κB activation by TLR2. Vector control (193-MSCV) or 293-TLR2 pop1 cells were transfected with the reporter plasmid, and a CD14 expression vector (+mCD14) or vector control (−mCD14), respectively. After 24 h, transfected cells were stimulated with 055:B5 LPS for 6 h in the presence of LBP in serum-free medium. The data presented are representative from three independent experiments.
Figure 6B:
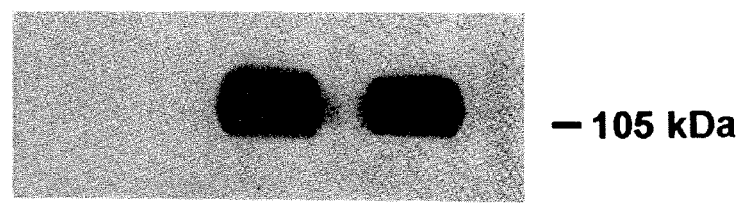
Figure 6C:
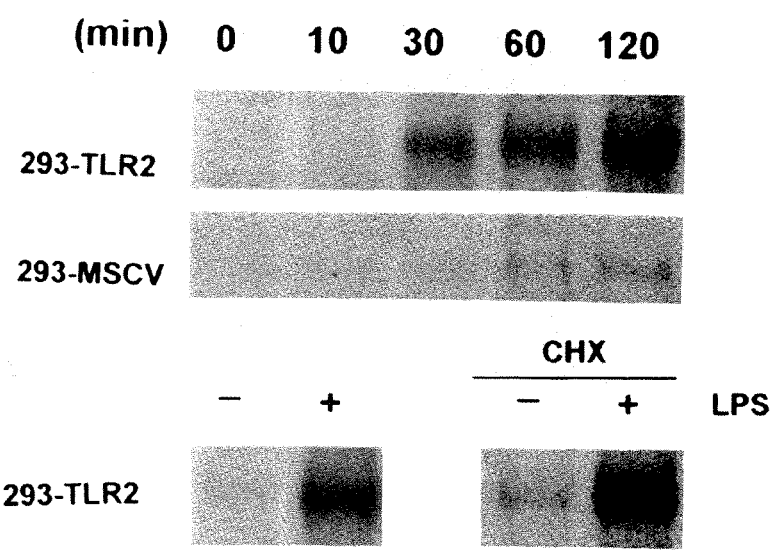

This result prompted us to determine, if TLR2 is involved in LPS-mediated cellular signaling. We engineered human embryonic kidney 293 cells to express a version of TLR2 (gD-TLR2) containing an amino-terminal epitope-tag. A stable pool of clones as well as an individual clone was isolated and shown to express a novel protein of about 105 kDa (FIG. 6b), consistent with the predicted size of TLR2 (~89 kDa) and the presence of 4 potential sites for N-linked glycosylation. We examined the response of 293 or 293-TLR2 cells and LBP by measuring the expression of a reported gene driven by the NF-κB responsive enhancer of the E-selectin gene (Croston et al., supra). While neither LPS nor LBP treatment alone resulted in significant gene activation, addition of both LPS and LBP resulted in substantial induction of reporter gene activity in cells expressing TLR2, but not in control 293 cells (FIG. 6a). Furthermore, using an electrophoretic mobility shift assay (EMSA), we found that LPS, in combination with LBP, induced NK-κB activity in TLR2 expressing cells (FIG. 6c). The kinetics of LPS-induced NF-κB activity in 293-TLR2 cells resembled that of myeloid and nonmyeloid cells (Delude et al., *J. Biol. Chem.* 269, 22253-22260 [1994]; Lee et al., *Proc. Natl. Acad. Sci. USA* 900, 9930-9934 [1993]) in that nuclear localization of NF-κB is maximal within 30 minutes following exposure to LPS. Activation of NF-κB by LPS/LBP in 293-TLR2 cells does not require de novo protein synthesis, since pretreatment with cycloheximide (FIG. 6c) or actinomycin D (not shown) does not inhibit NF-κB activation.

Figure 6D:
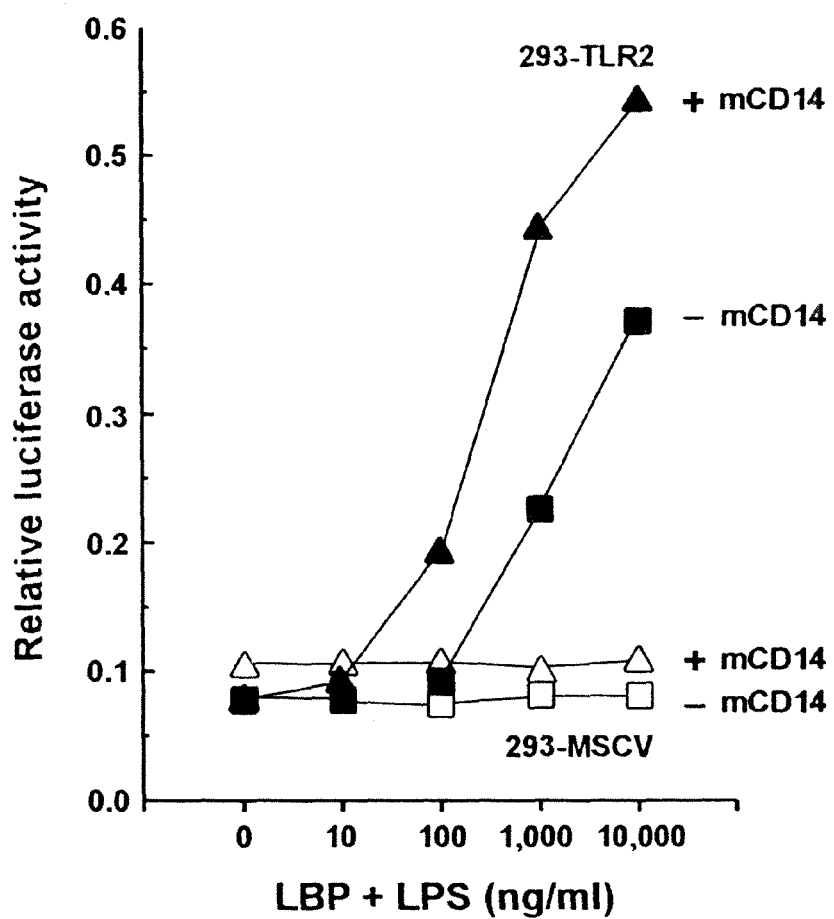

Both the membrane-bound form of CD14 (mCD14), which is present on myeloid cells, and soluble CD14 (sCD14) which is present in plasma (Bazil et al., *Eur. J. Immunol.* 16, 1583-1589 [1986]), have been shown to enhance the responsiveness of cells to LPS. We observed that 293 cells express little or no CD14 on their surface (data not shown). However, transient transfection of 293 cells which mCD14 increased the sensitivity and magnitude of TLR2-mediated LPS responsiveness (FIG. 6d).

Figure 7A:
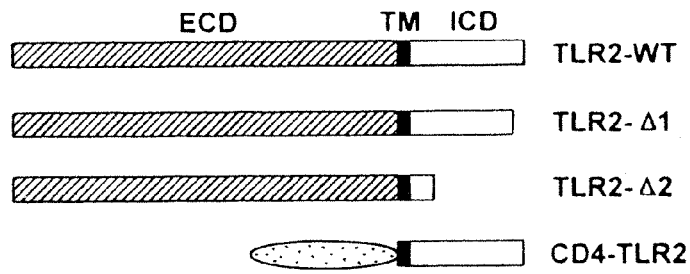
FIG. 7 Domain function of TLR2 in signaling. a. Illustrations of various TLR2 constructs. TLR2-WT, the full-length epitope-tagged form of TLR2, TLR2-Δ1 and -Δ2 represent a truncation of 13 or 141 amino acids at the carboxyl terminus, respectively. CD4-TLR2, a human CD4-TLR2 chimera replacing the extracellular domain of TLR2 with amino acids 1-205 of human CD4. ECD, extracellular domain; TM, transmembrane region; ICD, intracellular domain. b. C-terminal residues critical for IL-1R and TLR2 signal transduction. Residue numbers are shown to the right of each protein. Arrow indicated the position of the TLR2-Δ1 truncation. *, residues essential for IL-1R signaling (Heguy et al., *J. Biol. Chem.* 267, 2605-2609 [1992]; Croston et al., *J. Biol. Chem.* 27o, 16514-16517 [1995])l I, identical amino acid; conservative changes. c. TLR-R2 variants fail to induce NF-κB in response to LPS and LBP. 293 cells were transiently transfected with pGL3.ELAM.tk and expression vectors encoding full-length TLR2 or TLR2 variants as indicated. The cells were also transfected with a CD14 expression plasmid (+mCD14) or with a control plasmid (−mCD14). Equal expression of each protein is confirmed by Western blot using either anti-gD or CD4 antibody (FIG. 7D). The luciferase assay was performed as described in the Examples. Data were obtained from duplicate experiments.
Figure 7B:
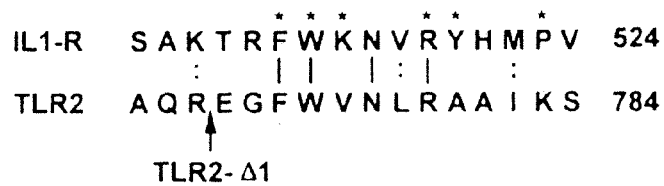
Figure 7C:
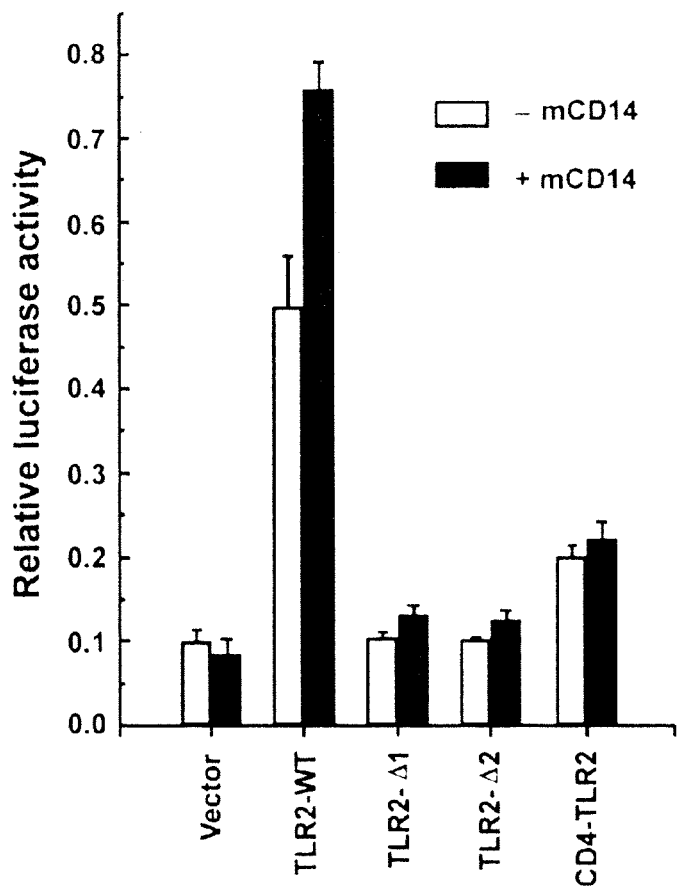
Figure 7D:
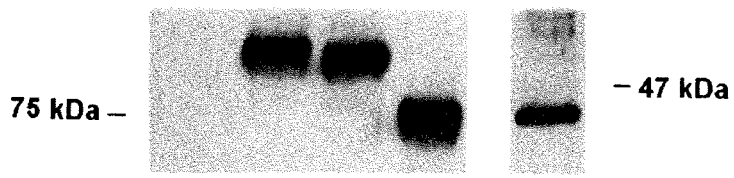

The data presented above suggested that TLR2 might function as a signaling transducer for LPS. To examine the role of the intracellular domain of TLR2 in mediating the LPS response, we determined if TLR2 variants with C-terminal truncations of either 13 (TLR-M) or 141 amino acids (TLR2-Δ2) could regulate the ELAM reporter in transiently transfected 293 cells. We observed that both C-terminal truncation variants were defective for activation of the reporter gene although we could detect expression of these receptors at the cells surface by FACS analysis (not shown) and by Western blot (FIGS. 7c-7d). The region of the intracellular domain deleted in TLR2-Δ1 bears striking similarity to a region of the IL-1R intracellular domain that is required fro association with the IL-1R-associated kinase IRAK (Croston et al., supra) (FIG. 7b). We also demonstrated that the extracellular domain (ECD) of TLR2 is required for LPS-responsiveness in that a TLR2 variant in which the ECD of TLR2 was replaced with a portion of the ECD of CD4 also failed to respond to LPS (FIGS. 7a and 7b).

Figure 8A:
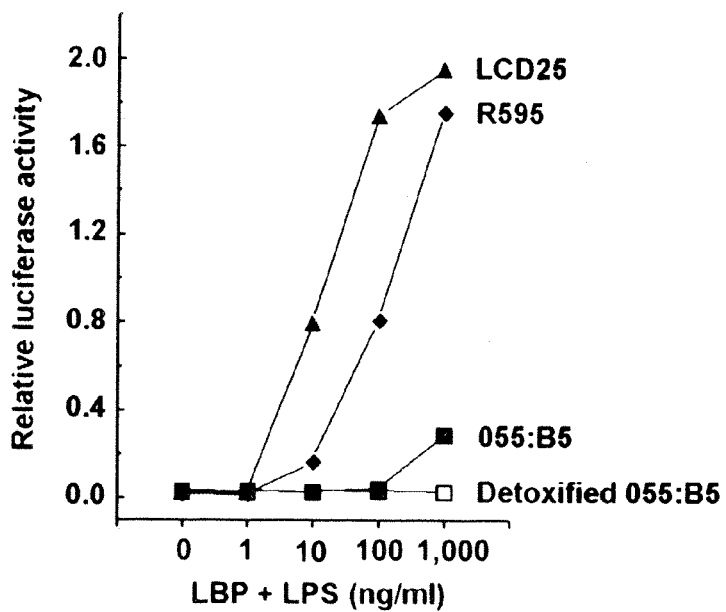
FIG. 8 High potency of *E. coli* K12 LPS (LCD25) and its binding to TLR2. a. Dose-response curve of various LPS preparations. b. Specific interaction of [³H]-LPS (LCD25) with the extracellular domain of TLR2. Specific binding was observed to TLR2-Fc, but not to either Fc alone, or fusion proteins containing the extracellular domains of Rse, Axl, Her2, or Her4. Binding to TLR2-Fc was specifically competed with LCD25 LPS, but not with detoxified LPS.

LPS is a complex glycolipid consisting of the proximal hydrophobic lipid A moiety, the distal hydrophilic O-antigen polysaccharide region and the core oligosaccharide that joins lipid A and O-antigen structures. In contrast to the lipid A portion, there is a considerable diversity in the O-antigen structures from different Gram-negative bacteria. Lipid A is required for LPS responses, and treatments that remove the fatty acid side chains of lipid A inactivate LPS. We compared the potency of LPS prepared from various Gram-negative bacteria, as well as LPS which had been "detoxified" by alkaline hydrolysis. We observed that LPS isolated from *Escherichia coli* serotype LCD25 was nearly two orders of magnitude more potent that the serologically distinct *Escherichia coli* 055:B5 LPS for activating TLR2 (FIG. 8a). LPS prepared from *S. minnesota* R595 LPS is also a potent inducer of TLR2 activity, while TLR2 failed to respond to "detoxified LPS".

Figure 8B:
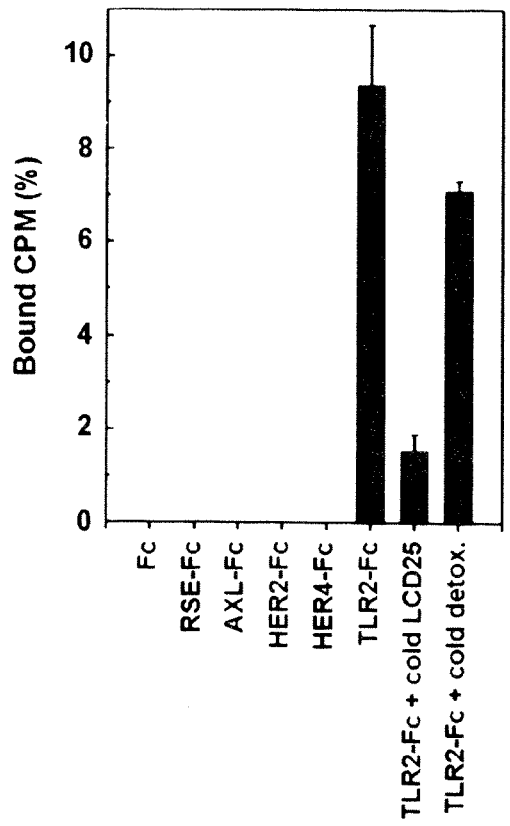

We examined if TLR2 binds LPS by determining if a soluble form of the TLR2 extracellular domain (TLR2-Fc) bound $^3$H-labeled LPS in an in vitro assay. We observed that $^3$H-LCD25 LPS bound the TLR2-Fc fusion protein, but did not bind either Fc alone, or fusion proteins containing the ECD of several other receptors (FIG. 8b). This binding was specifically competed with cold LCD25 LPS but not with detoxified LPS. Preliminary analysis of the binding of LPS to TLR2-Fc suggests that the Kd is relatively low (500-700 nM)

and that the kinetics of binding are very slow (data not shown). We speculate that other proteins, such as LBP, might act to enhance the binding of LPS to TLR2 in vivo, much like LBP acts to transfer LPS from its free, aggregated (micellar form) to CD14. This is consistent with our in vivo results showing that LBP is required to obtain a sensitive response of TLR2 to LPS (FIG. 6a).

Figure 9:
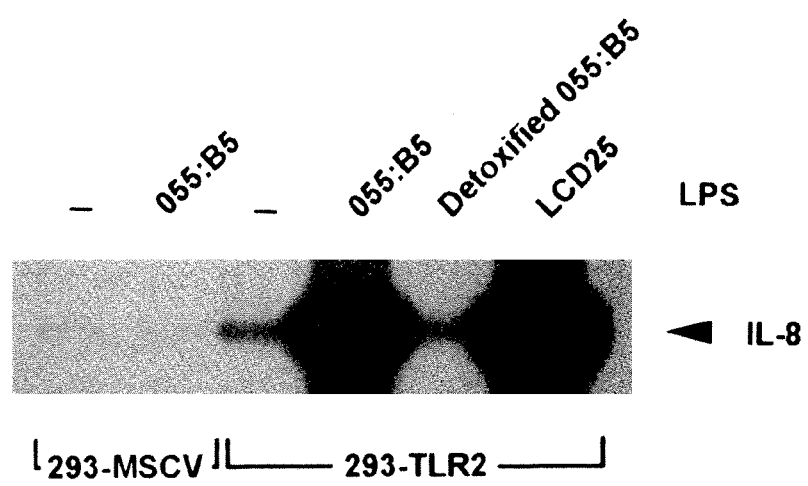
FIG. 9 TLR2 is required for the LPS-induced IL-8 expression. 293-MSCV vector control and 293-TLR2 cells transiently expressing mCD14 were stimulated with LBP alone or together with the indicated type of LPS at concentrations of 1 μg/ml in serum-free medium for 6 h. Equal amounts of poly-(A) RNAs were used for Northern analysis.

ILS treatment of macrophages leads to expression of a number of inflammatory cytokines. Similarly expression of TLR2 in 293 cells resulted in a >100 fold-induction of IL-8 mRNA in response to LPS/LBP, while detoxified LPS is inactive in this assay (FIG. 9).

These data suggest that TLR2 plays a sentinel role in the innate immune response, the first line of defense against microbial pathogens. TLR2 and CD14 are both expressed on myeloid cells, and their induction is coordinately induced upon LPS treatment. Expression of TLR2 in non-myeloid cells confers LPS responsiveness to normally non-responsive cells by a mechanism that is dependent on LBP and is enhanced by the expression of mCD14. LPS treatment of TLR2 expressing cells results in activation of NF-κB and subsequent induction of genes that initiate the adaptive response such as IL-8 (FIG. 9). Our data suggest that TLR2 participates in both sensing the presence of LPS and transmitting this information across the plasma membrane because intact extracellular and intracellular domains are required for LPS responses. Moreover, a region in the C-terminal tail of TLR2 that has homology to a portion of the IL-1R that is required for association with IRAK, is necessary for NF-κB activation.

*Drosophila* Toll and the Toll related-receptor 18 Wheeler play and important role in the induction of antimicrobial peptides in response to bacteria and fungi, respectively. Medzhitov et al., supra. Genetic data has implicated Spätzle as a ligand for Toll in dorsoventral patterning and has led to speculation that a homologue of Spätzle might be important for regulation of human TLRs in the immune response. Our observations that activation of TLR2 by LPS is not blocked by cycloheximide and that the extracellular domain of TLR2 is a low affinity receptor for LPS in vitro is consistent with a model in which TLR2 participated in LPS recognition. Our data does not exclude the possibility that other proteins (such as a Spätzle homologue) may modify the response of TLR2 to LPS. We note that while extracellular domains of TLR2 and *Drosophila* Toll both contain LRRs, they share less than 20% amino acid identity. Secondly, LRR proteins are Pattern Recognition Receptors (PRRs) for a variety of types of molecules, such as proteins, peptides, and carbohydrates. Dangl et al., *Cell* 91, 17-24 (1997). Thirdly, the requirement for Spätzle in the *Drosophila* immune response is less clear than that of Toll. Unlike defects in Toll, Spätzle mutants induce normal levels of the antimicrobial peptides Defensin and Attacin and are only partially defective in Cecropin A expression following fungal challenge, and are not defective in activation of Dorsal in response to injury. Lemaitre et al., *Cell* 86, 973-983 (1996); Lemaitre et al., *EMBO J.* 14, 536-545 (1995).

As noted before, TLR2 is a member of a large family of human Toll-related receptors, including the three novel receptors (encoded by DNA40021, DNA42663, and DNA47361, respectively) specifically disclosed in the present application. The data presented in this example as well as evidence for the involvement of TLR4 in activation of NF-κB responsive genes, suggest that a primary function of this family of receptors is to act as pathogen pattern recognition receptors sensing the presence of conserved molecular structures present on microbes, originally suggested by Janeway and colleagues (Medzhitov et al., supra). The human TLR family may be targets for therapeutic strategies for the treatment of septic shock.

Example 12

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1: 169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
1.0 µl DTT (100 mM)
2.0 µl NTP mix (2.5 mM: 10µ; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the gel was immediately placed on ice. The wells of gel were flushed, the sample loaded, and run at 180-250 volts for 45 minutes. The gel was wrapped in saran wrap and exposed to XAR, film with an intensifying screen in −70° C. freezer one hour to overnight.

$^{33}$P-Hybridization

Pretreatment of frozen sections The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 µg/ml proteinase K for 10 minutes at 37°

C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

Pretreatment of paraffin-embedded sections The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration were performed as described above.

Prehybridization The slides were laid out in plastic box lined with Box buffer (4×SSC, 50% formamide)—saturated filter paper. The tissue was covered with 50 µl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1-4 hours.

Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

Washes Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

Results
PRO285 (DNA40021)

The expression pattern of PRO285 (DNA40021) in human adult and fetal tissues was examined. The following probes were used, synthesized based upon the full-length DNA40021 sequence:

```
Oligo 1:
                                         (SEQ ID NO: 27)
GGA TTC TAA TAC GAC TCA CTA TAG GGC AAA CTC TGC

CCT GTG ATG TCA

Oligo 2:
                                         (SEQ ID NO: 28)
CTA TGA AAT TAA CCC TCA CTA AAG GGA ACG AGG GCA

ATT TCC ACT TAG
```

In this experiment, low levels of expression were observed in the placenta and over hematopoietic cells in the mouse fetal liver. No expression was detected in either human fetal, adult or chimp lymph node and no expression was detected in human fetal or human adult spleen. These data are no fully consistent with Northern blot or PCR data, probably due to the lack of sensitivity in the in situ hybridization assay. It is possible that further tissues would show some expression under more sensitive conditions.

PRO358 (DNA47361)

The expression pattern of PRO358 (DNA47361) in human adult and fetal tissues was examined. The following probes were used, synthesized based upon the full-length DNA47361 sequence:

```
Oligo 1:
                                         (SEQ ID NO: 29)
GGA TTC TAA TAC GAC TCA CTA TAG GGC TGG CAA TAA

ACT GGA GAC ACT

Oligo 2:
                                         (SEQ ID NO: 30)
CTA TGA AAT TAA CCC TCA CTA AAG GGA TTG AGT TGT

TCT TGG GTT GTT
```

In this experiment, expression was found in gut-associated lymphoid tissue and developing splenic white pulp in the fetus. Low level expression was seen in the pALS region of normal adult spleen. Although all other tissues were negative, it is possible that low levels of expression could be observed in other tissue types under more sensitive conditions.

Deposit of Material

The following materials have been deposited with the American Type Culture Collection, 12301 Parklawn Drive, Rockville, Md., USA (ATCC):

| Material | ATCC Dep. No. | Deposit Date |
| --- | --- | --- |
| DNA40021-1154 (encoding PRO285) | 209389 | Oct. 17, 1997 |
| DNA42663-1154 (encoding PR0286) | 209386 | Oct. 17, 1997 |
| DNA47361-1249 | 209431 | Nov. 7, 1997 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody which binds to a PRO286 polypeptide consisting essentially of amino acids 1 to 1041 encoded by SEQ ID NO:4.

2. The antibody of claim 1 wherein said antibody is a monoclonal antibody.

3. The antibody of claim 2 wherein said antibody is one of a chimeric, humanized, and human antibody.

4. The antibody of claim 2 wherein said antibody blocks binding of said polypeptide to one of a Gram-negative and Gram-positive organism.

5. An isolated antibody which specifically binds to a PRO286 polypeptide consisting of amino acid residues 27 to 825 of FIG. 3 (SEQ ID NO:3).

6. The antibody of claim 5 wherein said antibody is a monoclonal antibody.

7. The antibody of claim 6 wherein said antibody is one of a chimeric, humanized, and human antibody.

8. An isolated antibody which binds to a PRO286 polypeptide consisting essentially of:
(a) amino acids 1 to 1041 encoded by SEQ ID NO:4, or
(b) amino acid residues 27 to 825 of SEQ ID NO:3;
wherein said antibody is an agonist or an antagonist of NF-κB activation.

9. The antibody of claim 8, wherein said antibody is an agonist of NF-κB activation.

10. The antibody of claim 8, wherein said antibody is an antagonist of NF-κB activation.

* * * * *

SEQUENCE LISTING

<160> NUMBER OF SEQ ID NOS: 32

<210> SEQ ID NO 1
<211> LENGTH: 1049
<212> TYPE: PRT
<213> ORGANISM: Homo sapiens

<400> SEQUENCE: 1

```
Met Val Phe Pro Met Trp Thr Leu Lys Arg Gln Ile Leu Ile Leu
 1               5                  10                  15

Phe Asn Ile Ile Leu Ile Ser Lys Leu Leu Gly Ala Arg Trp Phe
             20                  25                  30

Pro Lys Thr Leu Pro Cys Asp Val Thr Leu Asp Val Pro Lys Asn
             35                  40                  45

His Val Ile Val Asp Cys Thr Asp Lys His Leu Thr Glu Ile Pro
             50                  55                  60

Gly Gly Ile Pro Thr Asn Thr Thr Asn Leu Thr Leu Thr Ile Asn
             65                  70                  75

His Ile Pro Asp Ile Ser Pro Ala Ser Phe His Arg Leu Asp His
             80                  85                  90

Leu Val Glu Ile Asp Phe Arg Cys Asn Cys Val Pro Ile Pro Leu
             95                 100                 105

Gly Ser Lys Asn Asn Met Cys Ile Lys Arg Leu Gln Ile Lys Pro
            110                 115                 120

Arg Ser Phe Ser Gly Leu Thr Tyr Leu Lys Ser Leu Tyr Leu Asp
            125                 130                 135

Gly Asn Gln Leu Leu Glu Ile Pro Gln Gly Leu Pro Pro Ser Leu
            140                 145                 150

Gln Leu Leu Ser Leu Glu Ala Asn Asn Ile Phe Ser Ile Arg Lys
            155                 160                 165

Glu Asn Leu Thr Glu Leu Ala Asn Ile Glu Ile Leu Tyr Leu Gly
            170                 175                 180

Gln Asn Cys Tyr Tyr Arg Asn Pro Cys Tyr Val Ser Tyr Ser Ile
            185                 190                 195

Glu Lys Asp Ala Phe Leu Asn Leu Thr Lys Leu Lys Val Leu Ser
            200                 205                 210

Leu Lys Asp Asn Asn Val Thr Ala Val Pro Thr Val Leu Pro Ser
            215                 220                 225

Thr Leu Thr Glu Leu Tyr Leu Tyr Asn Asn Met Ile Ala Lys Ile
            230                 235                 240

Gln Glu Asp Asp Phe Asn Asn Leu Asn Gln Leu Gln Ile Leu Asp
            245                 250                 255

Leu Ser Gly Asn Cys Pro Arg Cys Tyr Asn Ala Pro Phe Pro Cys
            260                 265                 270

Ala Pro Cys Lys Asn Asn Ser Pro Leu Gln Ile Pro Val Asn Ala
            275                 280                 285

Phe Asp Ala Leu Thr Glu Leu Lys Val Leu Arg Leu His Ser Asn
            290                 295                 300

Ser Leu Gln His Val Pro Pro Arg Trp Phe Lys Asn Ile Asn Lys
            305                 310                 315

Leu Gln Glu Leu Asp Leu Ser Gln Asn Phe Leu Ala Lys Glu Ile
            320                 325                 330

Gly Asp Ala Lys Phe Leu His Phe Leu Pro Ser Leu Ile Gln Leu
            335                 340                 345
```

-continued

Asp Leu Ser Phe Asn Phe Glu Leu Gln Val Tyr Arg Ala Ser Met
          350                 355                 360

Asn Leu Ser Gln Ala Phe Ser Ser Leu Lys Ser Leu Lys Ile Leu
          365                 370                 375

Arg Ile Arg Gly Tyr Val Phe Lys Glu Leu Lys Ser Phe Asn Leu
          380                 385                 390

Ser Pro Leu His Asn Leu Gln Asn Leu Glu Val Leu Asp Leu Gly
          395                 400                 405

Thr Asn Phe Ile Lys Ile Ala Asn Leu Ser Met Phe Lys Gln Phe
          410                 415                 420

Lys Arg Leu Lys Val Ile Asp Leu Ser Val Asn Lys Ile Ser Pro
          425                 430                 435

Ser Gly Asp Ser Ser Glu Val Gly Phe Cys Ser Asn Ala Arg Thr
          440                 445                 450

Ser Val Glu Ser Tyr Glu Pro Gln Val Leu Glu Gln Leu His Tyr
          455                 460                 465

Phe Arg Tyr Asp Lys Tyr Ala Arg Ser Cys Arg Phe Lys Asn Lys
          470                 475                 480

Glu Ala Ser Phe Met Ser Val Asn Glu Ser Cys Tyr Lys Tyr Gly
          485                 490                 495

Gln Thr Leu Asp Leu Ser Lys Asn Ser Ile Phe Phe Val Lys Ser
          500                 505                 510

Ser Asp Phe Gln His Leu Ser Phe Leu Lys Cys Leu Asn Leu Ser
          515                 520                 525

Gly Asn Leu Ile Ser Gln Thr Leu Asn Gly Ser Glu Phe Gln Pro
          530                 535                 540

Leu Ala Glu Leu Arg Tyr Leu Asp Phe Ser Asn Asn Arg Leu Asp
          545                 550                 555

Leu Leu His Ser Thr Ala Phe Glu Glu Leu His Lys Leu Glu Val
          560                 565                 570

Leu Asp Ile Ser Ser Asn Ser His Tyr Phe Gln Ser Glu Gly Ile
          575                 580                 585

Thr His Met Leu Asn Phe Thr Lys Asn Leu Lys Val Leu Gln Lys
          590                 595                 600

Leu Met Met Asn Asp Asn Asp Ile Ser Ser Ser Thr Ser Arg Thr
          605                 610                 615

Met Glu Ser Glu Ser Leu Arg Thr Leu Glu Phe Arg Gly Asn His
          620                 625                 630

Leu Asp Val Leu Trp Arg Glu Gly Asp Asn Arg Tyr Leu Gln Leu
          635                 640                 645

Phe Lys Asn Leu Leu Lys Leu Glu Glu Leu Asp Ile Ser Lys Asn
          650                 655                 660

Ser Leu Ser Phe Leu Pro Ser Gly Val Phe Asp Gly Met Pro Pro
          665                 670                 675

Asn Leu Lys Asn Leu Ser Leu Ala Lys Asn Gly Leu Lys Ser Phe
          680                 685                 690

Ser Trp Lys Lys Leu Gln Cys Leu Lys Asn Leu Glu Thr Leu Asp
          695                 700                 705

Leu Ser His Asn Gln Leu Thr Thr Val Pro Glu Arg Leu Ser Asn
          710                 715                 720

Cys Ser Arg Ser Leu Lys Asn Leu Ile Leu Lys Asn Asn Gln Ile
          725                 730                 735

Arg Ser Leu Thr Lys Tyr Phe Leu Gln Asp Ala Phe Gln Leu Arg

```
                   740                 745                 750
Tyr Leu Asp Leu Ser Ser Asn Lys Ile Gln Met Ile Gln Lys Thr
               755                 760                 765
Ser Phe Pro Glu Asn Val Leu Asn Asn Leu Lys Met Leu Leu Leu
               770                 775                 780
His His Asn Arg Phe Leu Cys Thr Cys Asp Ala Val Trp Phe Val
               785                 790                 795
Trp Trp Val Asn His Thr Glu Val Thr Ile Pro Tyr Leu Ala Thr
               800                 805                 810
Asp Val Thr Cys Val Gly Pro Gly Ala His Lys Gly Gln Ser Val
               815                 820                 825
Ile Ser Leu Asp Leu Tyr Thr Cys Glu Leu Asp Leu Thr Asn Leu
               830                 835                 840
Ile Leu Phe Ser Leu Ser Ile Ser Val Ser Leu Phe Leu Met Val
               845                 850                 855
Met Met Thr Ala Ser His Leu Tyr Phe Trp Asp Val Trp Tyr Ile
               860                 865                 870
Tyr His Phe Cys Lys Ala Lys Ile Lys Gly Tyr Gln Arg Leu Ile
               875                 880                 885
Ser Pro Asp Cys Cys Tyr Asp Ala Phe Ile Val Tyr Asp Thr Lys
               890                 895                 900
Asp Pro Ala Val Thr Glu Trp Val Leu Ala Glu Leu Val Ala Lys
               905                 910                 915
Leu Glu Asp Pro Arg Glu Lys His Phe Asn Leu Cys Leu Glu Glu
               920                 925                 930
Arg Asp Trp Leu Pro Gly Gln Pro Val Leu Glu Asn Leu Ser Gln
               935                 940                 945
Ser Ile Gln Leu Ser Lys Lys Thr Val Phe Val Met Thr Asp Lys
               950                 955                 960
Tyr Ala Lys Thr Glu Asn Phe Lys Ile Ala Phe Tyr Leu Ser His
               965                 970                 975
Gln Arg Leu Met Asp Glu Lys Val Asp Val Ile Ile Leu Ile Phe
               980                 985                 990
Leu Glu Lys Pro Phe Gln Lys Ser Lys Phe Leu Gln Leu Arg Lys
               995                1000                1005
Arg Leu Cys Gly Ser Ser Val Leu Glu Trp Pro Thr Asn Pro Gln
              1010                1015                1020
Ala His Pro Tyr Phe Trp Gln Cys Leu Lys Asn Ala Leu Ala Thr
              1025                1030                1035
Asp Asn His Val Ala Tyr Ser Gln Val Phe Lys Glu Thr Val
              1040                1045

<210> SEQ ID NO 2
<211> LENGTH: 3283
<212> TYPE: DNA
<213> ORGANISM: Homo sapiens

<400> SEQUENCE: 2
cccatctcaa gctgatcttg gcacctctca tgctctgctc tcttcaacca         50
gacctctaca ttccattttg gaagaagact aaaaatggtg tttccaatgt        100
ggacactgaa gagacaaatt cttatccttt ttaacataat cctaatttcc        150
aaactccttg gggctagatg gtttcctaaa actctgccct gtgatgtcac        200
tctggatgtt ccaagaacc atgtgatcgt ggactgcaca gacaagcatt         250
```

```
tgacagaaat tcctggaggt attcccacga acaccacgaa cctcaccctc      300
accattaacc acataccaga catctcccca gcgtcctttc acagactgga      350
ccatctggta gagatcgatt tcagatgcaa ctgtgtacct attccactgg      400
ggtcaaaaaa caacatgtgc atcaagaggc tgcagattaa acccagaagc      450
tttagtggac tcacttattt aaaatccctt tacctggatg gaaaccagct      500
actagagata ccgcagggcc tcccgcctag cttacagctt ctcagccttg      550
aggccaacaa catctttttcc atcagaaaag agaatctaac agaactggcc      600
aacatagaaa tactctacct gggccaaaac tgttattatc gaaatccttg      650
ttatgtttca tattcaatag agaaagatgc cttcctaaac ttgacaaagt      700
taaaagtgct ctccctgaaa gataacaatg tcacagccgt ccctactgtt      750
ttgccatcta ctttaacaga actatatctc tacaacaaca tgattgcaaa      800
aatccaagaa gatgatttta ataacctcaa ccaattacaa attcttgacc      850
taagtggaaa ttgccctcgt tgttataatg ccccatttcc ttgtgcgccg      900
tgtaaaaata attctcccct acagatccct gtaaatgctt ttgatgcgct      950
gacagaatta aaagttttac gtctacacag taactctctt cagcatgtgc     1000 cccccaagatg gtttaagaac atcaacaaac tccaggaact ggatctgtcc     1050
caaaacttct tggccaaaga aattggggat gctaaatttc tgcatttttct     1100 ccccagcctc atccaattgg atctgtcttt caattttgaa cttcaggtct     1150
atcgtgcatc tatgaatcta tcacaagcat tttcttcact gaaaagcctg     1200
aaaattctgc ggatcagagg atatgtcttt aaagagttga aaagctttaa     1250
cctctcgcca ttacataatc ttcaaaatct tgaagttctt gatcttggca     1300
ctaactttat aaaaattgct aacctcagca tgtttaaaca atttaaaaga     1350
ctgaaagtca tagatctttc agtgaataaa atatcacctt caggagattc     1400
aagtgaagtt ggcttctgct caaatgccag aacttctgta gaaagttatg     1450
aaccccaggt cctggaacaa ttacattatt tcagatatga taagtatgca     1500
aggagttgca gattcaaaaa caaagaggct tctttcatgt ctgttaatga     1550
aagctgctac aagtatgggc agaccttgga tctaagtaaa aatagtatat     1600
tttttgtcaa gtcctctgat tttcagcatc tttctttcct caaatgcctg     1650
aatctgtcag gaaatctcat tagccaaact cttaatggca gtgaattcca     1700
acctttagca gagctgagat atttggactt ctccaacaac cggcttgatt     1750
tactccattc aacagcattt gaagagcttc acaaactgga agttctggat     1800
ataagcagta atagccatta ttttcaatca gaaggaatta ctcatatgct     1850
aaactttacc aagaacctaa aggttctgca gaaactgatg atgaacgaca     1900
atgacatctc ttcctccacc agcaggacca tggagagtga gtctcttaga     1950
actctggaat tcagaggaaa tcacttagat gttttatgga gagaaggtga     2000
taacagatac ttacaattat tcaagaatct gctaaaatta gaggaattag     2050
acatctctaa aaatttccta gtttcttgc ctttctggagt ttttgatggt     2100 atgcctccaa atctaaagaa tctctctttg gccaaaaatg ggctcaaatc     2150
tttcagttgg aagaaactcc agtgtctaaa gaacctggaa actttggacc     2200
tcagccacaa ccaactgacc actgtccctg agagattatc caactgttcc     2250
```

-continued

| | |
|---|---|
| agaagcctca agaatctgat tcttaagaat aatcaaatca ggagtctgac | 2300 |
| gaagtatttt ctacaagatg ccttccagtt gcgatatctg gatctcagct | 2350 |
| caaataaaat ccagatgatc caaaagacca gcttcccaga aaatgtcctc | 2400 |
| aacaatctga agatgttgct tttgcatcat aatcggtttc tgtgcacctg | 2450 |
| tgatgctgtg tggttttgtct ggtgggttaa ccatacggag gtgactattc | 2500 |
| cttacctggc cacagatgtg acttgtgtgg ggccaggagc acacaagggc | 2550 |
| caaagtgtga tctccctgga tctgtacacc tgtgagttag atctgactaa | 2600 |
| cctgattctg ttctcacttt ccatatctgt atctctcttt ctcatggtga | 2650 |
| tgatgacagc aagtcacctc tatttctggg atgtgtggta tatttaccat | 2700 |
| ttctgtaagg ccaagataaa ggggtatcag cgtctaatat caccagactg | 2750 |
| ttgctatgat gctttattg tgtatgacac taaagaccca gctgtgaccg | 2800 |
| agtgggtttt ggctgagctg gtggccaaac tggaagaccc aagagagaaa | 2850 |
| catttaatt tatgtctcga ggaaagggac tggttaccag ggcagccagt | 2900 |
| tctggaaaac ctttcccaga gcatacagct tagcaaaaag acagtgtttg | 2950 |
| tgatgacaga caagtatgca aagactgaaa attttaagat agcatttac | 3000 |
| ttgtcccatc agaggctcat ggatgaaaaa gttgatgtga ttatcttgat | 3050 |
| atttcttgag aagcccttc agaagtccaa gttcctccag ctccggaaaa | 3100 |
| ggctctgtgg gagttctgtc cttgagtggc aacaaaccc gcaagctcac | 3150 |
| ccatacttct ggcagtgtct aaagaacgcc ctggccacag acaatcatgt | 3200 |
| ggcctatagt caggtgttca aggaaacggt ctagcccttc tttgcaaaac | 3250 |
| acaactgcct agtttaccaa ggagaggcct ggc | 3283 |

<210> SEQ ID NO 3
<211> LENGTH: 1041
<212> TYPE: PRT
<213> ORGANISM: Homo sapiens

<400> SEQUENCE: 3

```
Met Glu Asn Met Phe Leu Gln Ser Ser Met Leu Thr Cys Ile Phe
  1               5                  10                  15

Leu Leu Ile Ser Gly Ser Cys Glu Leu Cys Ala Glu Glu Asn Phe
             20                  25                  30

Ser Arg Ser Tyr Pro Cys Asp Glu Lys Lys Gln Asn Asp Ser Val
             35                  40                  45

Ile Ala Glu Cys Ser Asn Arg Arg Leu Gln Glu Val Pro Gln Thr
             50                  55                  60

Val Gly Lys Tyr Val Thr Glu Leu Asp Leu Ser Asp Asn Phe Ile
             65                  70                  75

Thr His Ile Thr Asn Glu Ser Phe Gln Gly Leu Gln Asn Leu Thr
             80                  85                  90

Lys Ile Asn Leu Asn His Asn Pro Asn Val Gln His Gln Asn Gly
             95                 100                 105

Asn Pro Gly Ile Gln Ser Asn Gly Leu Asn Ile Thr Asp Gly Ala
            110                 115                 120

Phe Leu Asn Leu Lys Asn Leu Arg Glu Leu Leu Leu Glu Asp Asn
            125                 130                 135

Gln Leu Pro Gln Ile Pro Ser Gly Leu Pro Glu Ser Leu Thr Glu
            140                 145                 150
```

```
Leu Ser Leu Ile Gln Asn Asn Ile Tyr Asn Ile Thr Lys Glu Gly
            155                 160                 165

Ile Ser Arg Leu Ile Asn Leu Lys Asn Leu Tyr Leu Ala Trp Asn
            170                 175                 180

Cys Tyr Phe Asn Lys Val Cys Glu Lys Thr Asn Ile Glu Asp Gly
            185                 190                 195

Val Phe Glu Thr Leu Thr Asn Leu Glu Leu Leu Ser Leu Ser Phe
            200                 205                 210

Asn Ser Leu Ser His Val Pro Pro Lys Leu Pro Ser Ser Leu Arg
            215                 220                 225

Lys Leu Phe Leu Ser Asn Thr Gln Ile Lys Tyr Ile Ser Glu Glu
            230                 235                 240

Asp Phe Lys Gly Leu Ile Asn Leu Thr Leu Leu Asp Leu Ser Gly
            245                 250                 255

Asn Cys Pro Arg Cys Phe Asn Ala Pro Phe Pro Cys Val Pro Cys
            260                 265                 270

Asp Gly Gly Ala Ser Ile Asn Ile Asp Arg Phe Ala Phe Gln Asn
            275                 280                 285

Leu Thr Gln Leu Arg Tyr Leu Asn Leu Ser Ser Thr Ser Leu Arg
            290                 295                 300

Lys Ile Asn Ala Ala Trp Phe Lys Asn Met Pro His Leu Lys Val
            305                 310                 315

Leu Asp Leu Glu Phe Asn Tyr Leu Val Gly Glu Ile Val Ser Gly
            320                 325                 330

Ala Phe Leu Thr Met Leu Pro Arg Leu Glu Ile Leu Asp Leu Ser
            335                 340                 345

Phe Asn Tyr Ile Lys Gly Ser Tyr Pro Gln His Ile Asn Ile Ser
            350                 355                 360

Arg Asn Phe Ser Lys Leu Leu Ser Leu Arg Ala Leu His Leu Arg
            365                 370                 375

Gly Tyr Val Phe Gln Glu Leu Arg Glu Asp Asp Phe Gln Pro Leu
            380                 385                 390

Met Gln Leu Pro Asn Leu Ser Thr Ile Asn Leu Gly Ile Asn Phe
            395                 400                 405

Ile Lys Gln Ile Asp Phe Lys Leu Phe Gln Asn Phe Ser Asn Leu
            410                 415                 420

Glu Ile Ile Tyr Leu Ser Glu Asn Arg Ile Ser Pro Leu Val Lys
            425                 430                 435

Asp Thr Arg Gln Ser Tyr Ala Asn Ser Ser Ser Phe Gln Arg His
            440                 445                 450

Ile Arg Lys Arg Arg Ser Thr Asp Phe Glu Phe Asp Pro His Ser
            455                 460                 465

Asn Phe Tyr His Phe Thr Arg Pro Leu Ile Lys Pro Gln Cys Ala
            470                 475                 480

Ala Tyr Gly Lys Ala Leu Asp Leu Ser Leu Asn Ser Ile Phe Phe
            485                 490                 495

Ile Gly Pro Asn Gln Phe Glu Asn Leu Pro Asp Ile Ala Cys Leu
            500                 505                 510

Asn Leu Ser Ala Asn Ser Asn Ala Gln Val Leu Ser Gly Thr Glu
            515                 520                 525

Phe Ser Ala Ile Pro His Val Lys Tyr Leu Asp Leu Thr Asn Asn
            530                 535                 540

Arg Leu Asp Phe Asp Asn Ala Ser Ala Leu Thr Glu Leu Ser Asp
            545                 550                 555
```

```
Leu Glu Val Leu Asp Leu Ser Tyr Asn Ser His Tyr Phe Arg Ile
            560                 565                 570

Ala Gly Val Thr His His Leu Glu Phe Ile Gln Asn Phe Thr Asn
            575                 580                 585

Leu Lys Val Leu Asn Leu Ser His Asn Asn Ile Tyr Thr Leu Thr
            590                 595                 600

Asp Lys Tyr Asn Leu Glu Ser Lys Ser Leu Val Glu Leu Val Phe
            605                 610                 615

Ser Gly Asn Arg Leu Asp Ile Leu Trp Asn Asp Asp Asn Arg
            620                 625                 630

Tyr Ile Ser Ile Phe Lys Gly Leu Lys Asn Leu Thr Arg Leu Asp
            635                 640                 645

Leu Ser Leu Asn Arg Leu Lys His Ile Pro Asn Glu Ala Phe Leu
            650                 655                 660

Asn Leu Pro Ala Ser Leu Thr Glu Leu His Ile Asn Asp Asn Met
            665                 670                 675

Leu Lys Phe Phe Asn Trp Thr Leu Leu Gln Gln Phe Pro Arg Leu
            680                 685                 690

Glu Leu Leu Asp Leu Arg Gly Asn Lys Leu Leu Phe Leu Thr Asp
            695                 700                 705

Ser Leu Ser Asp Phe Thr Ser Ser Leu Arg Thr Leu Leu Leu Ser
            710                 715                 720

His Asn Arg Ile Ser His Leu Pro Ser Gly Phe Leu Ser Glu Val
            725                 730                 735

Ser Ser Leu Lys His Leu Asp Leu Ser Ser Asn Leu Leu Lys Thr
            740                 745                 750

Ile Asn Lys Ser Ala Leu Glu Thr Lys Thr Thr Thr Lys Leu Ser
            755                 760                 765

Met Leu Glu Leu His Gly Asn Pro Phe Glu Cys Thr Cys Asp Ile
            770                 775                 780

Gly Asp Phe Arg Arg Trp Met Asp Glu His Leu Asn Val Lys Ile
            785                 790                 795

Pro Arg Leu Val Asp Val Ile Cys Ala Ser Pro Gly Asp Gln Arg
            800                 805                 810

Gly Lys Ser Ile Val Ser Leu Glu Leu Thr Thr Cys Val Ser Asp
            815                 820                 825

Val Thr Ala Val Ile Leu Phe Phe Phe Thr Phe Phe Ile Thr Thr
            830                 835                 840

Met Val Met Leu Ala Ala Leu Ala His His Leu Phe Tyr Trp Asp
            845                 850                 855

Val Trp Phe Ile Tyr Asn Val Cys Leu Ala Lys Val Lys Gly Tyr
            860                 865                 870

Arg Ser Leu Ser Thr Ser Gln Thr Phe Tyr Asp Ala Tyr Ile Ser
            875                 880                 885

Tyr Asp Thr Lys Asp Ala Ser Val Thr Asp Trp Val Ile Asn Glu
            890                 895                 900

Leu Arg Tyr His Leu Glu Glu Ser Arg Asp Lys Asn Val Leu Leu
            905                 910                 915

Cys Leu Glu Glu Arg Asp Trp Asp Pro Gly Leu Ala Ile Ile Asp
            920                 925                 930

Asn Leu Met Gln Ser Ile Asn Gln Ser Lys Lys Thr Val Phe Val
            935                 940                 945

Leu Thr Lys Lys Tyr Ala Lys Ser Trp Asn Phe Lys Thr Ala Phe
```

```
                       950            955             960
Tyr Leu Ala Leu Gln Arg Leu Met Asp Glu Asn Met Asp Val Ile
                965                970                 975
Ile Phe Ile Leu Leu Glu Pro Val Leu Gln His Ser Gln Tyr Leu
                980                985                 990
Arg Leu Arg Gln Arg Ile Cys Lys Ser Ser Ile Leu Gln Trp Pro
                995               1000                1005
Asp Asn Pro Lys Ala Glu Gly Leu Phe Trp Gln Thr Leu Arg Asn
               1010               1015                1020
Val Val Leu Thr Glu Asn Asp Ser Arg Tyr Asn Asn Met Tyr Val
               1025               1030                1035
Asp Ser Ile Lys Gln Tyr
               1040

<210> SEQ ID NO 4
<211> LENGTH: 4199
<212> TYPE: DNA
<213> ORGANISM: Homo sapiens

<400> SEQUENCE: 4
gggtaccatt ctgcgctgct gcaagttacg gaatgaaaaa ttagaacaac            50
agaaacatgg aaaacatgtt ccttcagtcg tcaatgctga cctgcatttt           100
cctgctaata tctggttcct gtgagttatg cgccgaagaa aatttttcta           150
gaagctatcc ttgtgatgag aaaaagcaaa atgactcagt tattgcagag           200
tgcagcaatc gtcgactaca ggaagttccc caaacggtgg gcaaatatgt           250
gacagaacta gacctgtctg ataatttcat cacacacata acgaatgaat           300
catttcaagg gctgcaaaat ctcactaaaa taaatctaaa ccacaacccc           350
aatgtacagc accagaacgg aaatcccggt atacaatcaa atggcttgaa           400
tatcacagac ggggcattcc tcaacctaaa aaacctaagg gagttactgc           450
ttgaagacaa ccagttaccc caaataccct ctggtttgcc agagtctttg           500
acagaactta gtctaattca aaacaatata tacaacataa ctaaagaggg           550
catttcaaga cttataaact tgaaaaatct ctatttggcc tggaactgct           600
attttaacaa agtttgcgag aaaactaaca tagaagatgg agtatttgaa           650
acgctgacaa atttggagtt gctatcacta tctttcaatt ctctttcaca           700
cgtgccaccc aaactgccaa gctccctacg caaactttt ctgagcaaca            750
cccagatcaa atacattagt gaagaagatt tcaagggatt gataaattta           800
acattactag atttaagcgg gaactgtccg aggtgcttca atgccccatt           850
tccatgcgtg ccttgtgatg gtggtgcttc aattaatata gatcgttttg           900
cttttcaaaa cttgacccaa cttcgatacc taaacctctc tagcacttcc           950
ctcaggaaga ttaatgctgc ctggtttaaa aatatgcctc atctgaaggt          1000
gctggatctt gaattcaact atttagtggg agaaatagtc tctggggcat          1050
ttttaacgat gctgccccgc ttagaaatac ttgacttgtc ttttaactat          1100
ataaagggga gttatccaca gcatattaat atttccagaa acttctctaa          1150
actttttgtct ctacgggcat tgcatttaag aggttatgtg ttccaggaac         1200
tcagagaaga tgattccag ccctgatgc agcttccaaa cttatcgact            1250
atcaacttgg gtattaattt tattaagcaa atcgatttca aacttttcca          1300
```

```
aaatttctcc aatctggaaa ttatttactt gtcagaaaac agaatatcac      1350
cgttggtaaa agatacccgg cagagttatg caaatagttc ctcttttcaa      1400
cgtcatatcc ggaaacgacg ctcaacagat tttgagtttg acccacattc      1450
gaactttttat catttcaccc gtcctttaat aaagccacaa tgtgctgctt     1500
atggaaaagc cttagattta agcctcaaca gtattttctt cattgggcca      1550
aaccaatttg aaaatcttcc tgacattgcc tgtttaaatc tgtctgcaaa      1600
tagcaatgct caagtgttaa gtggaactga attttcagcc attcctcatg      1650
tcaaatattt ggatttgaca aacaatagac tagactttga taatgctagt      1700
gctcttactg aattgtccga cttggaagtt ctagatctca gctataattc      1750
acactatttc agaatagcag gcgtaacaca tcatctagaa tttattcaaa      1800
atttcacaaa tctaaaagtt ttaaacttga gccacaacaa catttatact      1850
ttaacagata agtataacct ggaaagcaag tccctggtag aattagtttt      1900
cagtggcaat cgccttgaca ttttgtggaa tgatgatgac aacaggtata      1950
tctccatttt caaaggtctc aagaatctga cacgtctgga tttatccctt      2000
aataggctga agcacatccc aaatgaagca ttccttaatt tgccagcgag      2050
tctcactgaa ctacatataa atgataatat gttaaagttt tttaactgga      2100
cattactcca gcagtttcct cgtctcgagt tgcttgactt acgtggaaac      2150
aaactactct tttaactga tagcctatct gactttacat cttcccttcg       2200
gacactgctg ctgagtcata acaggatttc ccacctaccc tctggctttc      2250
tttctgaagt cagtagtctg aagcaccctg atttaagttc caatctgcta      2300
aaaacaatca acaaatccgc acttgaaact aagaccacca ccaaattatc      2350
tatgttggaa ctacacggaa accccttga atgcacctgt gacattggag       2400
atttccgaag atggatggat gaacatctga atgtcaaaat tcccagactg      2450
gtagatgtca tttgtgccag tcctggggat caaagaggga agagtattgt      2500
gagtctggag ctaacaactt gtgtttcaga tgtcactgca gtgatattat      2550
ttttcttcac gttctttatc accaccatgg ttatgttggc tgccctggct      2600
caccattgt tttactggga tgtttggttt atatataatg tgtgtttagc       2650
taaggtaaaa ggctacaggt ctcttttccac atcccaaaact ttctatgatg    2700
cttacatttc ttatgacacc aaagatgcct ctgttactga ctgggtgata      2750
aatgagctgc gctaccacct tgaagagagc cgagacaaaa acgttctcct      2800
ttgtctagag gagagggatt gggacccggg attggccatc atcgacaacc      2850
tcatgcagag catcaaccaa agcaagaaaa cagtatttgt tttaaccaaa      2900
aaatatgcaa aaagctggaa ctttaaaaca gcttttttact tggctttgca    2950
gaggctaatg gatgagaaca tggatgtgat tatatttatc ctgctggagc      3000
cagtgttaca gcattctcag tatttgaggc tacggcagcg gatctgtaag      3050
agctccatcc tccagtggcc tgacaacccg aaggcagaag gcttgttttg      3100
gcaaactctg agaaatgtgg tcttgactga aaatgattca cggtataaca      3150
atatgtatgt cgattccatt aagcaatact aactgacgtt aagtcatgat      3200
ttcgcgccat aataaagatg caaaggaatg acatttctgt attagttatc      3250
tattgctatg taacaaatta tcccaaaact tagtggttta aaacaacaca      3300
```

```
tttgctggcc cacagttttt gagggtcagg agtccaggcc cagcataact         3350
gggtcctctg ctcagggtgt ctcagaggct gcaatgtagg tgttcaccag         3400
agacataggc atcactgggg tcacactcat gtggttgttt tctggattca         3450
attcctcctg ggctattggc caaaggctat actcatgtaa gccatgcgag         3500
cctctcccac aaggcagctt gcttcatcag agctagcaaa aaagagaggt         3550
tgctagcaag atgaagtcac aatcttttgt aatcgaatca aaaaagtgat         3600
atctcatcac tttggccata ttctatttgt tagaagtaaa ccacaggtcc         3650
caccagctcc atgggagtga ccacctcagt ccagggaaaa cagctgaaga         3700
ccaagatggt gagctctgat tgcttcagtt ggtcatcaac tattttccct         3750
tgactgctgt cctgggatgg cctgctatct tgatgataga ttgtgaatat         3800
caggaggcag ggatcactgt ggaccatctt agcagttgac ctaacacatc         3850
ttcttttcaa tatctaagaa cttttgccac tgtgactaat ggtcctaata         3900
ttaagctgtt gtttatattt atcatatatc tatggctaca tggttatatt         3950
atgctgtggt tgcgttcggt tttatttaca gttgctttta caaatatttg         4000
ctgtaacatt tgacttctaa ggtttagatg ccatttaaga actgagatgg         4050
atagctttta aagcatcttt tacttcttac cattttttaa aagtatgcag         4100
ctaaattcga agcttttggt ctatattgtt aattgccatt gctgtaaatc         4150
ttaaaatgaa tgaataaaaa tgtttcattt tacaaaaaaa aaaaaaaa           4199
```

<210> SEQ ID NO 5
<211> LENGTH: 20
<212> TYPE: DNA
<213> ORGANISM: Homo sapiens

<400> SEQUENCE: 5
taaagaccca gctgtgaccg                                            20

<210> SEQ ID NO 6
<211> LENGTH: 20
<212> TYPE: DNA
<213> ORGANISM: Homo sapiens

<400> SEQUENCE: 6
atccatgagc ctctgatggg                                            20

<210> SEQ ID NO 7
<211> LENGTH: 45
<212> TYPE: DNA
<213> ORGANISM: Homo sapiens

<400> SEQUENCE: 7
atttatgtct cgaggaaagg gactggttac cagggcagcc agttc                45

<210> SEQ ID NO 8
<211> LENGTH: 21
<212> TYPE: DNA
<213> ORGANISM: Homo sapiens

<400> SEQUENCE: 8
gccgagacaa aaacgttctc c                                          21

<210> SEQ ID NO 9
<211> LENGTH: 24
<212> TYPE: DNA

<213> ORGANISM: Homo sapiens

<400> SEQUENCE: 9
catccatgtt ctcatccatt agcc                                                    24

<210> SEQ ID NO 10
<211> LENGTH: 46
<212> TYPE: DNA
<213> ORGANISM: Homo sapiens

<400> SEQUENCE: 10
tcgacaacct catgcagagc atcaaccaaa gcaagaaaac agtatt                            46

<210> SEQ ID NO 11
<211> LENGTH: 2602
<212> TYPE: DNA
<213> ORGANISM: Homo sapiens

<400> SEQUENCE: 11
gttatgccta gaaacatttt ctcaagaatt agaattacga tatgctgtca                        50
aacacaatga cttatttgaa cctctttat ttgtaggttg aagcactgga                        100
caatgccaca tactttgtgg atggtgtggg tcttgggggt catcatcagc                        150
ctctccaagg aagaatcctc caatcaggct tctctgtctt gtgaccgcaa                        200
tggtatctgc aagggcagct caggatcttt aaactccatt ccctcagggc                        250
tcacagaagc tgtaaaaagc cttgacctgt ccaacaacag gatcacctac                        300
attagcaaca gtgacctaca gaggtgtgtg aacctccagg ctctggtgct                        350
gacatccaat ggaattaaca aatagagga agattcttt tcttccctgg                          400
gcagtcttga acatttagac ttatcctata attacttatc taatttatcg                        450
tcttcctggt tcaagcccct ttcttcttta acattcttaa acttactggg                        500
aaatccttac aaaaccctag gggaaacatc tctttttct catctcacaa                         550
aattgcaaat cctgagagtg ggaaatatgg acaccttcac taagattcaa                        600
agaaaagatt ttgctggact taccttcctt gaggaacttg agattgatgc                        650
ttcagatcta cagagctatg agccaaaaag tttgaagtca attcagaatg                        700
taagtcatct gatccttcat atgaagcagc atattttact gctggagatt                        750
tttgtagatg ttacaagttc cgtggaatgt ttggaactgc gagatactga                        800
tttggacact ttccattttt cagaactatc cactggtgaa acaaattcat                        850
tgattaaaaa gtttacattt agaaatgtga aaatcaccga tgaaagtttg                        900
tttcaggtta tgaaactttt gaatcagatt tctggattgt tagaattaga                        950
gtttgatgac tgtacccta tggagttgg taatttaga gcatctgata                           1000
atgacagagt tatagatcca ggtaaagtgg aaacgttaac aatccggagg                        1050
ctgcatattc caaggtttta cttatttat gatctgagca ctttatattc                         1100
acttacagaa agagttaaaa gaatcacagt agaaaacagt aaagtttttc                        1150
tggttccttg tttacttca caacatttaa aatcattaga atacttggat                         1200
ctcagtgaaa atttgatggt tgaagaatac ttgaaaaatt cagcctgtga                        1250
ggatgcctgg ccctctctac aaactttaat tttaaggcaa aatcatttgg                        1300
catcattgga aaaaccgga gagactttgc tcactctgaa aaacttgact                         1350
aacattgata tcagtaagaa tagttttcat tctatgcctg aaacttgtca                        1400

| | |
|---|---|
| gtggccagaa aagatgaaat atttgaactt atccagcaca cgaatacaca | 1450 |
| gtgtaacagg ctgcattccc aagacactgg aaatttagat gttagcaac | 1500 |
| aacaatctca atttattttc tttgaatttg ccgcaactca agaactta | 1550 |
| tatttccaga aataagttga tgactctacc agatgcctcc ctcttaccca | 1600 |
| tgttactagt attgaaaatc agtaggaatg caataactac gttttctaag | 1650 |
| gagcaacttg actcatttca cacactgaag actttggaag ctggtggcaa | 1700 |
| taacttcatt tgctcctgtg aattcctctc cttcactcag gagcagcaag | 1750 |
| cactggccaa agtcttgatt gattggccag caaattacct gtgtgactct | 1800 |
| ccatcccatg tgcgtggcca gcaggttcag gatgtccgcc tctcggtgtc | 1850 |
| ggaatgtcac aggacagcac tggtgtctgg catgtgctgt gctctgttcc | 1900 |
| tgctgatcct gctcacgggg gtcctgtgcc accgtttcca tggcctgtgg | 1950 |
| tatatgaaaa tgatgtgggc ctggctccag gccaaaagga agcccaggaa | 2000 |
| agctcccagc aggaacatct gctatgatgc atttgtttct tacagtgagc | 2050 |
| gggatgccta ctgggtggag aaccttatgg tccaggagct ggagaacttc | 2100 |
| aatccccct tcaagttgtg tcttcataag cgggacttca ttcctggcaa | 2150 |
| gtggatcatt gacaatatca ttgactccat tgaaaagagc cacaaaactg | 2200 |
| tctttgtgct ttctgaaaac tttgtgaaga gtgagtggtg caagtatgaa | 2250 |
| ctggacttct cccatttccg tcttttgat gagaacaatg atgctgccat | 2300 |
| tctcattctt ctggagccca ttgagaaaaa agccattccc cagcgcttct | 2350 |
| gcaagctgcg gaagataatg aacaccaaga cctacctgga gtggcccatg | 2400 |
| gacgaggctc agcgggaagg atttgggta aatctgagag ctgcgataaa | 2450 |
| gtcctaggtt cccatattta agaccagtct tgtctagtt gggatcttta | 2500 |
| tgtcactagt tatagttaag ttcattcaga cataattata taaaaactac | 2550 |
| gtggatgtac cgtcatttga ggacttgctt actaaaacta caaaacttca | 2600 |
| aa | 2602 |

<210> SEQ ID NO 12
<211> LENGTH: 784
<212> TYPE: PRT
<213> ORGANISM: Homo sapiens

<400> SEQUENCE: 12

```
Met Pro His Thr Leu Trp Met Val Trp Val Leu Gly Val Ile Ile
  1               5                  10                  15

Ser Leu Ser Lys Glu Glu Ser Ser Asn Gln Ala Ser Leu Ser Cys
                 20                  25                  30

Asp Arg Asn Gly Ile Cys Lys Gly Ser Ser Gly Ser Leu Asn Ser
                 35                  40                  45

Ile Pro Ser Gly Leu Thr Glu Ala Val Lys Ser Leu Asp Leu Ser
                 50                  55                  60

Asn Asn Arg Ile Thr Tyr Ile Ser Asn Ser Asp Leu Gln Arg Cys
                 65                  70                  75

Val Asn Leu Gln Ala Leu Val Leu Thr Ser Asn Gly Ile Asn Thr
                 80                  85                  90

Ile Glu Glu Asp Ser Phe Ser Ser Leu Gly Ser Leu Glu His Leu
                 95                 100                 105

Asp Leu Ser Tyr Asn Tyr Leu Ser Asn Leu Ser Ser Ser Trp Phe
```

-continued

```
                    110                 115                 120
Lys Pro Leu Ser Ser Leu Thr Phe Leu Asn Leu Leu Gly Asn Pro
                125                 130                 135
Tyr Lys Thr Leu Gly Glu Thr Ser Leu Phe Ser His Leu Thr Lys
                140                 145                 150
Leu Gln Ile Leu Arg Val Gly Asn Met Asp Thr Phe Thr Lys Ile
                155                 160                 165
Gln Arg Lys Asp Phe Ala Gly Leu Thr Phe Leu Glu Glu Leu Glu
                170                 175                 180
Ile Asp Ala Ser Asp Leu Gln Ser Tyr Glu Pro Lys Ser Leu Lys
                185                 190                 195
Ser Ile Gln Asn Val Ser His Leu Ile Leu His Met Lys Gln His
                200                 205                 210
Ile Leu Leu Leu Glu Ile Phe Val Asp Val Thr Ser Ser Val Glu
                215                 220                 225
Cys Leu Glu Leu Arg Asp Thr Asp Leu Asp Thr Phe His Phe Ser
                230                 235                 240
Glu Leu Ser Thr Gly Glu Thr Asn Ser Leu Ile Lys Lys Phe Thr
                245                 250                 255
Phe Arg Asn Val Lys Ile Thr Asp Glu Ser Leu Phe Gln Val Met
                260                 265                 270
Lys Leu Leu Asn Gln Ile Ser Gly Leu Leu Glu Leu Glu Phe Asp
                275                 280                 285
Asp Cys Thr Leu Asn Gly Val Gly Asn Phe Arg Ala Ser Asp Asn
                290                 295                 300
Asp Arg Val Ile Asp Pro Gly Lys Val Glu Thr Leu Thr Ile Arg
                305                 310                 315
Arg Leu His Ile Pro Arg Phe Tyr Leu Phe Tyr Asp Leu Ser Thr
                320                 325                 330
Leu Tyr Ser Leu Thr Glu Arg Val Lys Arg Ile Thr Val Glu Asn
                335                 340                 345
Ser Lys Val Phe Leu Val Pro Cys Leu Leu Ser Gln His Leu Lys
                350                 355                 360
Ser Leu Glu Tyr Leu Asp Leu Ser Glu Asn Leu Met Val Glu Glu
                365                 370                 375
Tyr Leu Lys Asn Ser Ala Cys Glu Asp Ala Trp Pro Ser Leu Gln
                380                 385                 390
Thr Leu Ile Leu Arg Gln Asn His Leu Ala Ser Leu Glu Lys Thr
                395                 400                 405
Gly Glu Thr Leu Leu Thr Leu Lys Asn Leu Thr Asn Ile Asp Ile
                410                 415                 420
Ser Lys Asn Ser Phe His Ser Met Pro Glu Thr Cys Gln Trp Pro
                425                 430                 435
Glu Lys Met Lys Tyr Leu Asn Leu Ser Ser Thr Arg Ile His Ser
                440                 445                 450
Val Thr Gly Cys Ile Pro Lys Thr Leu Glu Ile Leu Asp Val Ser
                455                 460                 465
Asn Asn Asn Leu Asn Leu Phe Ser Leu Asn Leu Pro Gln Leu Lys
                470                 475                 480
Glu Leu Tyr Ile Ser Arg Asn Lys Leu Met Thr Leu Pro Asp Ala
                485                 490                 495
Ser Leu Leu Pro Met Leu Leu Val Leu Lys Ile Ser Arg Asn Ala
                500                 505                 510
```

```
Ile Thr Thr Phe Ser Lys Glu Gln Leu Asp Ser Phe His Thr Leu
            515                 520                 525

Lys Thr Leu Glu Ala Gly Gly Asn Asn Phe Ile Cys Ser Cys Glu
            530                 535                 540

Phe Leu Ser Phe Thr Gln Glu Gln Gln Ala Leu Ala Lys Val Leu
            545                 550                 555

Ile Asp Trp Pro Ala Asn Tyr Leu Cys Asp Ser Pro Ser His Val
            560                 565                 570

Arg Gly Gln Gln Val Gln Asp Val Arg Leu Ser Val Ser Glu Cys
            575                 580                 585

His Arg Thr Ala Leu Val Ser Gly Met Cys Cys Ala Leu Phe Leu
            590                 595                 600

Leu Ile Leu Leu Thr Gly Val Leu Cys His Arg Phe His Gly Leu
            605                 610                 615

Trp Tyr Met Lys Met Met Trp Ala Trp Leu Gln Ala Lys Arg Lys
            620                 625                 630

Pro Arg Lys Ala Pro Ser Arg Asn Ile Cys Tyr Asp Ala Phe Val
            635                 640                 645

Ser Tyr Ser Glu Arg Asp Ala Tyr Trp Val Glu Asn Leu Met Val
            650                 655                 660

Gln Glu Leu Glu Asn Phe Asn Pro Pro Phe Lys Leu Cys Leu His
            665                 670                 675

Lys Arg Asp Phe Ile Pro Gly Lys Trp Ile Ile Asp Asn Ile Ile
            680                 685                 690

Asp Ser Ile Glu Lys Ser His Lys Thr Val Phe Val Leu Ser Glu
            695                 700                 705

Asn Phe Val Lys Ser Glu Trp Cys Lys Tyr Glu Leu Asp Phe Ser
            710                 715                 720

His Phe Arg Leu Phe Asp Glu Asn Asn Asp Ala Ala Ile Leu Ile
            725                 730                 735

Leu Leu Glu Pro Ile Glu Lys Lys Ala Ile Pro Gln Arg Phe Cys
            740                 745                 750

Lys Leu Arg Lys Ile Met Asn Thr Lys Thr Tyr Leu Glu Trp Pro
            755                 760                 765

Met Asp Glu Ala Gln Arg Glu Gly Phe Trp Val Asn Leu Arg Ala
            770                 775                 780

Ala Ile Lys Ser

<210> SEQ ID NO 13
<211> LENGTH: 811
<212> TYPE: PRT
<213> ORGANISM: Homo sapiens

<400> SEQUENCE: 13

Met Arg Leu Ile Arg Asn Ile Tyr Ile Phe Cys Ser Ile Val Met
 1               5                  10                  15

Thr Ala Glu Gly Asp Ala Pro Glu Leu Pro Glu Glu Arg Glu Leu
            20                  25                  30

Met Thr Asn Cys Ser Asn Met Ser Leu Arg Lys Val Pro Ala Asp
            35                  40                  45

Leu Thr Pro Ala Thr Thr Thr Leu Asp Leu Ser Tyr Asn Leu Leu
            50                  55                  60

Phe Gln Leu Gln Ser Ser Asp Phe His Ser Val Ser Lys Leu Arg
            65                  70                  75

Val Leu Ile Leu Cys His Asn Arg Ile Gln Gln Leu Asp Leu Lys
```

-continued

```
                80                  85                  90
Thr Phe Glu Phe Asn Lys Glu Leu Arg Tyr Leu Asp Leu Ser Asn
                95                 100                 105
Asn Arg Leu Lys Ser Val Thr Trp Tyr Leu Leu Ala Gly Leu Arg
               110                 115                 120
Tyr Leu Asp Leu Ser Phe Asn Asp Phe Asp Thr Met Pro Ile Cys
               125                 130                 135
Glu Glu Ala Gly Asn Met Ser His Leu Glu Ile Leu Gly Leu Ser
               140                 145                 150
Gly Ala Lys Ile Gln Lys Ser Asp Phe Gln Lys Ile Ala His Leu
               155                 160                 165
His Leu Asn Thr Val Phe Leu Gly Phe Arg Thr Leu Pro His Tyr
               170                 175                 180
Glu Glu Gly Ser Leu Pro Ile Leu Asn Thr Thr Lys Leu His Ile
               185                 190                 195
Val Leu Pro Met Asp Thr Asn Phe Trp Val Leu Leu Arg Asp Gly
               200                 205                 210
Ile Lys Thr Ser Lys Ile Leu Glu Met Thr Asn Ile Asp Gly Lys
               215                 220                 225
Ser Gln Phe Val Ser Tyr Glu Met Gln Arg Asn Leu Ser Leu Glu
               230                 235                 240
Asn Ala Lys Thr Ser Val Leu Leu Leu Asn Lys Val Asp Leu Leu
               245                 250                 255
Trp Asp Asp Leu Phe Leu Ile Leu Gln Phe Val Trp His Thr Ser
               260                 265                 270
Val Glu His Phe Gln Ile Arg Asn Val Thr Phe Gly Gly Lys Ala
               275                 280                 285
Tyr Leu Asp His Asn Ser Phe Asp Tyr Ser Asn Thr Val Met Arg
               290                 295                 300
Thr Ile Lys Leu Glu His Val His Phe Arg Val Phe Tyr Ile Gln
               305                 310                 315
Gln Asp Lys Ile Tyr Leu Leu Leu Thr Lys Met Asp Ile Glu Asn
               320                 325                 330
Leu Thr Ile Ser Asn Ala Gln Met Pro His Met Leu Phe Pro Asn
               335                 340                 345
Tyr Pro Thr Lys Phe Gln Tyr Leu Asn Phe Ala Asn Asn Ile Leu
               350                 355                 360
Thr Asp Glu Leu Phe Lys Arg Thr Ile Gln Leu Pro His Leu Lys
               365                 370                 375
Thr Leu Ile Leu Asn Gly Asn Lys Leu Glu Thr Leu Ser Leu Val
               380                 385                 390
Ser Cys Phe Ala Asn Asn Thr Pro Leu Glu His Leu Asp Leu Ser
               395                 400                 405
Gln Asn Leu Leu Gln His Lys Asn Asp Glu Asn Cys Ser Trp Pro
               410                 415                 420
Glu Thr Val Val Asn Met Asn Leu Ser Tyr Asn Lys Leu Ser Asp
               425                 430                 435
Ser Val Phe Arg Cys Leu Pro Lys Ser Ile Gln Ile Leu Asp Leu
               440                 445                 450
Asn Asn Asn Gln Ile Gln Thr Val Pro Lys Glu Thr Ile His Leu
               455                 460                 465
Met Ala Leu Arg Glu Leu Asn Ile Ala Phe Asn Phe Leu Thr Asp
               470                 475                 480
```

| | | | | | | | | | | |
|---|---|---|---|---|---|---|---|---|---|---|
|Leu|Pro|Gly|Cys|Ser|His|Phe|Ser|Arg|Leu|Ser|Val|Leu|Asn|Ile|
| | | | |485| | | |490| | | | | |495|

Glu Met Asn Phe Ile Leu Ser Pro Ser Leu Asp Phe Val Gln Ser
                500                 505                 510

Cys Gln Glu Val Lys Thr Leu Asn Ala Gly Arg Asn Pro Phe Arg
                515                 520                 525

Cys Thr Cys Glu Leu Lys Asn Phe Ile Gln Leu Glu Thr Tyr Ser
                530                 535                 540

Glu Val Met Met Val Gly Trp Ser Asp Ser Tyr Thr Cys Glu Tyr
                545                 550                 555

Pro Leu Asn Leu Arg Gly Thr Arg Leu Lys Asp Val His Leu His
                560                 565                 570

Glu Leu Ser Cys Asn Thr Ala Leu Leu Ile Val Thr Ile Val Val
                575                 580                 585

Ile Met Leu Val Leu Gly Leu Ala Val Ala Phe Cys Cys Leu His
                590                 595                 600

Phe Asp Leu Pro Trp Tyr Leu Arg Met Leu Gly Gln Cys Thr Gln
                605                 610                 615

Thr Trp His Arg Val Arg Lys Thr Thr Gln Glu Gln Leu Lys Arg
                620                 625                 630

Asn Val Arg Phe His Ala Phe Ile Ser Tyr Ser Glu His Asp Ser
                635                 640                 645

Leu Trp Val Lys Asn Glu Leu Ile Pro Asn Leu Glu Lys Glu Asp
                650                 655                 660

Gly Ser Ile Leu Ile Cys Leu Tyr Glu Ser Tyr Phe Asp Pro Gly
                665                 670                 675

Lys Ser Ile Ser Glu Asn Ile Val Ser Phe Ile Glu Lys Ser Tyr
                680                 685                 690

Lys Ser Ile Phe Val Leu Ser Pro Asn Phe Val Gln Asn Glu Trp
                695                 700                 705

Cys His Tyr Glu Phe Tyr Phe Ala His His Asn Leu Phe His Glu
                710                 715                 720

Asn Ser Asp His Ile Ile Leu Ile Leu Leu Glu Pro Ile Pro Phe
                725                 730                 735

Tyr Cys Ile Pro Thr Arg Tyr His Lys Leu Lys Ala Leu Leu Glu
                740                 745                 750

Lys Lys Ala Tyr Leu Glu Trp Pro Lys Asp Arg Arg Lys Cys Gly
                755                 760                 765

Leu Phe Trp Ala Asn Leu Arg Ala Ala Ile Asn Val Asn Val Leu
                770                 775                 780

Ala Thr Arg Glu Met Tyr Glu Leu Gln Thr Phe Thr Glu Leu Asn
                785                 790                 795

Glu Glu Ser Arg Gly Ser Thr Ile Ser Leu Met Arg Thr Asp Cys
                800                 805                 810

Leu

<210> SEQ ID NO 14
<211> LENGTH: 3462
<212> TYPE: DNA
<213> ORGANISM: Homo sapiens

<400> SEQUENCE: 14
gaatcatcca cgcacctgca gctctgctga gagagtgcaa gccgtggggg        50
ttttgagctc atcttcatca ttcatatgag gaaataagtg gtaaaatcct        100

-continued

| | |
|---|---|
| tggaaataca atgagactca tcagaaacat ttacatattt tgtagtattg | 150 |
| ttatgacagc agagggtgat gctccagagc tgccagaaga aagggaactg | 200 |
| atgaccaact gctccaacat gtctctaaga aaggttcccg cagacttgac | 250 |
| cccagccaca acgacactgg atttatccta taacctcctt tttcaactcc | 300 |
| agagttcaga ttttcattct gtctccaaac tgagagtttt gattctatgc | 350 |
| cataacagaa ttcaacagct ggatctcaaa acctttgaat tcaacaagga | 400 |
| gttaagatat ttagatttgt ctaataacag actgaagagt gtaacttggt | 450 |
| atttactggc aggtctcagg tatttagatc tttcttttaa tgactttgac | 500 |
| accatgccta tctgtgagga agctggcaac atgtcacacc tggaaatcct | 550 |
| aggtttgagt ggggcaaaaa tacaaaaatc agatttccag aaaattgctc | 600 |
| atctgcatct aaatactgtc ttcttaggat tcagaactct tcctcattat | 650 |
| gaagaaggta gcctgcccat cttaaacaca acaaaactgc acattgtttt | 700 |
| accaatggac acaaatttct gggttctttt gcgtgatgga atcaagactt | 750 |
| caaaaatatt agaatgaca atatagatg gcaaaagcca atttgtaagt | 800 |
| tatgaaatgc aacgaaatct tagtttagaa aatgctaaga catcggttct | 850 |
| attgcttaat aaagttgatt tactctggga cgacctttc cttatcttac | 900 |
| aatttgtttg gcatacatca gtggaacact ttcagatccg aaatgtgact | 950 |
| tttggtggta aggcttatct tgaccacaat tcatttgact actcaaatac | 1000 |
| tgtaatgaga actataaaat tggagcatgt acatttcaga gtgttttaca | 1050 |
| ttcaacagga taaatctat ttgcttttga ccaaaatgga catagaaaac | 1100 |
| ctgacaatat caaatgcaca aatgccacac atgcttttcc cgaattatcc | 1150 |
| tacgaaattc caatatttaa attttgccaa taatatctta acagacgagt | 1200 |
| tgtttaaaag aactatccaa ctgcctcact tgaaaactct cattttgaat | 1250 |
| ggcaataaac tggagacact ttctttagta agttgctttg ctaacaacac | 1300 |
| acccttggaa cacttggatc tgagtcaaaa tctattacaa cataaaaatg | 1350 |
| atgaaaattg ctcatggcca gaaactgtgg tcaatatgaa tctgtcatac | 1400 |
| aataaattgt ctgattctgt cttcaggtgc ttgcccaaaa gtattcaaat | 1450 |
| acttgaccta ataataacc aaatccaaac tgtacctaaa gagactattc | 1500 |
| atctgatggc cttacgagaa ctaaatattg catttaattt tctaactgat | 1550 |
| ctccctggat gcagtcattt cagtagactt tcagttctga acattgaaat | 1600 |
| gaacttcatt ctcagcccat ctctggattt tgttcagagc tgccaggaag | 1650 |
| ttaaaactct aaatgcggga agaaatccat tccggtgtac ctgtgaatta | 1700 |
| aaaaatttca ttcagcttga aacatattca gaggtcatga tggttggatg | 1750 |
| gtcagattca tacacctgtg aatacccttt aaacctaagg ggaactaggt | 1800 |
| taaaagacgt tcatctccac gaattatctt gcaacacagc tctgttgatt | 1850 |
| gtcaccattg tggttattat gctagttctg gggttggctg tggccttctg | 1900 |
| ctgtctccac tttgatctgc cctggtatct caggatgcta ggtcaatgca | 1950 |
| cacaaacatg gcacagggtt aggaaaacaa cccaagaaca actcaagaga | 2000 |
| aatgtccgat tccacgcatt tatttcatac agtgaacatg attctctgtg | 2050 |
| ggtgaagaat gaattgatcc ccaatctaga gaaggaagat ggttctatct | 2100 |

```
tgatttgcct ttatgaaagc tactttgacc ctggcaaaag cattagtgaa      2150
aatattgtaa gcttcattga gaaaagctat aagtccatct ttgttttgtc      2200
tcccactttt gtccagaatg agtggtgcca ttatgaattc tactttgccc      2250
accacaatct cttccatgaa aattctgatc atataattct tatcttactg      2300
gaacccattc cattctattg cattcccacc aggtatcata aactgaaagc      2350
tctcctggaa aaaaagcat acttggaatg gcccaaggat aggcgtaaat       2400
gtgggctttt ctgggcaaac cttcgagctg ctattaatgt taatgtatta      2450
gccaccagag aaatgtatga actgcagaca ttcacagagt taaatgaaga      2500
gtctcgaggt tctacaatct ctctgatgag aacagattgt ctataaaatc      2550
ccacagtcct tgggaagttg gggaccacat acactgttgg gatgtacatt      2600
gatacaacct ttatgatggc aatttgacaa tatttattaa aataaaaaat      2650
ggttattccc ttcatatcag tttctagaag gatttctaag aatgtatcct      2700
atagaaacac cttcacaagt ttataagggc ttatggaaaa aggtgttcat      2750
cccaggattg tttataatca tgaaaaatgt ggccaggtgc agtggctcac      2800
tcttgtaatc ccagcactat gggaggccaa ggtgggtgac ccacgaggtc      2850
aagagatgga gaccatcctg gccaacatgg tgaaaccctg tctctactaa      2900
aaatacaaaa attagctggg cgtgatggtg cacgcctgta gtcccagcta      2950
cttgggaggc tgaggcagga gaatcgcttg aacccgggag gtggcagttg      3000
cagtgagctg agatcgagcc actgcactcc agcctggtga cagagcgaga      3050
ctccatctca aaaaaagaa aaaaaaaaa gaaaaaatg gaaacatcc           3100 tcatggccac aaaataaggt ctaattcaat aaattatagt acattaatgt      3150
aatataatat tacatgccac taaaaagaat aaggtagctg tatatttcct      3200
ggtatggaaa aaacatatta atatgttata aactattagg ttggtgcaaa      3250
actaattgtg gtttttgcca ttgaaatggc attgaaataa agtgtaaag       3300 aaatctatac cagatgtagt aacagtggtt tgggtctggg aggttggatt      3350
acagggagca tttgatttct atgttgtgta tttctataat gtttgaattg      3400
tttagaatga atctgtattt cttttataag tagaaaaaaa ataaagatag      3450
tttttacagc ct                                               3462

<210> SEQ ID NO 15
<211> LENGTH: 24
<212> TYPE: DNA
<213> ORGANISM: Homo sapiens

<400> SEQUENCE: 15
tcccaccagg tatcataaac tgaa                                  24

<210> SEQ ID NO 16
<211> LENGTH: 27
<212> TYPE: DNA
<213> ORGANISM: Homo sapiens

<400> SEQUENCE: 16
ttatagacaa tctgttctca tcagaga                               27

<210> SEQ ID NO 17
<211> LENGTH: 40
<212> TYPE: DNA
```

<213> ORGANISM: Homo sapiens

<400> SEQUENCE: 17
aaaaagcata cttggaatgg cccaaggata ggtgtaaatg                40

<210> SEQ ID NO 18
<211> LENGTH: 12
<212> TYPE: DNA
<213> ORGANISM: Artificial Sequence
<220> FEATURE:
<223> OTHER INFORMATION: Synthetic Linker

<400> SEQUENCE: 18
tcagcggtaa gc                12

<210> SEQ ID NO 19
<211> LENGTH: 13
<212> TYPE: DNA
<213> ORGANISM: Artificial Sequence
<220> FEATURE:
<223> OTHER INFORMATION: Synthetic Linker

<400> SEQUENCE: 19
ggccgcttac cgc                13

<210> SEQ ID NO 20
<211> LENGTH: 11
<212> TYPE: DNA
<213> ORGANISM: Artificial Sequence
<220> FEATURE:
<223> OTHER INFORMATION: Synthetic Linker

<400> SEQUENCE: 20
taagcttaac g                11

<210> SEQ ID NO 21
<211> LENGTH: 19
<212> TYPE: DNA
<213> ORGANISM: Artificial Sequence
<220> FEATURE:
<223> OTHER INFORMATION: Synthetic Linker

<400> SEQUENCE: 21
ggccgctaaa gcttatgca                19

<210> SEQ ID NO 22
<211> LENGTH: 173
<212> TYPE: DNA
<213> ORGANISM: Artificial Sequence
<220> FEATURE:
<223> OTHER INFORMATION: Synthetic Tag

<400> SEQUENCE: 22
ggtaccttct gacatcattg taattttaag catcgtggat attcccggga                50 aagttttttgg atgccattgg ggatttcctc tttagatctg gcgcggtccc                100
aggtccactt cgcatattaa ggtgacgcgt gtggcctcga acaccgagcg                150
accctgcagc gacccgcaag ctt                173

<210> SEQ ID NO 23
<211> LENGTH: 11
<212> TYPE: PRT
<213> ORGANISM: Artificial Sequence
<220> FEATURE:
<223> OTHER INFORMATION: Synthetic Tag -continued

<400> SEQUENCE: 23

Gly Arg Ala Asp Tyr Lys Asp Asp Asp Asp Lys
 1               5                  10

<210> SEQ ID NO 24
<211> LENGTH: 20
<212> TYPE: DNA
<213> ORGANISM: Homo sapiens

<400> SEQUENCE: 24
gcgggaagga ttttgggtaa                                          20

<210> SEQ ID NO 25
<211> LENGTH: 25
<212> TYPE: DNA
<213> ORGANISM: Homo sapiens

<400> SEQUENCE: 25
gatcccaact agacaaagac tggtc                                    25

<210> SEQ ID NO 26
<211> LENGTH: 33
<212> TYPE: DNA
<213> ORGANISM: Homo sapiens

<400> SEQUENCE: 26
tgagagctgc gataaagtcc taggttccca tat                           33

<210> SEQ ID NO 27
<211> LENGTH: 48
<212> TYPE: DNA
<213> ORGANISM: Homo sapiens

<400> SEQUENCE: 27
ggattctaat acgactcact atagggcaaa ctctgccctg tgatgtca            48

<210> SEQ ID NO 28
<211> LENGTH: 48
<212> TYPE: DNA
<213> ORGANISM: Homo sapiens

<400> SEQUENCE: 28
ctatgaaatt aaccctcact aaagggaacg agggcaattt ccacttag            48

<210> SEQ ID NO 29
<211> LENGTH: 48
<212> TYPE: DNA
<213> ORGANISM: Homo sapiens

<400> SEQUENCE: 29
ggattctaat acgactcact atagggctgg caataaactg gagacact            48

<210> SEQ ID NO 30
<211> LENGTH: 48
<212> TYPE: DNA
<213> ORGANISM: Homo sapiens

<400> SEQUENCE: 30
ctatgaaatt aaccctcact aaagggattg agttgttctt gggttgtt            48

<210> SEQ ID NO 31
<211> LENGTH: 16
<212> TYPE: PRT
<213> ORGANISM: Homo sapiens

```
<400> SEQUENCE: 31

Ser Ala Lys Thr Arg Phe Trp Lys Asn Val Arg Tyr His Met Pro
 1               5                  10                  15
Val

<210> SEQ ID NO 32
<211> LENGTH: 16
<212> TYPE: PRT
<213> ORGANISM: Homo sapiens

<400> SEQUENCE: 32

Ala Gln Arg Glu Gly Phe Trp Val Asn Leu Arg Ala Ala Ile Lys
 1               5                  10                  15
Ser
```